United States Patent
Horiguchi et al.

(10) Patent No.: US 8,650,047 B2
(45) Date of Patent: *Feb. 11, 2014

(54) BLOOD SUGAR MEASURING DEVICE

(71) Applicant: TERUMO Kabushiki Kaisha, Shibuya-ku (JP)

(72) Inventors: Hiroko Horiguchi, Ashigarakami-gun (JP); Yoshihisa Sugawara, Ashigarakami-gun (JP); Toshihisa Nakamura, Nakakoma-gun (JP); Yoshiaki Yaguchi, Nakakoma-gun (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/678,589

(22) Filed: Nov. 16, 2012

(65) Prior Publication Data

US 2013/0110552 A1 May 2, 2013

Related U.S. Application Data

(63) Continuation of application No. 12/676,839, filed as application No. PCT/JP2008/066035 on Sep. 5, 2008, now Pat. No. 8,326,650.

(30) Foreign Application Priority Data

Sep. 7, 2007 (JP) ................. 2007-233445
Sep. 7, 2007 (JP) ................. 2007-233446

(51) Int. Cl.
G06F 19/00 (2011.01)
(52) U.S. Cl.
USPC ............................................................ 705/3
(58) Field of Classification Search
USPC ............................................................ 705/3
See application file for complete search history.

(56) References Cited

U.S. PATENT DOCUMENTS 4,857,713 A 8/1989 Brown
6,656,114 B1 12/2003 Poulsen et al.
(Continued)

FOREIGN PATENT DOCUMENTS

JP 10-019888 A 1/1998
JP 10-318928 A 12/1998
(Continued)

OTHER PUBLICATIONS

International Search (PCT/ISA/210) issued on Nov. 25, 2008 by Japanese Patent Office as the International Searching Authority for International Application No. PCT/JP2008/066035.

(Continued)

Primary Examiner — John Pauls
(74) Attorney, Agent, or Firm — Buchanan Ingersoll & Rooney PC

(57) ABSTRACT

A blood glucose measuring device capable of collectively performing blood glucose measurement process and collectively performing insulin administration process on many patients. When having read a patient ID with a patient ID reading section, a control section identifies a record of the patient of a measurement/administration results table. The control section does not perform blood glucose measurement on the patient of the identified record which shows that a blood glucose measurement flag is "true" and an insulin administration confirmation flag is "false", and displays an insulin dosage on a display unit with respect to the patient by referring to a prescription information table based on the blood glucose level has been measured. The control section does not display the insulin dosage on the display unit again for the patient whose record is identified which shows that the insulin administration confirmation flag is "true".

3 Claims, 41 Drawing Sheets

(56) References Cited

U.S. PATENT DOCUMENTS

| | | |
|---|---|---|
| 2004/0048394 A1 | 3/2004 | Kirchhevel |
| 2004/0117062 A1 | 6/2004 | Bonney et al. |
| 2004/0172284 A1 | 9/2004 | Sullivan et al. |
| 2004/0186357 A1 | 9/2004 | Soderberg et al. |
| 2005/0019848 A1 | 1/2005 | Lee et al. |
| 2005/0197553 A1 | 9/2005 | Cooper |
| 2007/0219432 A1 | 9/2007 | Thompson |

FOREIGN PATENT DOCUMENTS

| | | |
|---|---|---|
| JP | 2000-60803 A | 2/2000 |
| JP | 2003-500744 A | 1/2003 |
| JP | 2003-099529 A | 4/2003 |
| JP | 2004-531304 A | 10/2004 |
| JP | 2004-533900 A | 11/2004 |
| JP | 2005-525161 A | 8/2005 |
| JP | 2006-107134 A | 4/2006 |
| JP | 2006-514842 A | 5/2006 |
| JP | 2007-537016 A | 12/2007 |
| WO | 00/72181 A2 | 11/2000 |
| WO | 03/005891 A1 | 1/2003 |
| WO | 2007/005170 A2 | 1/2007 |

OTHER PUBLICATIONS

Extended European Search Report issued Mar. 7, 2013, by the European Patent Office in corresponding European Patent Application No. 08829826.0. (9 pages).

Notice of Reasons for Rejection issued Jul. 26, 2013 by the Japanese Patent Office in corresponding Japanese Patent Application No. 2009-531285 (3 pages).

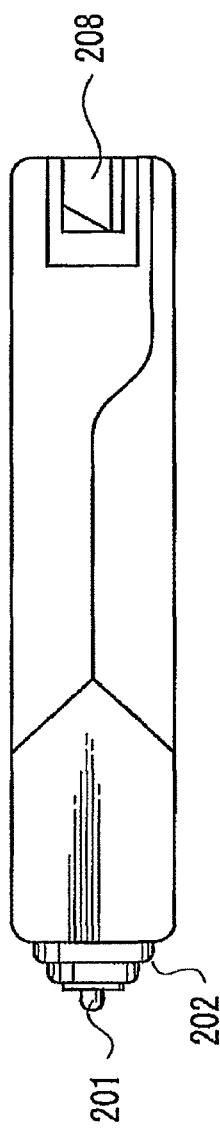
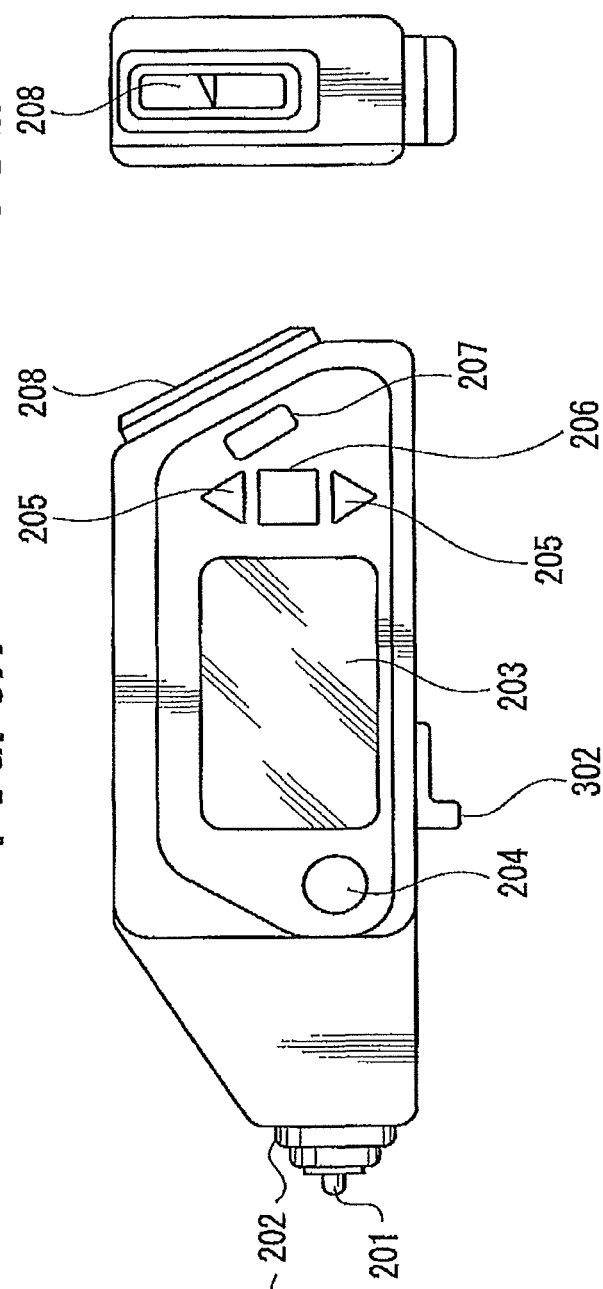
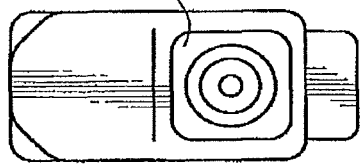

FIG. 16A

1602 MEASUREMENT/PRESCRIPTION TABLE

| |
|---|
| PATIENT ID |
| SCHEDULED MEASUREMENT TIME |
| BLOOD GLUCOSE MEASUREMENT FLAG |
| NUMBER OF PRESCRIPTIONS (0-3) |

FIG. 16B

1408 MEASUREMENT/PRESCRIPTION RESULTS TABLE

| |
|---|
| DATE AND TIME OF MEASUREMENT |
| PATIENT ID |
| USER ID |
| TIP LOT |
| TEMPERATURE |
| BLOOD GLUCOSE LEVEL |
| BLOOD GLUCOSE MEASUREMENT FLAG |
| SCHEDULED MEASUREMENT TIME |
| NUMBER OF INSULIN ADMINISTRATIONS |
| INSULIN ADMINISTRATION INFORMATION: |
|   DRUG NAME |
|   INSULIN DOSAGE |
|   INSULIN DOSAGE DISPLAY FLAG |
|   INSULIN ADMINISTRATION CONFIRMATION FLAG |

FIG. 16C

1502 PRESCRIPTION INFORMATION TABLE

| PATIENT ID | CLASSIFICATION NUMBER | BLOOD GLUCOSE LEVEL RANGE | DRUG NAME | PRESCRIPTION |
|---|---|---|---|---|
| 123456 | 1 | 0-79 | ULTRA RAPID ACTING INSULIN | — |
| 123456 | 1 | 80-99 | ULTRA RAPID ACTING INSULIN | — |
| 123456 | 1 | 100-149 | ULTRA RAPID ACTING INSULIN | 2UNIT |
| 123456 | 1 | 150-199 | ULTRA RAPID ACTING INSULIN | 4UNIT |
| 123456 | 1 | 200-249 | ULTRA RAPID ACTING INSULIN | 6UNIT |
| 123456 | 1 | 250-299 | ULTRA RAPID ACTING INSULIN | 7UNIT |
| 123456 | 1 | 300-349 | ULTRA RAPID ACTING INSULIN | 8UNIT |
| 123456 | 1 | 350-399 | ULTRA RAPID ACTING INSULIN | 9UNIT |
| 123456 | 1 | 400- | ULTRA RAPID ACTING INSULIN | 10UNIT |
| 135792 | 1 | 0-79 | | — |
| 135792 | 1 | 80-99 | | — |
| 135792 | 1 | 100-149 | ULTRA RAPID ACTING INSULIN | 2UNIT |
| 135792 | 1 | 150-199 | ULTRA RAPID ACTING INSULIN | 4UNIT |
| 135792 | 1 | 200-249 | ULTRA RAPID ACTING INSULIN | 6UNIT |
| 135792 | 1 | 250- | ULTRA RAPID ACTING INSULIN | 7UNIT |
| 135792 | 2 | 0-79 | | — |
| 135792 | 2 | 80-99 | | — |
| 135792 | 2 | 100-149 | SLOW ACTING INSULIN | 1UNIT |
| 135792 | 2 | 150-149 | SLOW ACTING INSULIN | 2UNIT |
| 135792 | 2 | 200-249 | SLOW ACTING INSULIN | 3UNIT |
| 135792 | 2 | 250- | SLOW ACTING INSULIN | 4UNIT | ively performing insulin administration process on many patients, while ruling out the risk of misidentification and misprescription among the patients.

BLOOD SUGAR MEASURING DEVICE

TECHNICAL FIELD

The present invention relates to a technique preferably applied to a blood sugar (glucose) measuring device.

More particularly, the present invention relates to a blood glucose measuring device capable of measuring blood glucose level for a plurality of patients and administering insulin to the patients in hospital in a rapid, safe and reliable manner.

BACKGROUND ART

As is well known, diabetes results from inappropriate secretion of insulin by the pancreas. Thus, it is necessary to measure the blood glucose level for a diabetic patient before meals, and administer insulin to the patient according to the measured level.

Conventionally, there has been a small sized blood glucose measuring device developed, manufactured and marketed by the applicant of the present invention, the blood glucose level being designed for measuring blood glucose of a patient at home by the patient himself/herself or by a family member of the patient. Patent applications relating to the blood glucose measuring device are disclosed in Patent Documents 1 and 2.

[Patent Document 1] Japanese Unexamined Patent Application Publication No. H10-19888

[Patent Document 2] Japanese Unexamined Patent Application Publication No. H10-318928

DISCLOSURE OF THE INVENTION

Problems to be Solved by the Invention

It has been reported that the blood glucose measuring device designed for home use is actually used as it is in clinical practice in hospitals where many patients are hospitalized.

However, the blood glucose measuring device designed for home use only has a function of measuring blood glucose, and there are no safety measures for preventing accidents such as patient misidentification, duplicated administration of insulin and the like.

Further, in the blood glucose measuring device designed for home use, functions for improving efficiency of medical practice, such as collectively performing blood glucose measurement process and collectively performing insulin administration process on many patients, are not taken into consideration.

Nowadays, a new blood glucose measuring device having improved functions in terms of safety, efficiency and the like is desired in order to meet the needs of clinical practice.

The present invention is made in view of the above-mentioned problems, and an object of the present invention is to provide a safe blood glucose measuring device capable of ruling out the risk of misidentification and misprescription among the patients.

Further, another object of the present invention is to provide a safe and efficient blood glucose measuring device capable of collectively performing blood glucose measurement process and collectively performing insulin administration process on many patients, while ruling out the risk of misidentification and misprescription among the patients.

To solve the aforesaid problems, a blood glucose measuring device according to an aspect of the present invention includes: a patient ID reading section for acquiring a patient ID assigned to a patient; a blood glucose measuring section for measuring blood glucose level of the blood drawn from the patient; a nonvolatile storage for storing predetermined data; a prescription information table stored in the nonvolatile storage, the prescription information table having prescription information stored therein in a manner in which the prescription information can be identified by the patient ID, the prescription information including kind and dosage of drugs for being administered corresponding to the blood glucose level of each of a plurality of patients; a search section for searching, with blood glucose level and the patient ID, the prescription information table to acquire the prescription information of the patient; a display unit for displaying the prescription information acquired by the search section; an operating section for allowing an operator to input, in a state where the prescription information is displayed on the display unit, whether the prescription has been executed or not; and a measurement/prescription results table stored in the nonvolatile storage, the measurement/prescription results table having: a patient ID field having the patient ID acquired by the patient ID reading section stored therein, a blood glucose level field for recording the blood glucose level of the patient measured by the blood glucose measuring section, a blood glucose measurement flag field for recording whether the blood glucose has been measured by the blood glucose measuring section or not, and an insulin administration confirmation flag field for recording whether the prescription has been executed or not after the prescription information has been displayed by the display unit.

To solve the aforesaid problems, the blood glucose measuring device according to the aforesaid aspect of the present invention further includes: a recording section; and a control section, wherein, when obtaining the blood glucose level from the blood glucose measuring section, the recording section records the blood glucose level in the blood glucose level field and records a logical true in the blood glucose measurement flag field of a record the measurement/prescription results table, the record being identified by the patient ID, while when obtaining operation information from the operating section, the recording section records a logical true in the insulin administration confirmation flag field of the record, and wherein, after obtaining the patient ID by the patient ID reading section, the control section confirms the blood glucose measurement flag field and the insulin administration confirmation flag field of the record, and if the blood glucose measurement flag field of the record identified by the patient ID of the measurement/prescription results table is "true" and the insulin administration confirmation flag field of the record is "false", the control section will control the search section to obtain the prescription information, while if the blood glucose measurement flag field of the record is "true" and the insulin administration confirmation flag field of the record is "true", the control section will not control the search section to obtain the prescription information.

To solve the aforesaid problems, a blood glucose measuring device according to another aspect of the present invention includes: a patient ID reading section for acquiring a patient ID assigned to a patient; a blood glucose measuring section for measuring the blood glucose level of the blood drawn from the patient; a nonvolatile storage for storing predetermined data; a prescription information table stored in the nonvolatile storage, the prescription information table having prescription information stored therein in a manner in which the prescription information can be identified by the patient ID, the prescription information including kind and dosage of drugs for being administered corresponding to the blood glucose level of each of a plurality of patients; a search section for searching, with blood glucose level and the patient ID, the prescription information table to acquire the prescription information of the patient; a display unit for displaying the prescription information acquired by the search section; an operating section for allowing an operator to input, in a state where the prescription information is displayed on the display unit, whether the prescription has been executed or not; a measurement/prescription results table stored in the nonvolatile storage, the measurement/prescription results table having: a patient ID field having the patient ID stored therein, a blood glucose level field for recording the blood glucose level of the patient measured by the blood glucose measuring section, a blood glucose measurement flag field for recording whether the blood glucose has been measured by the blood glucose measuring section or not, and an insulin administration confirmation flag field for recording whether the prescription has been executed or not after the prescription information has been displayed by the display unit; a recording section; and a control section, wherein, when obtaining the blood glucose level from the blood glucose measuring section, the recording section records the blood glucose level in the blood glucose level field and records a logical true in the blood glucose measurement flag field of a record of the measurement/prescription results table, the record being identified by the patient ID, while when obtaining operation information from the operating section, the recording section records a logical true in the insulin administration confirmation flag field of the record, and wherein, after reading the patient ID by the patient ID reading section, if the blood glucose measurement flag field of the record is "true" and the insulin administration confirmation flag field of the record is "false", the control section will cause the search section to search the prescription information table with the blood glucose level recorded in the blood glucose level field of the record and the patient ID to acquire the prescription information and cause the display unit to display the prescription information.

The control section sets the measurement/prescription results table to "true" with respect to the patient who has received insulin administration.

When performing blood glucose measurement again on the same patient, the "true" of the field of the insulin administration confirmation flag is detected, and therefore insulin dosage will not be displayed.

Advantages of the Invention

According to the present invention, it is possible to provide a safe blood glucose measuring device capable of ruling out the risk of misidentification and misprescription among the patients.

Further, according to the present invention, it is possible to provide a safe and efficient blood glucose measuring device capable of collectively performing blood glucose measurement process and collectively performing insulin administration process on many patients, while ruling out the risk of misidentification, such as duplicated administration of insulin, and misprescription among the patients.

BRIEF DESCRIPTION OF DRAWINGS

FIGS. 3A, 3B, and 3C are views showing the blood glucose meter according to the aforesaid embodiment when viewed from four directions.

FIGS. 16A, 16B and 16C are schematic views showing tables stored in the blood glucose meter.

BEST MODES FOR CARRYING OUT THE INVENTION

An embodiment of the present invention will be described below with reference to FIGS. 1 to 44.

[Blood Glucose Measuring System 101]

Figure 1:
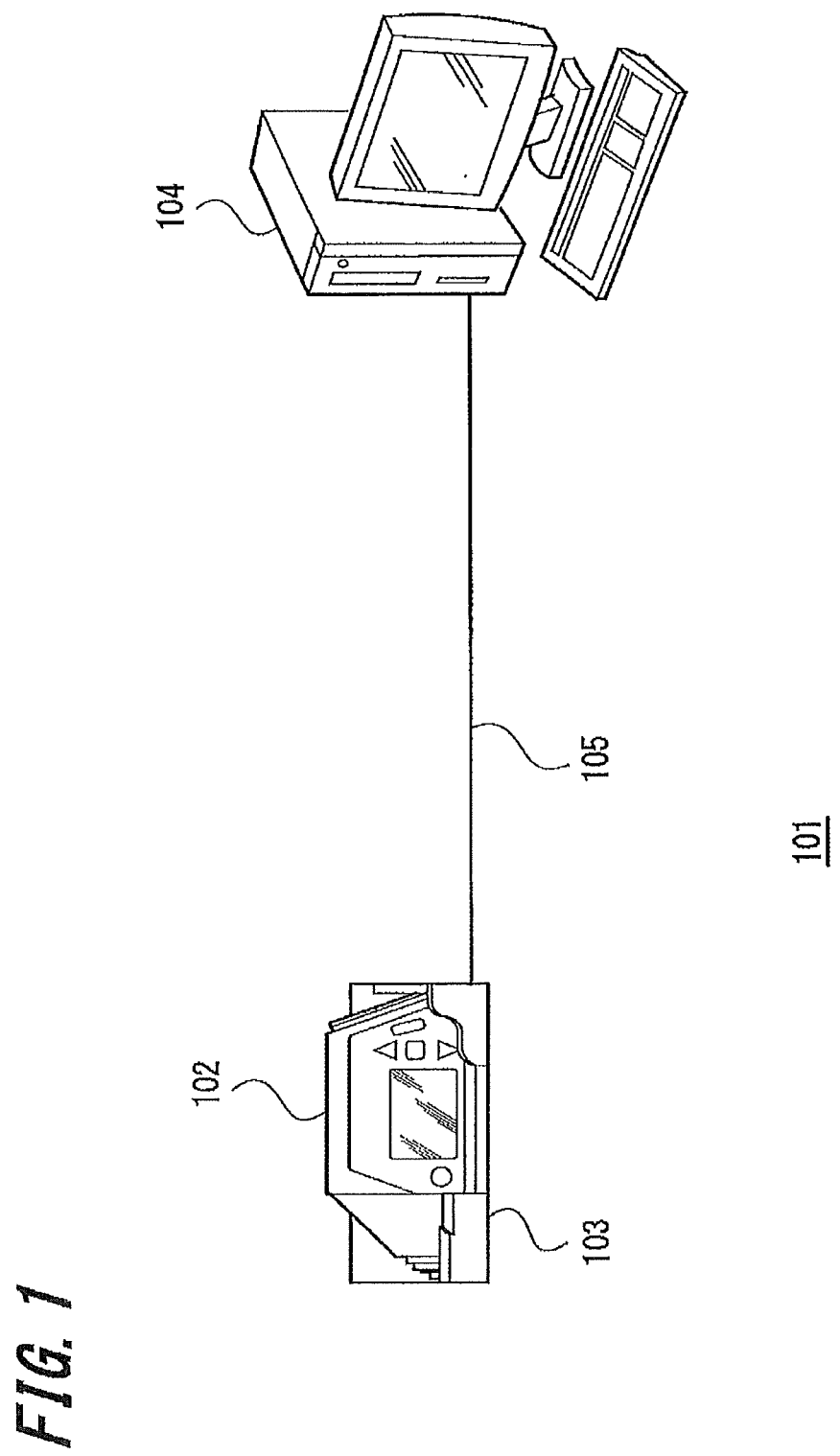
FIG. 1 is a schematic view showing the overall configuration of a blood glucose measuring system according to an embodiment of the present invention.

FIG. 1 is a schematic view showing the overall configuration of a blood glucose measuring system according to an embodiment of the present invention.

A blood glucose measuring system 101 includes a blood glucose meter 102, which is a blood glucose measuring device, a cradle 103 and a measurement data management device 104.

The blood glucose meter 102 is a portable device that basically fits in the palm of an adult hand and that is operated using a secondary battery such as a lithium-ion secondary battery.

In the case where the blood glucose level of a patient is measured by a doctor, a nurse or the like, generally the blood glucose meter 102 is brought into a ward of a hospital, and a tiny amount of blood is drawn from the patient to measure the blood glucose level. The blood drawing process and the blood glucose measurement process are performed following the steps of: sticking the tip of a finger of the patient with a puncture tool, and causing the blood exuded from the fingertip to be soaked into a measuring tip attached to the blood glucose meter 102.

Make sure that the blood glucose meter 102 is mounted on the cradle 103 after performing the blood glucose measurement and insulin administration.

In addition to charging the battery of the blood glucose meter 102, the cradle 103 also functions as an interface through which the blood glucose meter 102 transmits/receives data to/from the measurement data management device 104.

The partner to/from which the blood glucose meter 102 transmits/receives data through the cradle 103 is the measurement data management device 104.

The measurement data management device 104, which is configured by a personal computer, is connected with the cradle 103 through a USB cable 105.

A known OS operates to execute the measurement data management device 104. Further, a program for causing the computer to function as the measurement data management device 104 operates under the OS.

As soon as the blood glucose meter 102 is mounted on the cradle 103, the communication between the blood glucose meter 102 and the measurement data management device 104 is performed through the cradle 103, and a below-mentioned measurement/prescription results table is transmitted to the measurement data management device 104.

Further, below-mentioned various tables can be uploaded to the blood glucose meter 102 from the measurement data management device 104.

The details about these tables will be described later.

[Appearance: Blood Glucose Meter 102]

Figure 2A:
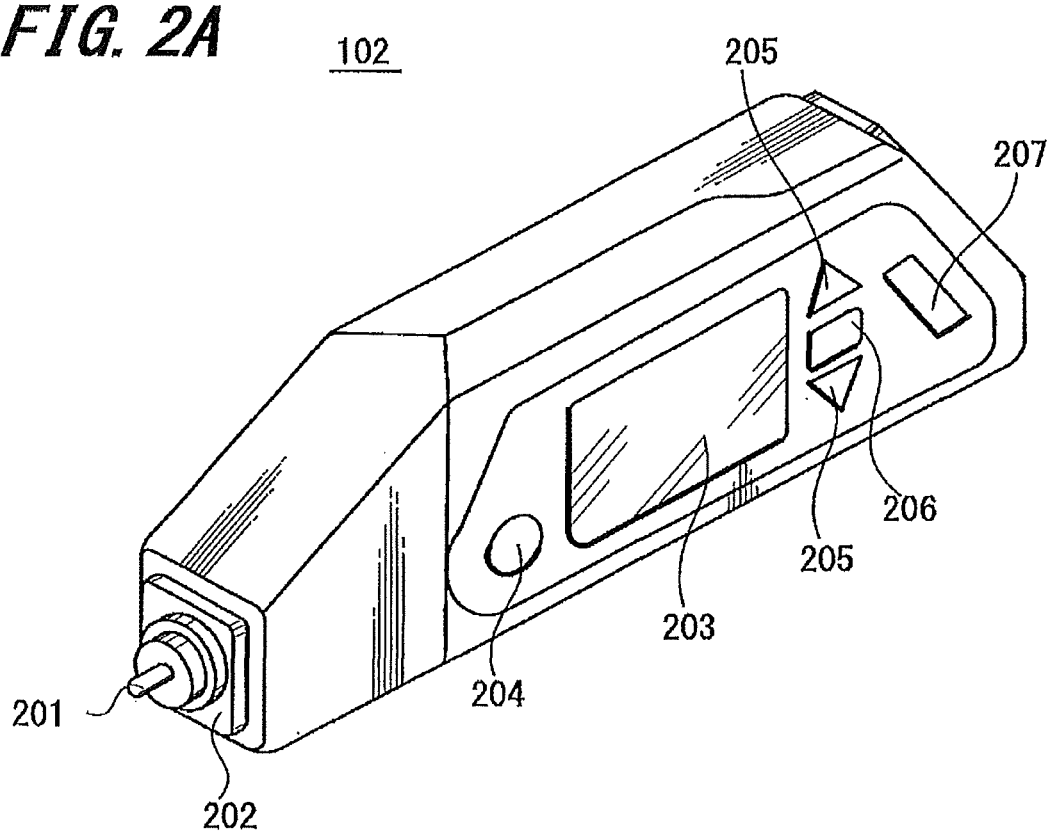
FIGS. 2A and 2B are perspective views showing the appearance of a blood glucose meter according to the aforesaid embodiment of the present invention.
Figure 2B:
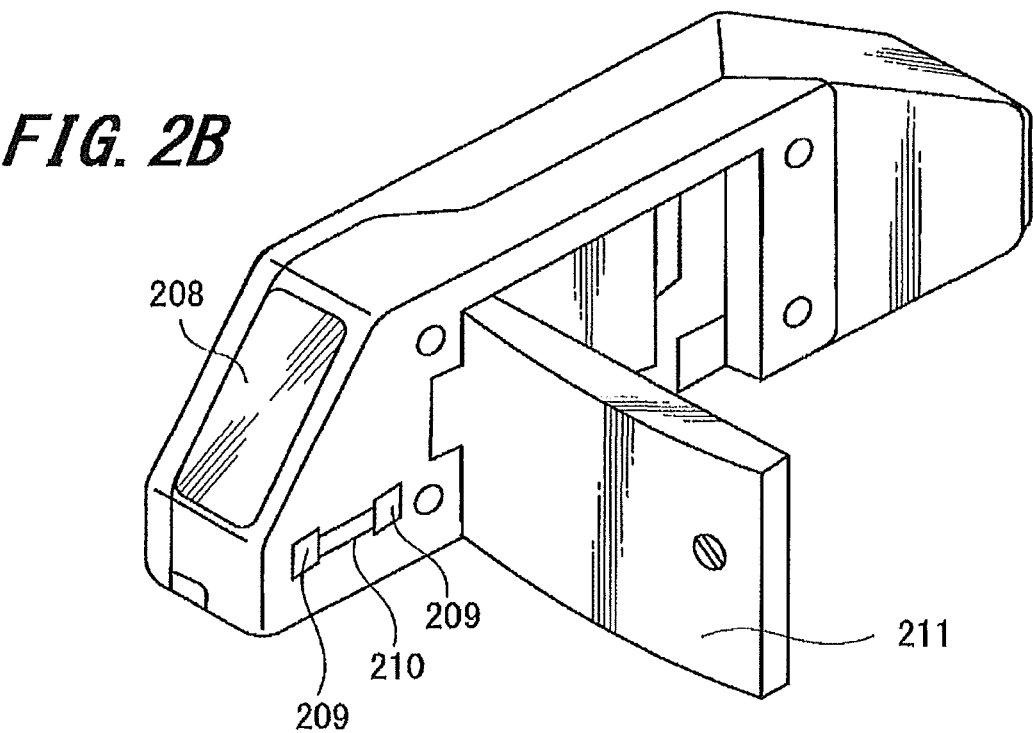

FIGS. 2A and 2B are perspective views showing the appearance of the blood glucose meter 102.

FIGS. 3A, 3B, 3C and 3D are views showing the blood glucose meter when viewed from four directions.

In order to facilitate description, the surface where an LCD is provided (as shown in FIGS. 2A and 3A) is referred to as a "body front surface" hereinafter, and the surface where a battery lid is provided (as shown in FIG. 2B) is referred to as a "body rear surface".

As shown in FIGS. 3A and 3C, an optical measuring section 202 is provided at the tip end of the blood glucose meter 102.

The optical measuring section 202 has a shape allowing a blood glucose measuring tip 212 (referred to as "measuring tip 212" hereinafter) to be attached and detached. The used measuring tip 212 can be detached from the optical measuring section 202 by operating an eject lever 302.

As shown in FIG. 2A and FIG. 3A, a power switch 204, Cursor keys 205, an Enter key 206 and a Bar-code key 207 are arranged on the side surface (the body front surface) where the LCD 203 (a liquid crystal display) is provided, at positions beside the LCD 203.

The power switch 204 is used to switch on and off the power of the blood glucose meter 102.

The Cursor keys 205 are used to move the cursor to select one of a plurality of items displayed on the LCD 203.

The Enter key 206 is used to issue an instruction for "executing" or "selecting" the item selected by the cursor.

The Bar-code key 207 is used to cause a bar-code reader 208 shown in FIG. 3D to operate, wherein the bar-code reader 208 is arranged on a side of the blood glucose meter 102 opposite to the side where the optical measuring section 202 is arranged.

The bar-code reader 208 is a bar-code reading device configured by a combination of a known red laser diode and a light-receiving element such as a phototransistor. Incidentally, an image sensor such as a CCD, a CMOS or the like can be used instead of the light-receiving element.

The basic mechanism of the blood glucose meter 102 for measuring blood glucose is identical to that of the conventional arts, and will be briefly described below.

The measuring tip 212 is attached to the optical measuring section 202, the fingertip of the patient is stuck with a puncture tool, and the blood exuded from the fingertip is soaked into the measuring tip 212. A test paper made of a porous membrane such as a polyether sulfone membrane is provided inside the measuring tip 212. Further, when the blood soaked into the measuring tip 212 is permeated into the test paper, the blood will be reacted with the reagent contained in the test paper, so that the test paper develops a color. The color reaction requires about several to ten and several seconds, and the reaction time is affected by the ambient temperature.

After a predetermined reaction time has elapsed, a light-emitting element is caused to omit light, the light emitted from the light-emitting element irradiate to the test paper, and the light reflected from the test paper is received by the light-receiving element. Further, an analog light-receiving intensity signal obtained from the light-receiving element is converted into a digital value, and thereafter the digital value is converted into the blood glucose level to be displayed on the LCD 203.

Incidentally, the mechanism of blood glucose measurement on the side of the blood glucose meter 102 is not limited to the aforesaid optical measurement method in which a coloring reagent is used, but may be any other methods possible to be used to perform the conventional blood glucose measurement, such as an electrochemical sensor method or the like.

As shown in FIG. 2B, a power terminal 209 and an infrared communication window 210 are provided in the body rear surface on the side of the bar-code reader 208. When the blood glucose meter 102 is mounted on the cradle 103, the power terminal 209 is brought into contact with a charging terminal 402 (see FIGS. 4A and 4B) provided in the cradle 103, so that the blood glucose meter 102 is charged while an infrared communication between the blood glucose meter 102 and the cradle 103 is performed. Incidentally, the battery lid 211 is also provided on the body rear surface.

[Appearance: Cradle 103]

Figure 4A:
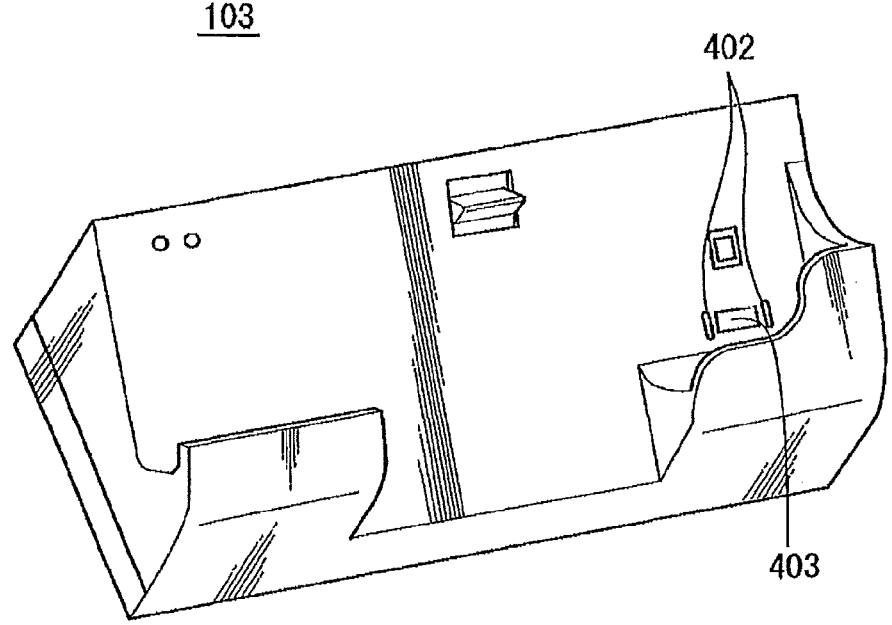
FIGS. 4A and 4B are views showing the appearance of a cradle in a state when the blood glucose meter is mounted thereon.
Figure 4B:
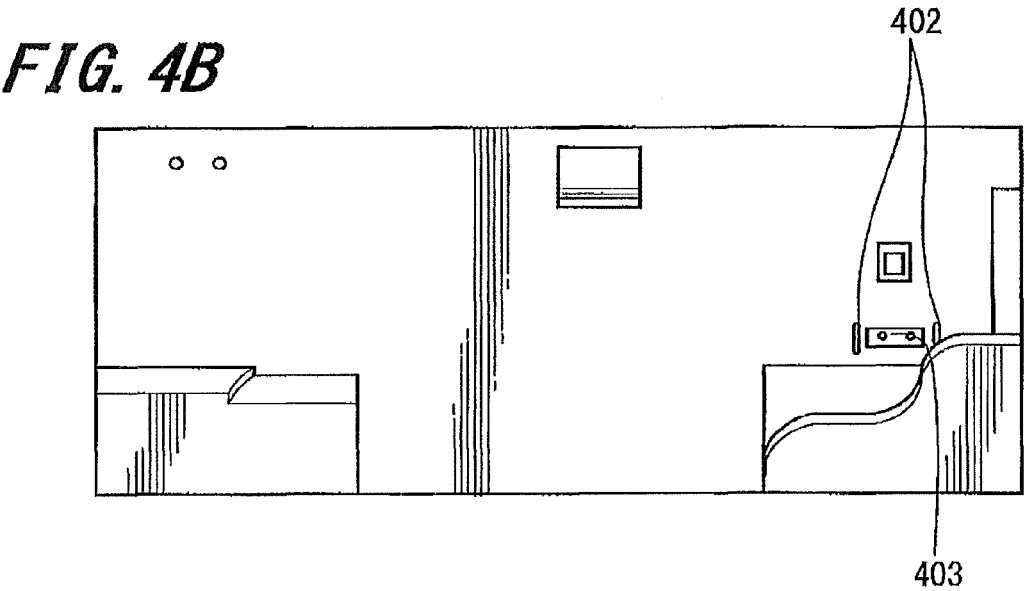
Figure 5A:
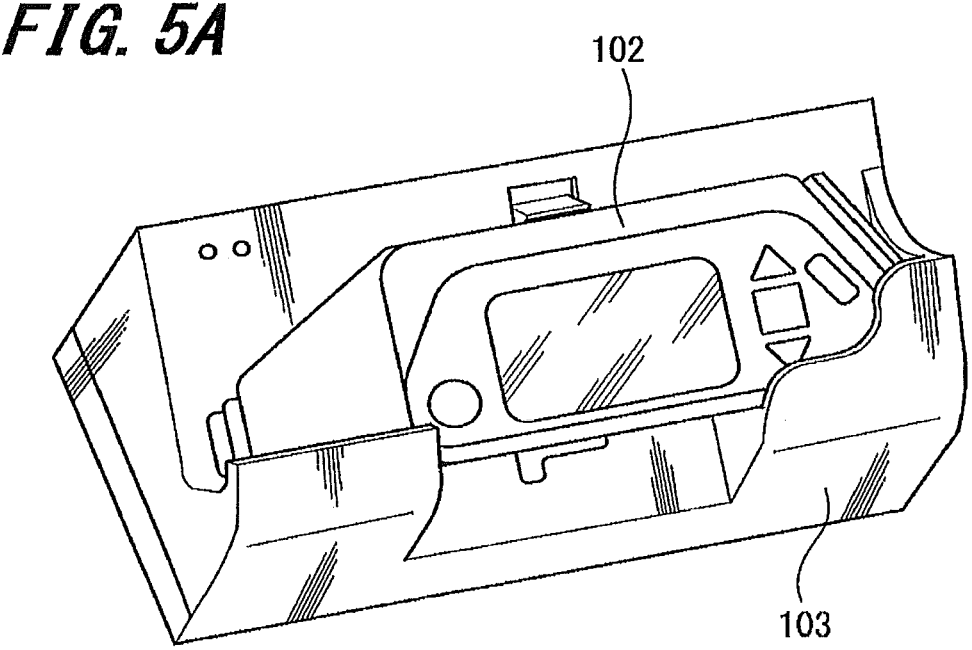
FIGS. 5A and 5B are views showing the appearance of the cradle in a state when the blood glucose meter is removed therefrom.
Figure 5B:
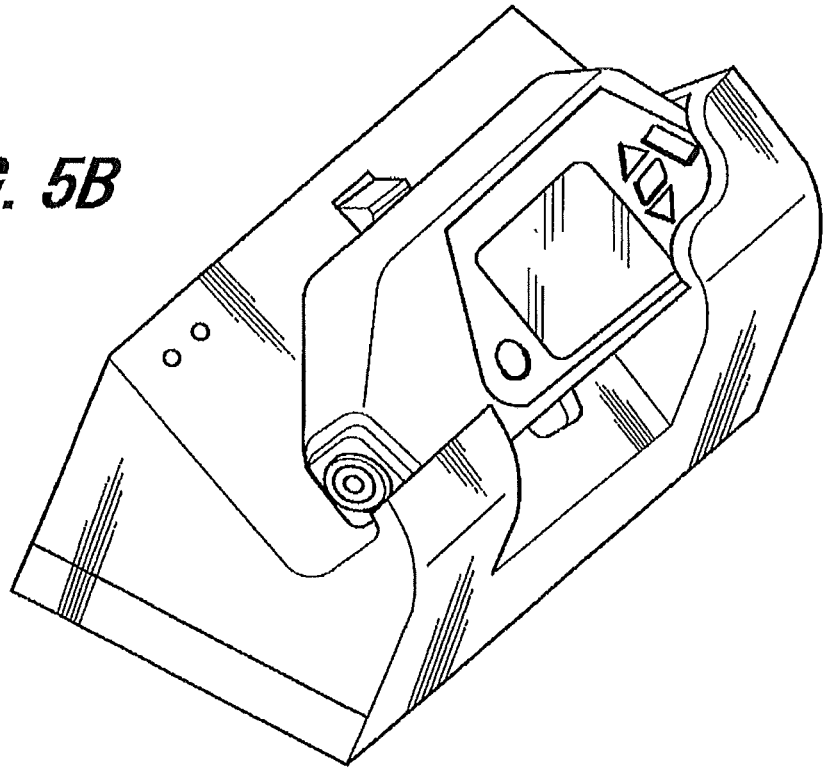

FIGS. 4A and 4B are views showing the appearance of the cradle 103 in a state when the blood glucose meter 102 is removed therefrom, and FIGS. 5A and 5B are views showing the appearance of the cradle 103 in a state when the blood glucose meter 102 is mounted thereon.

As shown in FIGS. 4A and 4B, the charging terminal 402 is arranged in the cradle 103 at a position corresponding to the power terminal 209 of the blood glucose meter 102. Similarly, an infrared communication window 403 is arranged in the cradle 103 at a position corresponding to the infrared communication window 210 of the blood glucose meter 102.

An infrared light-emitting diode and a phototransistor are provided inside both the infrared communication window 210 of the blood glucose meter 102 and the infrared communication window 403 of the cradle 103. These components constitute a known IrDA (Infrared Data Association) based infrared serial communication interface.

As shown in FIG. 1, the cradle 103 is connected to the measurement data management device 104 through the USB cable 105. The cradle 103 has a function of charging the battery of the blood glucose meter 102. Since it is possible to connect many cradles 103 to the measurement data management device 104, the cradle 103 is configured as a self-powered device which does not receive power supply from a USB terminal of the measurement data management device 104.

[Hardware: Blood Glucose Meter 102]

Figure 6:
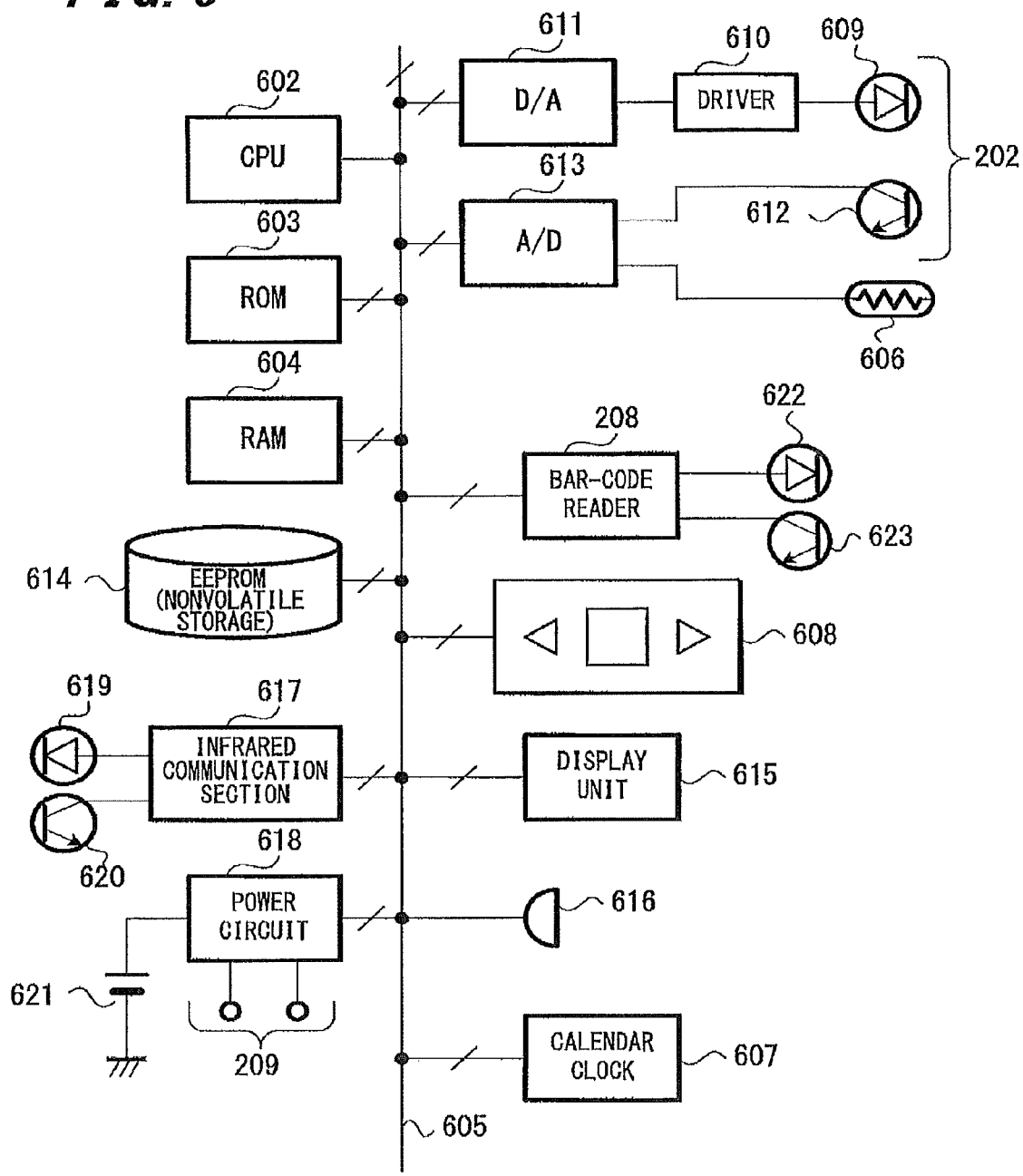
FIG. 6 is a block diagram showing the internal configuration of the blood glucose meter.

FIG. 6 is a block diagram showing the internal configuration of the blood glucose meter 102.

The blood glucose meter 102 includes a CPU 602, a ROM 603, a RAM 604, and a bus 605 for connecting the CPU 602, the ROM 603 and the RAM 604. In addition to the aforesaid components, a section for providing a data input function and a section for providing a data output function are also connected to the bus 605.

For sake of convenience, hereinafter the CPU 602, the ROM 603, the RAM 604 and the bus 605 are referred to as a microcomputer that constitutes the blood glucose meter 102.

The section for providing a data input function of the blood glucose meter 102 includes the optical measuring section 202 for obtaining blood glucose measurement data, a thermistor 606 for obtaining temperature data, the bar-code reader 208, a calendar clock 607, and an operating section 608.

The optical measuring section 202 includes a light-emitting portion and a light-receiving portion, wherein the light-emitting portion includes a light-emitting diode 609, a driver 610 of the light-emitting diode 609, and a D/A converter 611 connected to the driver 610, and the light-receiving portion includes a phototransistor 612 and an A/D converter 613.

Since the test paper arranged inside the measuring tip 212 needs to be irradiated by light of a suitable intensity, the light-emitting diode 609 is controlled so as to emit light based on light-emitting intensity data stored in a below-mentioned nonvolatile storage 614. In other words, the light-emitting intensity data is read out from the nonvolatile storage 614, converted into an analog voltage signal by the D/A converter 611, and then power-amplified by the driver 610 to drive the light-emitting diode 609 to emit light.

On the other hand, a signal voltage of intensity of the light received by the phototransistor 612 is converted into digital data by the A/D converter 613. Further, the converted digital data is converted into blood glucose level data by performing a predetermined arithmetic process executed by the CPU 602, and then the blood glucose level data is recorded in a predetermined area of the RAM 604 and a predetermined area of the nonvolatile storage 614.

Further, the blood glucose meter 102 has the thermistor 606, and ambient temperature of the blood glucose meter 102 can be measured based on the change of the resistance of the thermistor 606. Similar to the phototransistor 612, the resistance of the thermistor 606 is converted into digital data by the A/D converter 613, and the digital data is stored in a predetermined area of the RAM 604 and a predetermined area of the nonvolatile storage 614. Incidentally, since it is not necessary to simultaneously measure the light-receiving intensity and the temperature, the A/D converter 613 can be shared by the phototransistor 612 and the thermistor 606.

The bar-code reader 208 causes a red laser diode 622 to emit light, the reflected light is received by a phototransistor 623 so that the bar-code is read, and the data recorded on the bar-code is outputted to the bus 605.

The calendar clock 607 is a known IC also called as a "real-time clock" which provides a date and time data output function, and is mounted as standard on many microcomputers, personal computers and the like.

In the blood glucose meter 102 according to the present embodiment of the present invention, since it is necessary to acquire information regarding the date and time when the blood glucose was being measured, date and time information is important information. In other words, the data to be collected and the date and time information have very close relation with each other. Further, the date and time information when the blood glucose was being measured needs to be stored in a measurement/prescription results table 1408 (which is to be described later with reference to FIG. 14) along with the blood glucose level. For this reason, the calendar clock 607 is daringly shown in the drawings.

The operating section 608 is a known key switch formed by push-buttons, the operating section 608 including the Cursor keys 205 and the Enter key 206. The operating section 608 is used for a user to operate the blood glucose meter 102 according to the content displayed on a below-mentioned display unit 615 which is a LCD.

The section for providing a data output function of the blood glucose meter 102 includes the display unit 615 configured by the LCD 203, a buzzer 616 and an infrared communication section 617.

Various screens are displayed on the display unit 615 by a program stored in the ROM 603 and executed by the CPU 602. The details about display screens will be described later.

The buzzer 616 is mainly used to notify the user that the bar-code reader 208 has successfully read the bar-code, that the measurement operation of the blood glucose measurement has completed, that the infrared communication has completed, or that an error message is displayed. The buzzer 616 may also sound every time when operating the operating section 608 depending on setting.

As mentioned above, an infrared light-emitting diode 619 and a phototransistor 620 are connected to the infrared communication section 617, and these components constitute an IrDA based serial interface. When detecting that the blood glucose meter 102 has received power supply from the cradle 103 based on voltage changing of the power terminal 209, the power circuit 618 reports this fact to the CPU 602 through the bus 605. Further, based on the control of the CPU 602, the infrared communication function of the infrared communication section 617 is started, so that if the infrared communication between the blood glucose meter 102 and the cradle 103 is performed, the various tables stored in the nonvolatile storage 614 will transmits/receives data to/from the measurement data management device 104 and thereby these tables are updated.

In other words, when performing the infrared communication between the blood glucose meter 102 and the cradle 103, the infrared communication is immediately executed as soon as the blood glucose meter 102 is mounted on the cradle 103 without needing to operate the operating section 608 and the like of the blood glucose meter 102.

In addition to the data output function, the blood glucose meter 102 is provided with the nonvolatile storage 614 (which is an EEPROM) that provides data storage function. A patient table 1109, a user table 1113, a tip lot table 1117, a prescription information table 1502, a measurement/prescription table 1602, a measurement/prescription results table 1408 and the like (all these tables are to be described later with reference to FIGS. 11, 14, 15, 16A, 16B and 16C) are stored in the nonvolatile storage 614. These tables are updated when the communication between the blood glucose meter 102 and the measurement data management device 104 is performed through the cradle 103. Incidentally, a flash memory may also be used instead of the EEPROM.

[Hardware: Cradle 103]

Figure 7:
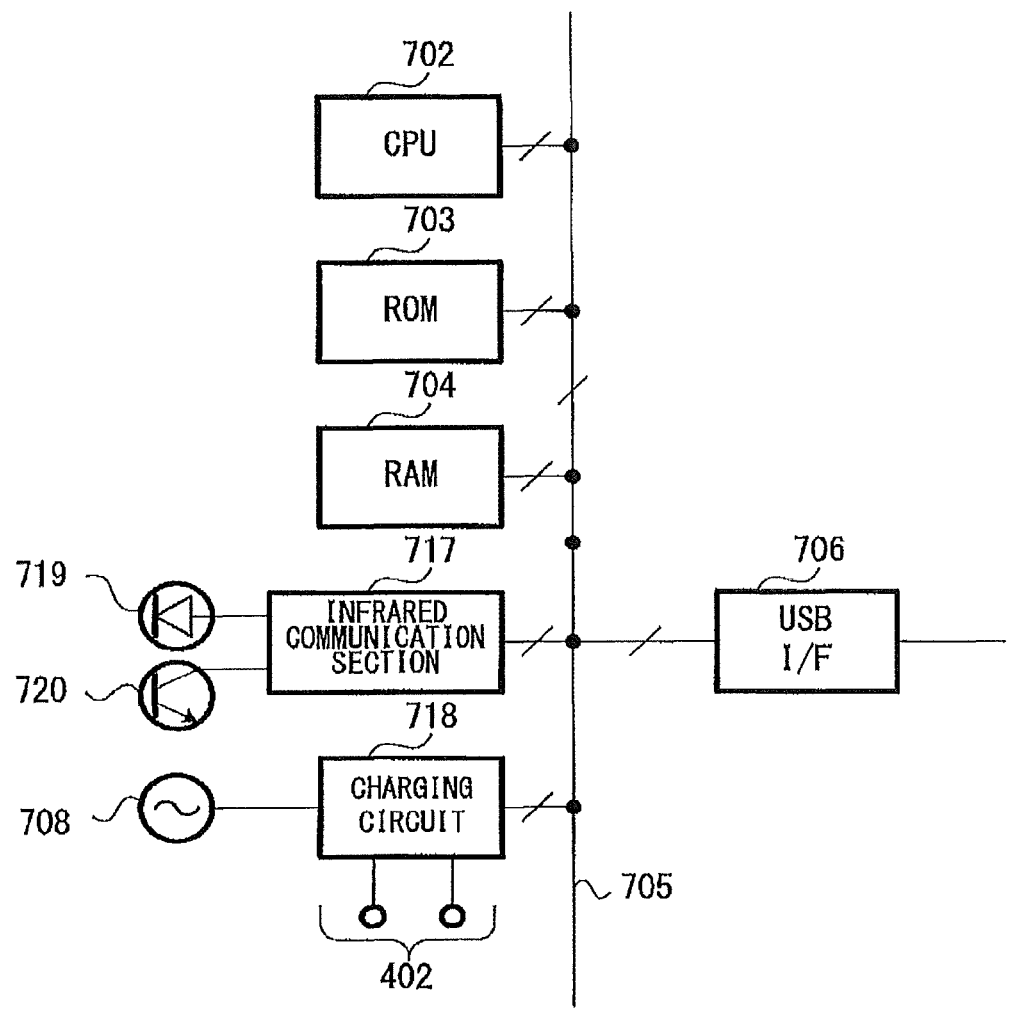
FIG. 7 is a block diagram showing the internal configuration of the cradle.

FIG. 7 is a block diagram showing the internal configuration of the cradle 103.

Figure 8:
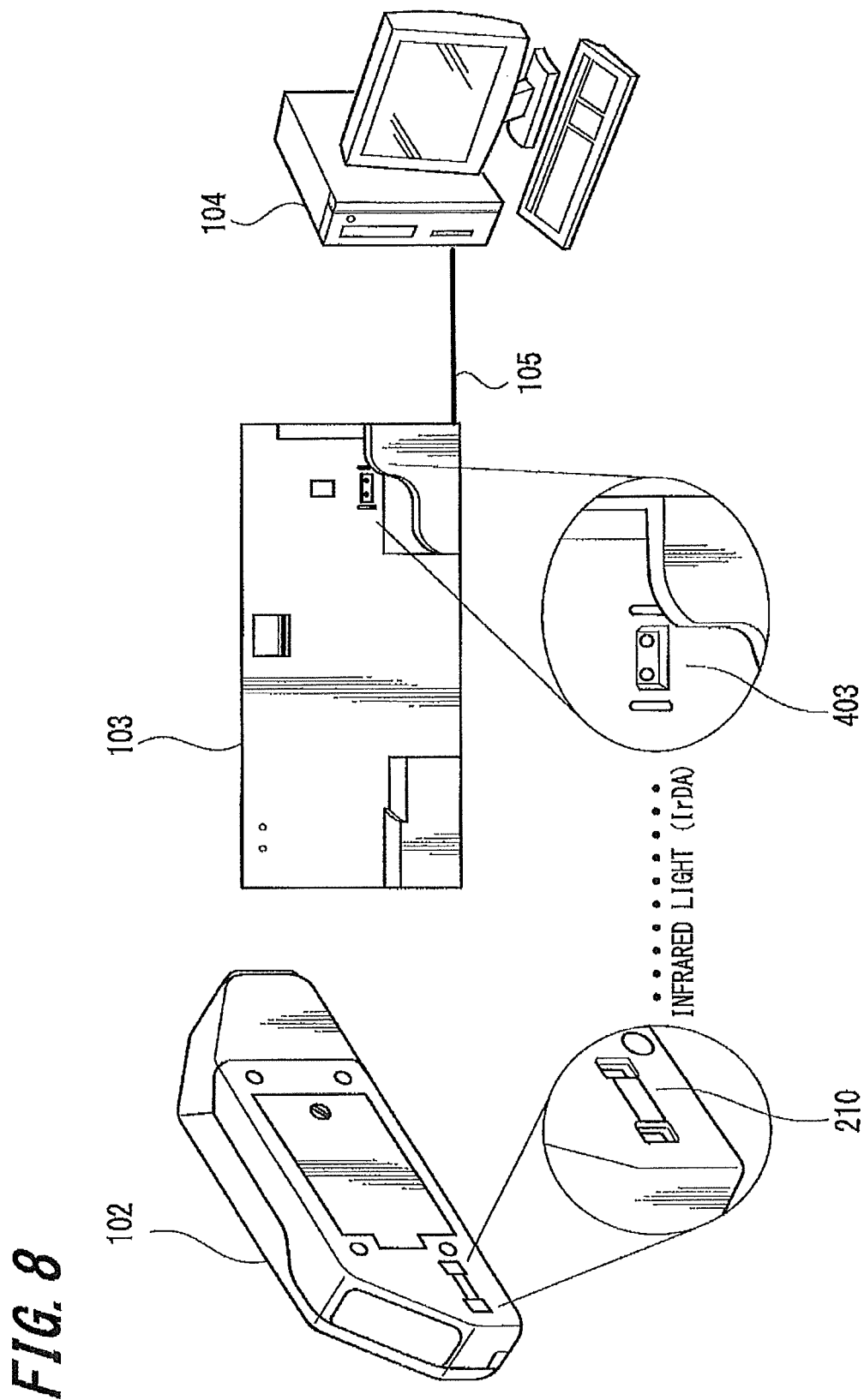
FIG. 8 is a block diagram showing connection state of the blood glucose meter, the cradle and a measurement data management device.

FIG. 8 is a view schematically showing connection state of the blood glucose meter 102, the cradle 103 and the measurement data management device 104.

As shown in FIG. 7, the cradle 103 includes a CPU 702, a ROM 703, a RAM 704, an infrared communication section 717, a USB interface (I/F) 706, a charging circuit 718 and a bus 705 which connects these components, wherein the CPU 702, the ROM 703 and the RAM 704 constitute a microcomputer, and the infrared communication section 717 has an infrared light-emitting diode 719 and a phototransistor 720 connected thereto.

When detecting that the blood glucose meter 102, which is a load, is connected based on voltage changing of the charging terminal 402, the charging circuit 718 reports this fact to the CPU 702 through the bus 705. Further, based on the control of the CPU 702, the infrared communication function of the infrared communication section 717 is started, so that the communication between the blood glucose meter 102 and the measurement data management device 104 is performed through the infrared communication section 717 and the USB interface 706.

As described above, the blood glucose meter 102 and the cradle 103 are connected with each other through the IrDA, and the cradle 103 and the measurement data management device 104 are connected with each other through the USB. From this aspect, the cradle 103 serves as an interface to enable data communication between the measurement data management device 104 and the blood glucose meter 102.

[Hardware: Measurement Data Management Device 104]

Figure 9:
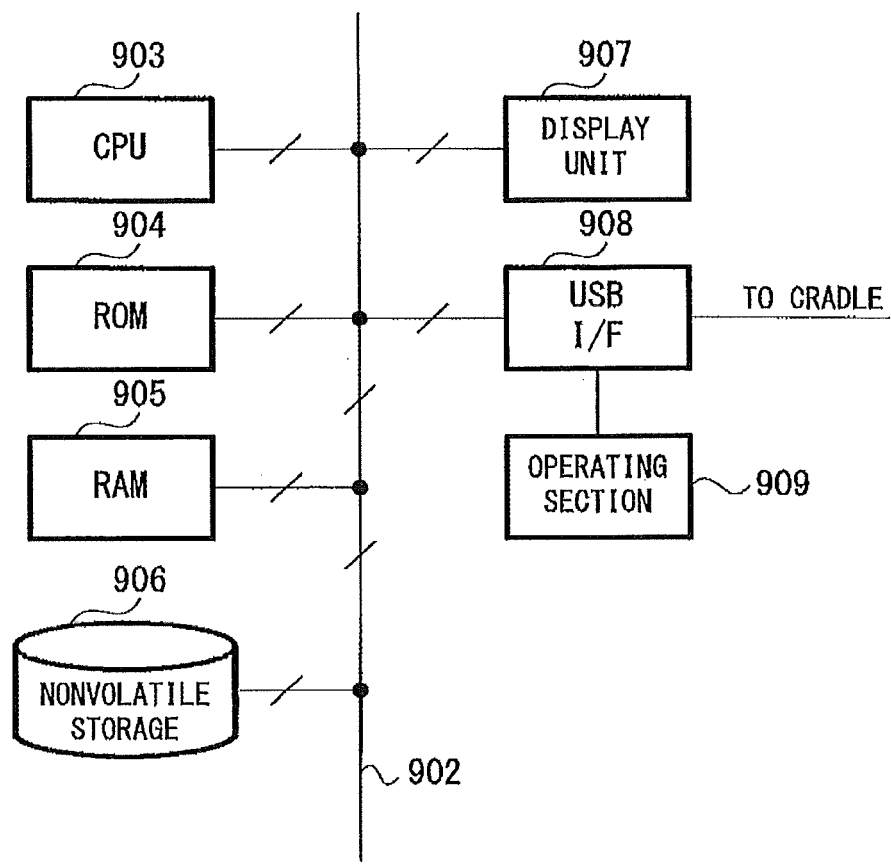
FIG. 9 is a block diagram showing the measurement data management device.

FIG. 9 is a block diagram showing the measurement data management device 104.

As described above, the measurement data management device 104 is actually a known personal computer.

A bus 902 is provided inside the measurement data management device 104. A CPU 903, a ROM 904, a RAM 905, a nonvolatile storage (such as a hard disk device or the like) 906, a display unit (such as a LCD or the like) 907 and a USB interface (I/F) 908 are connected to the bus 902. In addition to an operating section (such as a keyboard, a mouse and/or the like) 909, the cradle 103 is connected to the USB interface 908.

[Software: Blood Glucose Meter 102]

Figure 10:
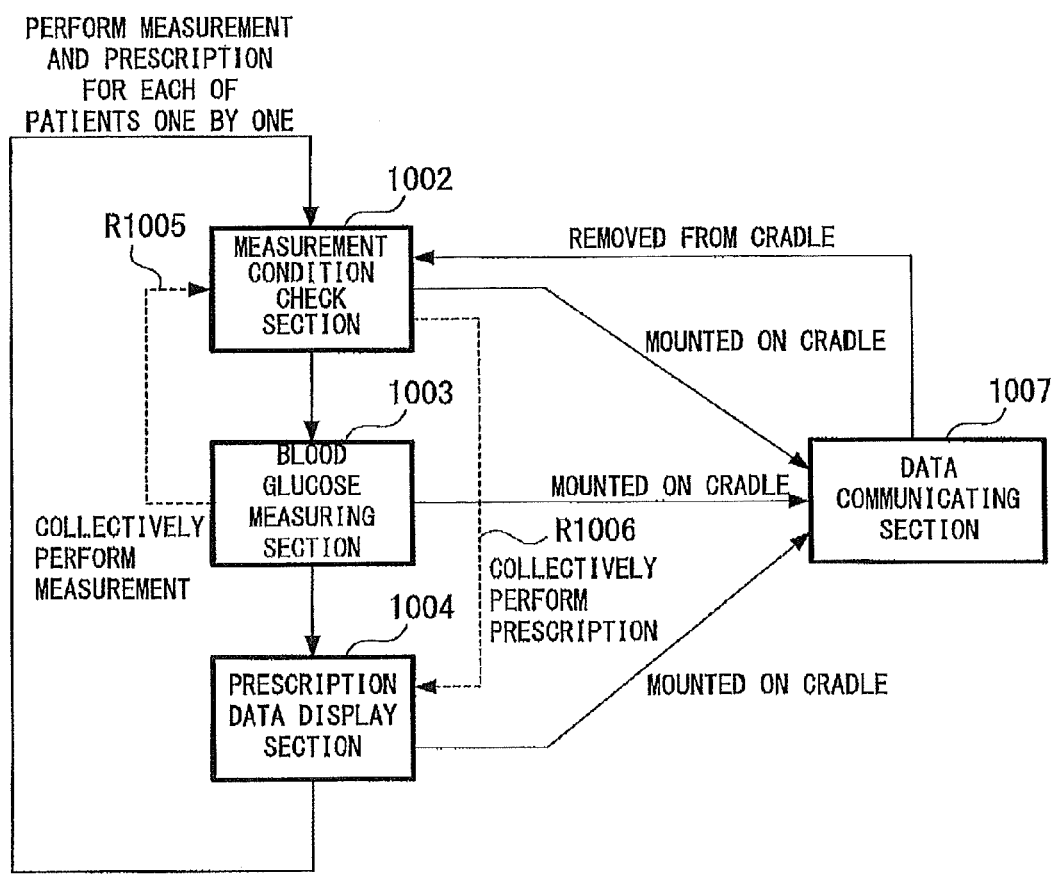
FIG. 10 is a schematic view showing the functions of the blood glucose meter.

FIG. 10 is a schematic view showing the functions of the blood glucose meter 102. FIG. 10 shows the functions executed by a program stored in the ROM 603 of the microcomputer. Note that FIG. 10 is not a functional block diagram for explaining the details of the functions.

When the microcomputer executes the program, the blood glucose meter 102 is brought into a state capable of performing four functions.

First, the microcomputer causes the blood glucose meter 102 to function as a measurement condition check section 1002 for checking the measurement condition of the blood glucose, together with peripheral devices such as the bar-code reader 208 and the like.

Next, the microcomputer causes the blood glucose meter 102 to function as a blood glucose measuring section 1003 for actually measuring the blood glucose, together with peripheral devices such as the optical measuring section 202 and the like.

Finally, the microcomputer causes the blood glucose meter 102 to function as a prescription data display section 1004 for displaying prescription data obtained based on the measured blood glucose level.

In the case where the blood glucose measurement is performed for each of patients one by one and the insulin prescription is performed for each of patients one by one, the aforesaid function states are repeated.

In addition to the aforesaid operation procedure, the blood glucose meter 102 according to the present embodiment may also operate in accordance with an operation procedure in which the blood glucose measurement is collectively performed for each of patients, and thereafter the insulin prescription is collectively performed for each of patients. Such procedure is shown as a flow indicated by arrows R1005 and R1006 of the dotted line of FIG. 10.

In any one of the aforesaid three function states, the microcomputer causes the blood glucose meter 102 to function as a data communicating section 1007 as soon as the blood glucose meter 102 is mounted on the cradle 103, so that it is possible to transfer data files between the blood glucose meter 102 and the measurement data management device 104.

Incidentally, FIG. 10 may also be viewed as a state transition diagram showing operation state of the blood glucose meter 102, as well as a functional block diagram. To be specific:

When functioning as the measurement condition check section 1002, the blood glucose meter 102 displays a message "measurement condition check state";

When functioning as the blood glucose measuring section 1003, the blood glucose meter 102 displays a message "blood glucose measurement state";

When functioning as the prescription data display section 1004, the blood glucose meter 102 displays a message "prescription data display state"; and When functioning as the data communicating section 1007, the blood glucose meter 102 displays a message "data communication state".

FIGS. 11, 12, 13A, 13B, 14 and 15 are block diagrams showing the functions achieved by executing the program stored in the ROM 603 of the microcomputer.

Figure 11:
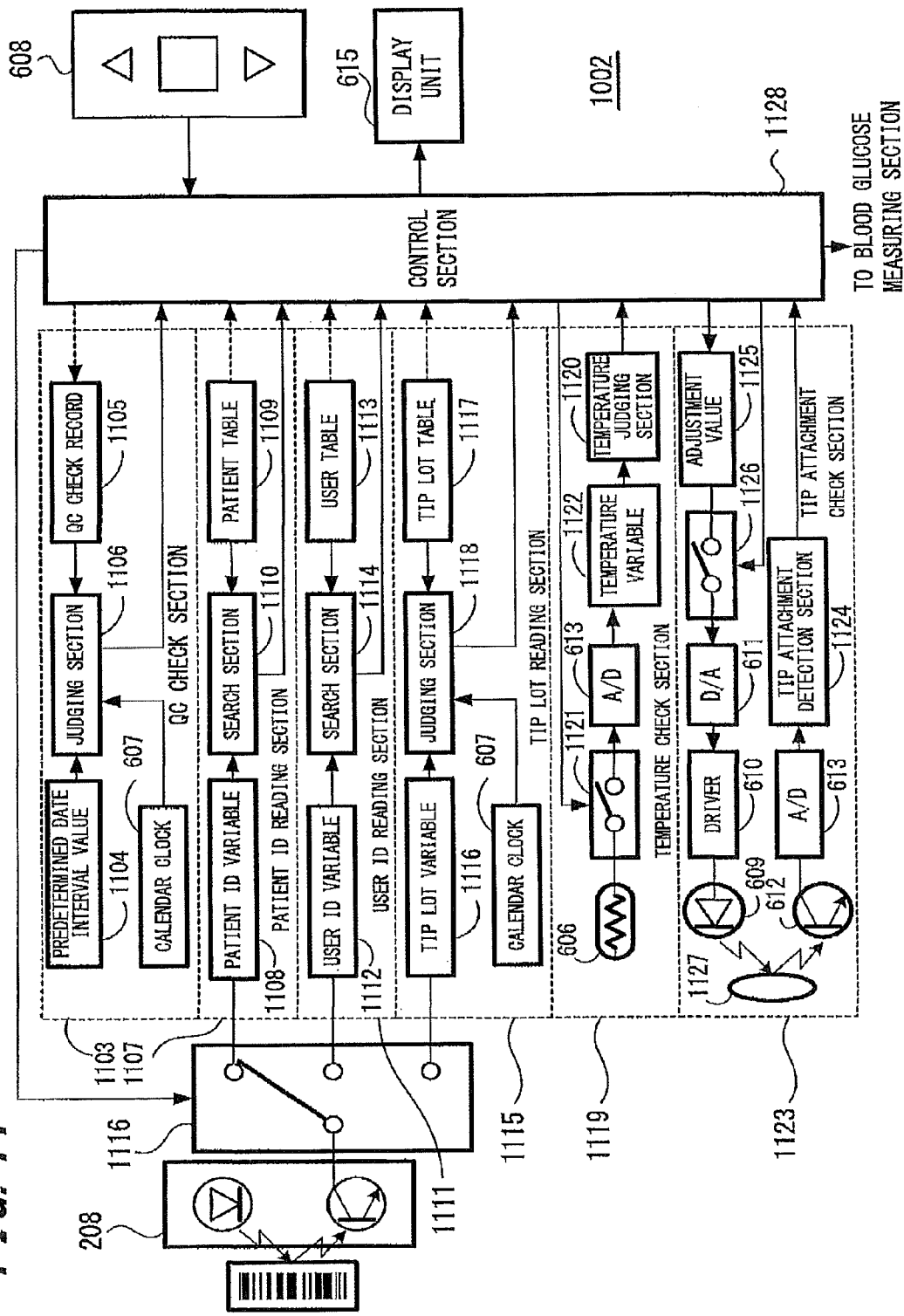
FIG. 11 is a functional block diagram showing a measurement condition check section.

FIG. 11 is a functional block diagram showing the measurement condition check section 1002.

The measurement condition check section 1002 sequentially checks six measurement conditions.

A QC check section 1103 checks whether or not a QC check of the blood glucose meter 102 is normally completed within a predetermined period.

The QC check is a process to be periodically executed mainly in order to maintain blood glucose measurement accuracy. To be more specific, the concrete purpose of the QC check is adjusting the light-emitting intensity of the light-emitting diode 609 and amplification gain of the phototransistor 612 of the optical measuring section 202. The concrete operation steps of the QC check includes: attaching an adjustment tip instead of the measuring tip 212, causing the adjustment tip to soak an adjustment reagent, and performing adjustment so that the light-emitting diode 609 obtains a suitable light-emitting intensity.

A predetermined date interval value 1104 is a text file stored in the nonvolatile storage 614, and a date interval of QC check is recorded in the predetermined date interval value 1104, wherein the date interval of QC check is set by the nurse or the like when he or she performs a set-up procedure of the system.

A QC check record 1105 is a text file stored in the nonvolatile storage 614, and the date and time when the last QC check was performed is recorded in the QC check record 1105.

A judging section 1106 compares the record of the QC check record 1105 with a current date and time obtained from the calendar clock 607 to judge whether or not the QC check has been performed within the date interval of QC check recorded in the predetermined date interval value 1104. For example, in the case where "one week" is set for the predetermined date interval value 1104, if the QC check is not performed for seven days or longer, the judging section 1106 will give a warn.

A patient ID reading section 1107 reads a patient ID with The bar-code reader 208, and searches the patient table 1109 with a search section 1110 to see whether or not the patient ID exists in the patient table 1109.

The read patient ID is stored in a patient ID variable 1108.

A user ID reading section 1111 reads a user ID with the bar-code reader 208, and searches the user table 1113 with a search section 1114 to see whether or not the user ID exists in the user table 1113.

The read user ID is stored in a user ID variable 1112.

A tip lot reading section 1115 reads a tip lot (a lot number of the measuring tip) of the measuring tip 212 attached to the optical measuring section 202 with the bar-code reader 208, and judges, with a judging section 1118, whether or not the tip lot exists in tip lot table 1117 and whether or not the measuring tip 212 is within the validity date.

The read tip lot is stored in a tip lot variable 1116.

Incidentally, the patient ID reading section 1107, the user ID reading section 1111 and the tip lot reading section 1115 share the bar-code reader 208 through a switch 1116.

A temperature check section 1119 measures the temperature with the thermistor 606, converts the measured result into digital data, and then judges whether or not the temperature data is within an allowable range with a temperature judging section 1120.

The temperature data obtained by performing the measurement is stored in a temperature variable 1122.

After the measuring tip 212 is attached, a tip attachment check section 1123 judges whether or not the attached measuring tip 212 is deemed a new one.

The light-emitting intensity stored in an adjustment value (which is a text file) 1125 stored in the nonvolatile storage 614 is converted into an analog voltage signal by the D/A converter 611 and then power-amplified by the driver 610 to drive the light-emitting diode 609 to emit light. Further, the light of the light-emitting diode 609 is irradiated to a test piece 1127 inside the measuring tip 212, the light reflected from the measuring tip 212 is signal-converted by the phototransistor 612, the result is converted into digital data by the A/D converter 613, and then a tip attachment detection section 1124 judges whether or not a new measuring tip 212 has been normally attached.

A control section 1128 sequentially causes the QC check section 1103, the patient ID reading section 1107, the user ID reading section 1111, the tip lot reading section 1115, the temperature check section 1119 and the tip attachment check section 1123 to operate, and obtains execution results of these sections. Therefore, the control section 1128 controls the switch 1116, a switch 1121 and a switch 1126.

Further, the control section 1128 receives the operations of the user with the operating section 608, and displays various execution results on the display unit 615.

Figure 12:
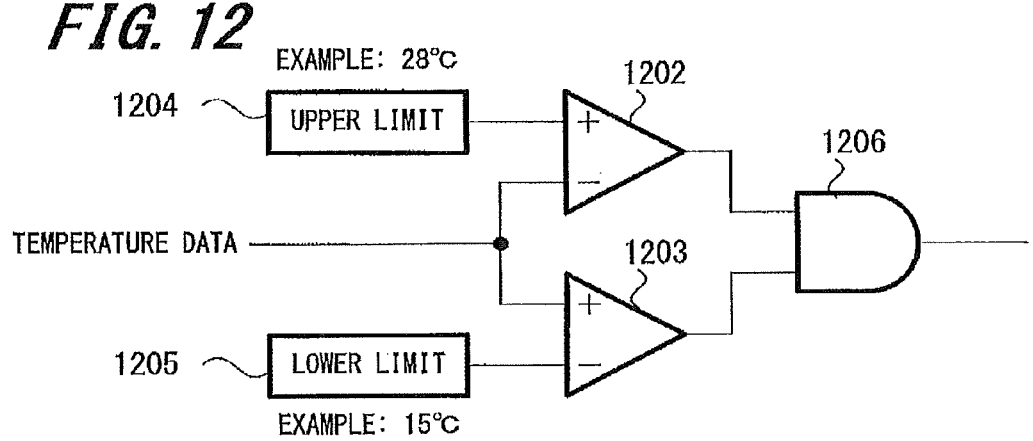
FIG. 12 is a functional block diagram showing a temperature judging section.

FIG. 12 is a functional block diagram showing the temperature judging section 1120.

The temperature data obtained from the thermistor 606 through the A/D converter 613 is inputted to two comparators 1202 and 1203, and whether or not the temperature data falls in a range between an upper limit 1204 and a lower limit 1205 is judged as an output of an AND gate 1206.

Figure 13A:
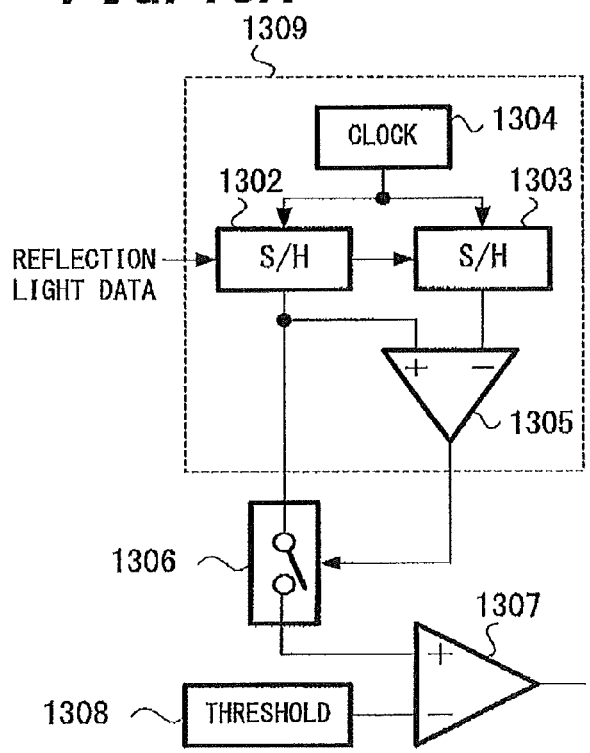
FIG. 13A is a functional block diagram showing a tip attachment detection section and FIG. 13B is a graph for explaining a mechanism for determining whether or not a measuring tip has been attached and whether or not the measuring tip is a non-defective product.
Figure 13B:
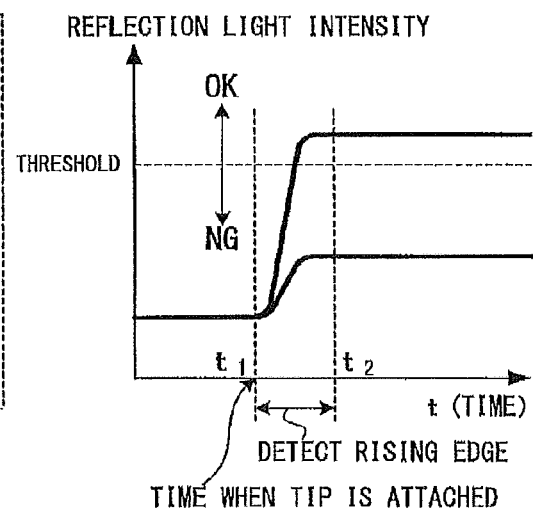

FIG. 13A is a functional block diagram showing the tip attachment detection section 1124, and FIG. 13B is a graph for explaining a mechanism for determining whether or not the measuring tip 212 has been attached and whether or not the measuring tip 212 is a non-defective product.

The reflected light data obtained from the measuring tip 212 through the A/D converter 613 is held by two sample-and-hold circuits 1302 and 1303. The holding timings are controlled by a clock 1304. In other words, the sample-and-hold circuit 1302 and the sample-and-hold circuit 1303 respectively hold values obtained at timings shifted by one sample clock.

The value of the sample-and-hold circuit 1302 and the value of the sample-and-hold circuit 1303 are compared with each other by a comparator 1305.

The sample-and-hold circuit 1302, the sample-and-hold circuits 1303, the clock 1304 and the comparator 1305 constitute a rising edge detection section 1309 for detecting a rising edge of the reflected light data.

When the value of the reflected light data rises, the comparator 1305 indicates positive. In response to this, a switch 1306 is controlled to turn on.

The value of the sample-and-hold circuit 1302 at this time is compared with a threshold 1308 by a comparator 1307 to judge whether or not the reflection light intensity is sufficient.

Operation for judging whether or not the measuring tip 212 has been attached and whether or not the measuring Lip 212 is a non-defective product will be described below with reference to FIG. 13B.

Supposing that a nurse has attached a used measuring tip 212 by mistake, since the test piece inside the measuring tip 212 had been reacted and therefore has a reduced reflectance, the reflection light intensity will be lower than the threshold.

First, the reflection light intensity value is obtained respectively at time t1 and time t2, and the rising edge of the reflection light intensity is detected by comparing the obtained values. This is the function of the rising edge detection section 1309.

Next, the reflection light intensity value obtained at time t2 is compared with the threshold to confirm that a new measuring tip 212 has been attached. This is the function of the comparator 1307.

Figure 14:
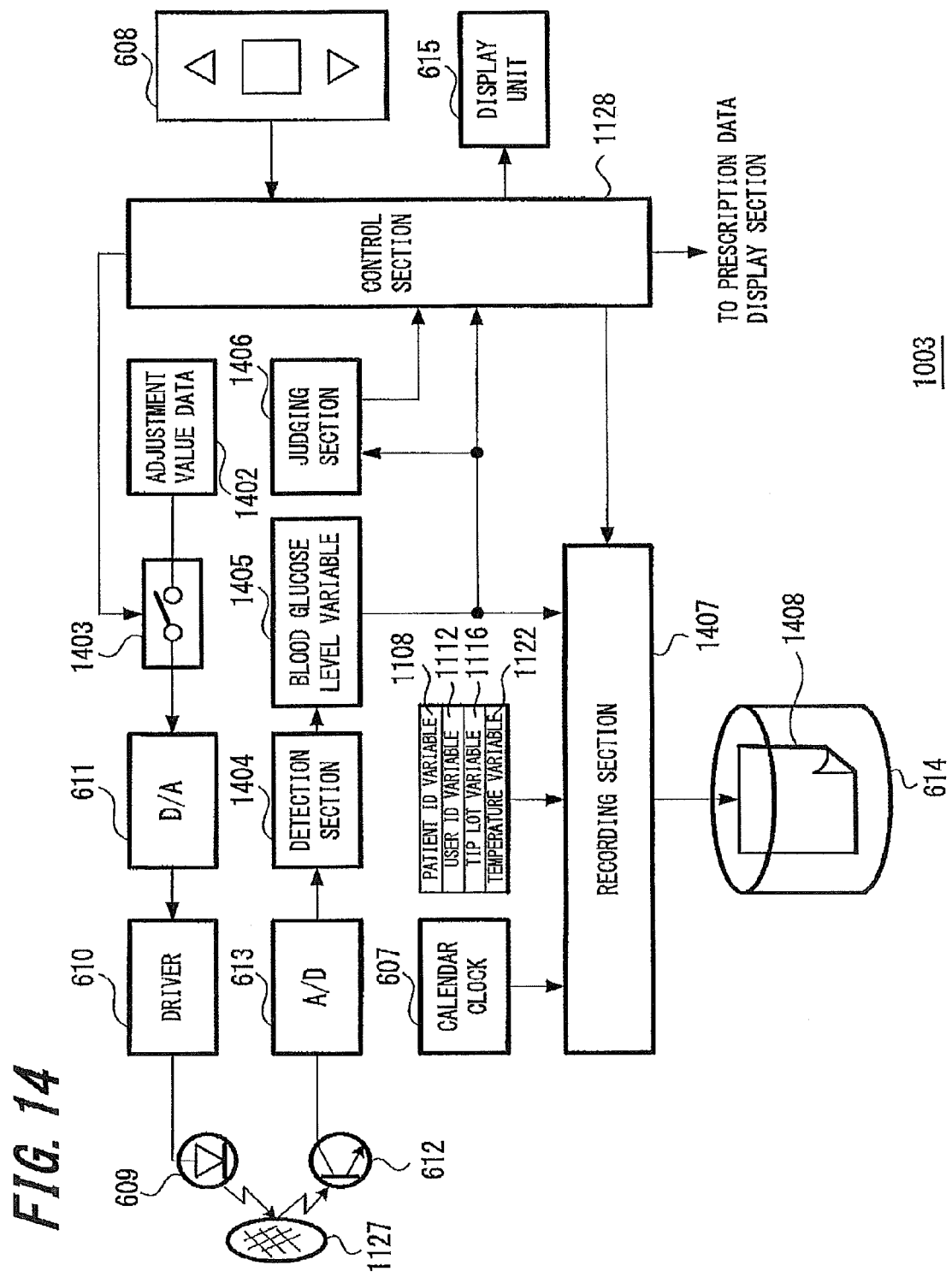
FIG. 14 is a functional block diagram showing a blood glucose measuring section.

FIG. 14 is a functional block diagram showing the blood glucose measuring section 1003.

An adjustment value data 1402 stored in the nonvolatile storage 614 is supplied, through a switch 1403, to the D/A converter 611 where the data is converted into an analog voltage signal. The analog voltage signal drives the driver 610, which is a power amplifier, to control the light-emitting intensity of the light-emitting diode 609.

The light emitted by the light-emitting diode 609 is irradiated to the test piece 1127 provided inside the measuring tip 212. The phototransistor 612 of the optical measuring section 202 receives the light reflected from the test piece 1127, and converts the reflected light into a voltage signal.

The voltage signal obtained from the phototransistor 612 is converted into a digital value by the A/D converter 613. A detection section 1404 verifies the digital value and performs a predetermined arithmetic process to convert the digital value into a blood glucose level.

The blood glucose level is stored in a blood glucose level variable 1405 provided in the RAM 604.

A judging section 1406 verifies whether the value of the blood glucose level variable 1405 is extremely large or extremely small. Further, the value of the blood glucose level variable 1405 is supplied to the control section 1128 to be used to display the blood glucose level on the display unit 615. At this time, the judgment result of the judging section 1406 is reflected by the display content of the display unit 615.

A recording section 1407 records the following data in the measurement/prescription results table 1408 stored in the nonvolatile storage 614 in a predetermined format: the current date and time data obtained from the calendar clock 607, the patient ID variable 1108, the user ID variable 1112, the tip lot variable 1116, the temperature variable 1122 and the blood glucose level variable 1405, wherein the patient ID variable 1108, the user ID variable 1112, the tip lot variable 1116, the temperature variable 1122 had been previously obtained by the measurement condition check section 1002.

Figure 15:
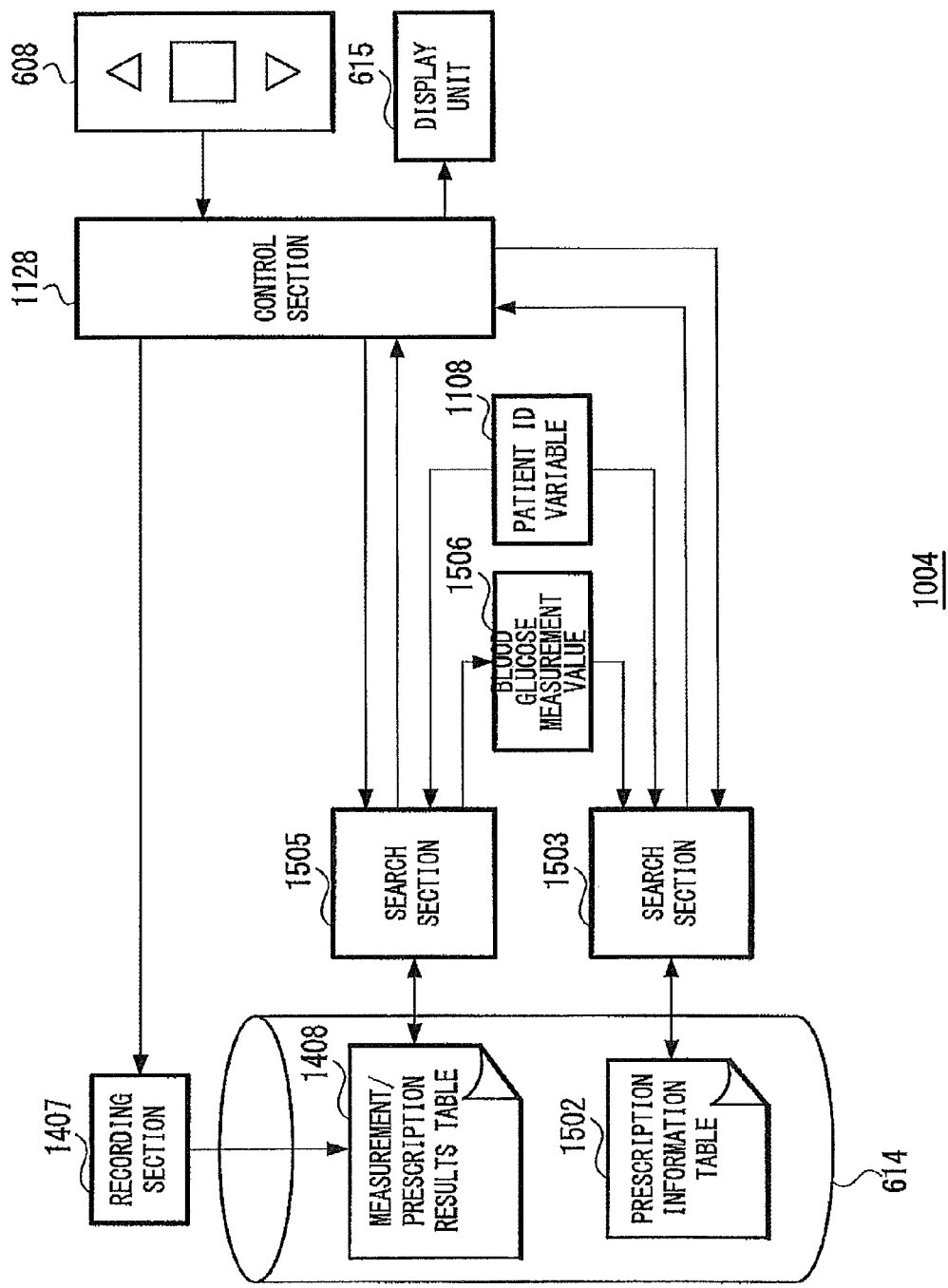
FIG. 15 is a functional block diagram showing a prescription data display section.

FIG. 15 is a functional block diagram showing the prescription data display section 804.

The control section 1128 controls a search section 1505 to read out the recorded blood glucose level data from the measurement/prescription results table 1408.

Using the patient ID variable 1108 as a search key, the search section 1505 reads out the blood glucose level data of the patient recorded in the measurement/prescription results table 1408 by the blood glucose measuring section 1003, and writes the blood glucose level data to a blood glucose measurement value 1506, which is a temporary variable.

The control section 1128 controls a search section 1503 to read out the prescription data from the prescription information table 1502 stored in the nonvolatile storage 614.

Using the patient ID variable 1108 and the blood glucose measurement value 1506 as search keys, the search section 1503 reads out the prescription data of the patient (namely, insulin dosage and drug name) stored in the prescription information table 1502, and transfers the prescription data to the control section 1128.

The drug name and the insulin dosage obtained through the search section 1503 are displayed on the display unit 615 through the control section 1128.

After displaying the prescription data on the display unit 615, the control section 1128 controls the recording section 1407 to record the prescription data (the insulin dosage and drug name) in a record of the patient in the measurement/prescription results table 1408, and rewrites an insulin administration confirmation flag.

The details about the recording section 1407 will be described later with reference to FIGS. 16A to 16C.

[Various Tables: Blood Glucose Meter 102]

The main tables stored in the blood glucose meter 102 or to be made will be described below.

FIGS. 16A to 16C are schematic views showing tables stored in the blood glucose meter 102.

FIG. 16A is a list of the fields of the measurement/prescription table 1602.

The measurement/prescription table 1602 is transmitted from the measurement data management device 104 to the blood glucose meter 102, and an instruction on blood glucose measurement procedure and/or an instruction on insulin administration procedure are recorded on the measurement/prescription table 1602.

A number for uniquely identifying the patient is stored in a "PATIENT ID" field.

A scheduled measurement time created by the measurement data management device 104 is stored in a "SCHEDULED MEASUREMENT TIME" field. The scheduled measurement time is used as a search key for identifying whether or not the blood glucose measurement should be performed and identifying the number of prescriptions in the measurement data management device 104 when transmitting data to the measurement data management device 104.

A flag indicating an instruction on whether the blood glucose should be measured is stored in a "BLOOD GLUCOSE MEASUREMENT FLAG" field.

A value indicating an instruction on whether insulin (drug) should be administered, and if yes, how many kinds of administration should be performed is stored in a "PRESCRIPTION NUMBER" field.

After the blood glucose of the patient is measured, the number of the kind of the insulin to be administered to the patient is not limited to one. Thus, the blood glucose meter 102 is configured so that up to three kinds of prescriptions can be applied to the patient.

The "PRESCRIPTION NUMBER" field can take different values corresponding to the number of the prescribe drugs from "0", which means the patient only receives blood glucose measurement without receiving any prescription, to "3", which means three kinds of drugs are prescribed to the patient.

FIG. 16B is a list of the fields of the measurement/prescription results table 1408.

The measurement/prescription results table 1408 is a table in which the results of the blood glucose measurement and the contents (execution results) of the insulin administration performed by the blood glucose meter 102 are recorded. The measurement/prescription results table 1408 is in pair relation with the measurement/prescription table 1602 in which the contents (instruction) executed by the blood glucose meter 102 are described.

The date and time when the blood glucose was measured is recorded in a "DATE AND TIME OF MEASUREMENT" field. The date and time is recorded by acquiring the date and time by the calendar clock 607 in the recording section 1407 of the blood glucose measuring section 1003.

Similar to the "PATIENT ID" field of the measurement/prescription table 1602, a number for uniquely identifying the patient is stored in a "PATIENT ID" field of the measurement/prescription results table 1408.

A number for uniquely identifying the user is stored in a "USER ID" field.

A tip lot number is recorded in a "TIP LOT" field.

The temperature when the blood glucose was measured is recorded in a "TEMPERATURE" field.

The patient ID variable 1108, the user ID variable 1112, the tip lot variable 1116 and the temperature variable 1122, each being obtained by the measurement condition check section 1002, are respectively recorded in a "PATIENT ID" field, a "USER ID" field, a "TIP LOT" field and a "TEMPERATURE" field.

A measured blood glucose level is recorded in a "BLOOD GLUCOSE LEVEL" field. To be specific, the content of the blood glucose level variable 1405 obtained by the blood glucose measuring section 1003 is recorded.

A flag indicating whether or not the blood glucose has been measured is recorded in a "BLOOD GLUCOSE MEASUREMENT FLAG" field.

Similar to the "SCHEDULED MEASUREMENT TIME" field of the measurement/prescription table 1602, a scheduled measurement time created by the measurement data management device 104 is stored in a "SCHEDULED MEASUREMENT TIME" field of the measurement/prescription results table 1408. In other words, the content of the "SCHEDULED MEASUREMENT TIME" field of the measurement/prescription results table 1408 is copied from the "SCHEDULED MEASUREMENT TIME" field of the measurement/prescription table 1602.

Similar to the "PRESCRIPTION NUMBER" field of the measurement/prescription table 1602, a value indicating an instruction on whether the insulin should be administered, and if yes, how many kinds of administration should be performed is stored in a "NUMBER OF INSULIN ADMINISTRATIONS" field. In other words, the content of the "NUMBER OF INSULIN ADMINISTRATIONS" field of the measurement/prescription results table 1408 is copied from the "PRESCRIPTION NUMBER" field of the measurement/prescription table 1602.

An "INSULIN ADMINISTRATION INFORMATION" field consists of four fields, which are a "DRUG NAME" field, an "INSULIN DOSAGE" field, an "INSULIN DOSAGE DISPLAY FLAG" field and an "INSULIN ADMINISTRATION CONFIRMATION FLAG" field, and is a variable-length field having a plurality of records, wherein the number of the records is equal to the number indicated in the "NUMBER OF INSULIN ADMINISTRATIONS" field.

A drug name of insulin is recorded in a "DRUG NAME" field.

An insulin dosage obtained by referring to the prescription information table 1502 based on the measured blood glucose level is stored in the "INSULIN DOSAGE" field. To be specific, the content of the prescription data, which is acquired by the search section 1503 in the prescription data display section 804 and recorded by the control section 1128 when displaying the prescription data on the display unit 615, is recorded in the "INSULIN DOSAGE" field.

A flag indicating whether or not the insulin dosage has been displayed on the display unit is recorded in the "INSULIN DOSAGE DISPLAY FLAG" field.

A flag indicating whether or not the insulin has been administered is recorded in the "INSULIN ADMINISTRATION CONFIRMATION FLAG" field.

As mentioned above when describing the "PRESCRIPTION NUMBER" field of the measurement/prescription table 1602, the "NUMBER OF INSULIN ADMINISTRATIONS" field can also take different values from "0" to "3".

If the "NUMBER OF INSULIN ADMINISTRATIONS" field is "0", the "INSULIN ADMINISTRATION INFORMATION" field itself does not exist.

If the "NUMBER OF INSULIN ADMINISTRATIONS" field is "1", there will be one record in the "INSULIN ADMINISTRATION INFORMATION" field, the record consisting of four fields which are a "DRUG NAME" field, an "INSULIN DOSAGE" field, an "INSULIN DOSAGE DISPLAY FLAG" field and an "INSULIN ADMINISTRATION CONFIRMATION FLAG" field.

Similarly, if the "NUMBER OF INSULIN ADMINISTRATIONS" field is "2", there will be two records in the "INSULIN ADMINISTRATION INFORMATION" field, and if the "NUMBER OF INSULIN ADMINISTRATIONS" field is "3", there will be three records in the "INSULIN ADMINISTRATION INFORMATION" field.

The prescription result for one patient is recorded in one record of the measurement/prescription results table 1408. Thus, there are up to three insulin dosage display flags and up to three insulin administration confirmation flags existed in one record respectively for each kind of drugs to be administered to the patient.

Upon receiving the measurement/prescription table 1602 from the measurement data management device 104, the blood glucose meter 102 once stores the measurement/prescription table 1602 in the nonvolatile storage 614.

Next, based on the contents described in the measurement/prescription table 1602, the blood glucose meter 102 creates the measurement/prescription results table 1408 in the nonvolatile storage 614.

First, the "PATIENT ID" field and the "SCHEDULED MEASUREMENT TIME" field of the measurement/prescription results table 1408 are copied from the "PATIENT ID" field and the "SCHEDULED MEASUREMENT TIME" field of the measurement/prescription table 1602.

Next, if the blood glucose measurement flag of the measurement/prescription table 1602 is "true", the blood glucose measurement flag of the measurement/prescription results table 1408 will be set to "false".

Inversely, if the blood glucose measurement flag of the measurement/prescription table 1602 is "false", the blood glucose measurement flag of the measurement/prescription results table 1408 will be set to "true".

Next, the number of prescriptions of the measurement/prescription table 1602 is copied to the number of insulin administrations of the measurement/prescription results table 1408.

Further, in response to the number of prescriptions of the measurement/prescription table 1602, a plurality of records are created in the "INSULIN ADMINISTRATION INFORMATION" field of the measurement/prescription results table 1408, the number of the records is equal to the number of prescriptions of the measurement/prescription table 1602. At this time, initial value of both the insulin dosage display flag and the insulin administration confirmation flag is set to "false".

By performing the aforesaid process for all records of the measurement/prescription table 1602, a plurality of records are created in the measurement/prescription results table 1408, wherein the number of the records is equal to the number of those of the measurement/prescription table 1602.

FIG. 16C shows an example of the records recorded in the prescription information table 1502.

The prescription information table 1502 is a table in which instruction information on dosage of insulin according to some known sliding scale is recorded. The prescription information table 1502 is a table in which the blood glucose level range and the insulin dosage corresponding to the blood glucose level range correspond each other.

There are a plurality of records of one patient ID in the "PATIENT ID" field. At least any one of a "CLASSIFICATION NUMBER" field, a "BLOOD GLUCOSE LEVEL RANGE" field, a "DRUG NAME" field and a "PRESCRIPTION" field of these records have different values.

The "CLASSIFICATION NUMBER" field corresponds to the kind of the drugs, and has the minimum value of "1" and the maximum value of "3". The value of the "CLASSIFICATION NUMBER" field and the "DRUG NAME" field correspond one-to-one with each other.

In an example shown in FIG. 16C, a patient having patient ID "123456" has nine records whose classification numbers are "1". Which means one kind of drug is administered to the patient having patient ID "123456", and there are nine insulin prescriptions corresponding to different blood glucose levels.

In the case of a patient having patient ID "135792", there are two classification numbers of "1" and "2". In other words, two kinds of drugs are administered to the patient having patient ID "135792".

The blood glucose measurement procedure, and insulin prescription procedure are generally performed at a predetermined time after the patient having meal. Further, the blood glucose measurement procedure and insulin prescription procedure may also be performed at a predetermined time before the patient having meal. The blood glucose measurement procedure and insulin prescription procedure are collectively performed for a plurality of patients at a predetermined time.

The work unit of the blood glucose measurement procedure and/or insulin prescription procedure collectively performed for a plurality of patients at a predetermined time is "round". For example, the expression of "one round in 30 minutes after breakfast" and the like are used in practice.

In order to prevent mistake in the blood glucose measurement procedure, the insulin prescription procedure and the like, the measurement data management device 104 only transmits data for performing one round to the blood glucose meter 102.

Further, after the round is completed, the measurement/prescription results table 1408 is transmitted from the blood glucose meter 102 to the measurement data management device 104 as soon as the blood glucose meter 102 is mounted on the cradle 103. Upon receiving the measurement/prescription results table 1408, the measurement data management device 104 records the measurement/prescription results table 1408 in a patient history table (not shown in the drawings) inside thereof.

Other tables than the measurement/prescription table 1602, the measurement/prescription results table 1408 and the prescription information table 1502 shown in FIGS. 16A, 16B and 16C will be briefly described below.

The patient table 1109 is a table formed by pairing the "PATIENT ID" field with a "PATIENT NAME" field.

The user table 1113 is a table formed by pairing the "USER ID" field with a "USER NAME" field. Incidentally, since the user who performs the measurement does not have to be a nurse, but may also be a doctor, the name of "user" is used in the table.

The tip lot table 1117 is a table formed by pairing a "LOT NUMBER OF MEASURING TIP 212" field with a "VALIDITY DATE" field.

The tables described above may be any format as long as the fields and the records can be clearly recognized. In the case of the blood glucose meter 102 according to the present embodiment, since data amount stored in the nonvolatile storage 614 is small, the tables may also be text files such as comma-delimited files or the like.

[Operation]

Next, the operation of the blood glucose meter 102 will be described below.

Figure 17:
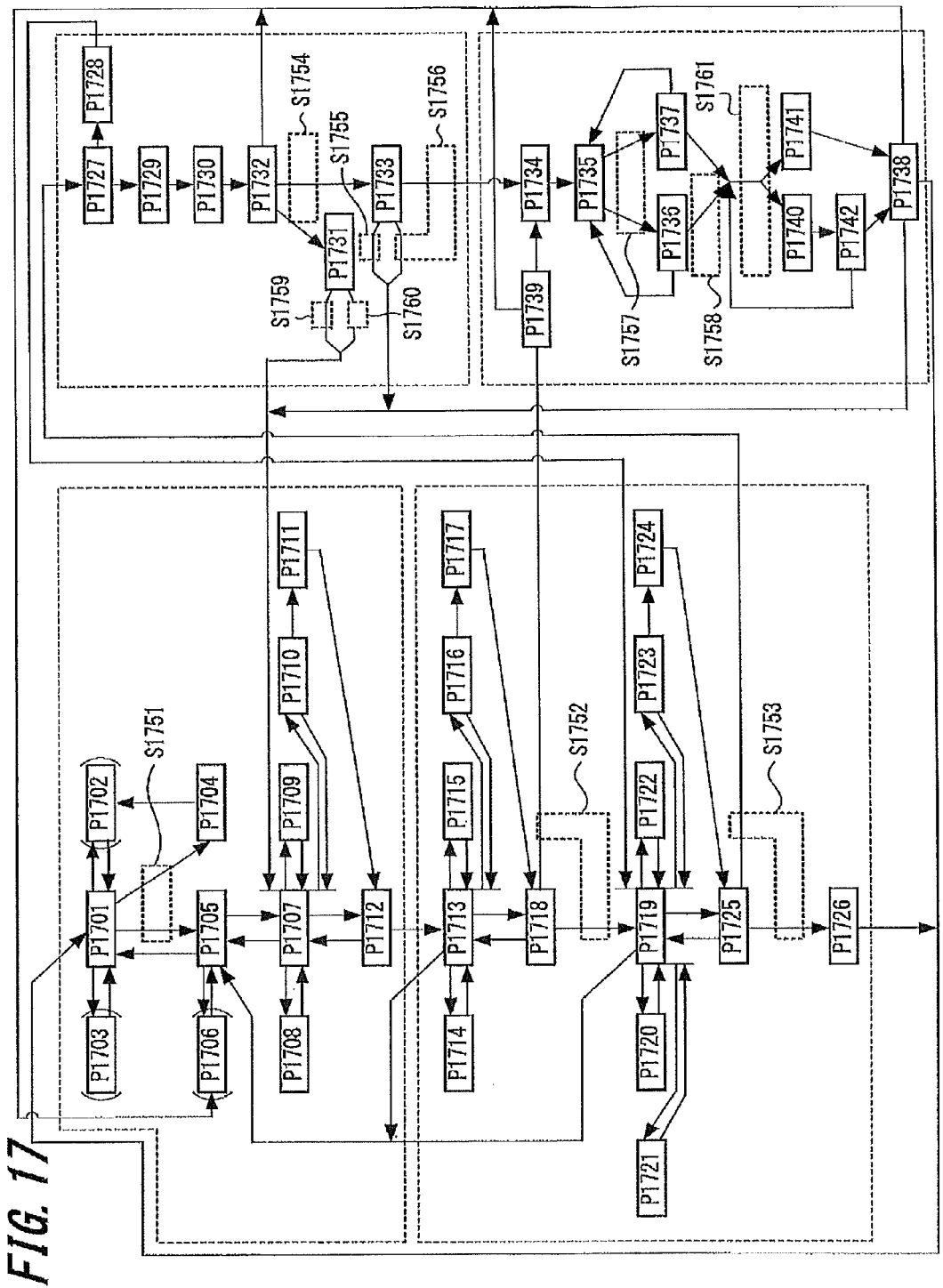
FIG. 17 is a state transition diagram showing screen transition of the blood glucose meter.

FIG. 17 is a state transition diagram showing screen transition of the display unit 615 (LCD 203) of the blood glucose meter 102.

FIG. 18, FIG. 19, FIG. 20 and FIG. 21 are partly enlarged views of the state transition diagram shown in FIG. 17.

FIGS. 22A, 22B, 22C, 23D, 23E, 23F, 24G, 24H, 24I 24J, 25K, 25L, 25M, 25N, 26O, 26P, 26Q, 27R and 27S are schematic views showing nurse's workflow and attendant screen transition of the display unit 615 of the blood glucose meter 102.

Figure 28:
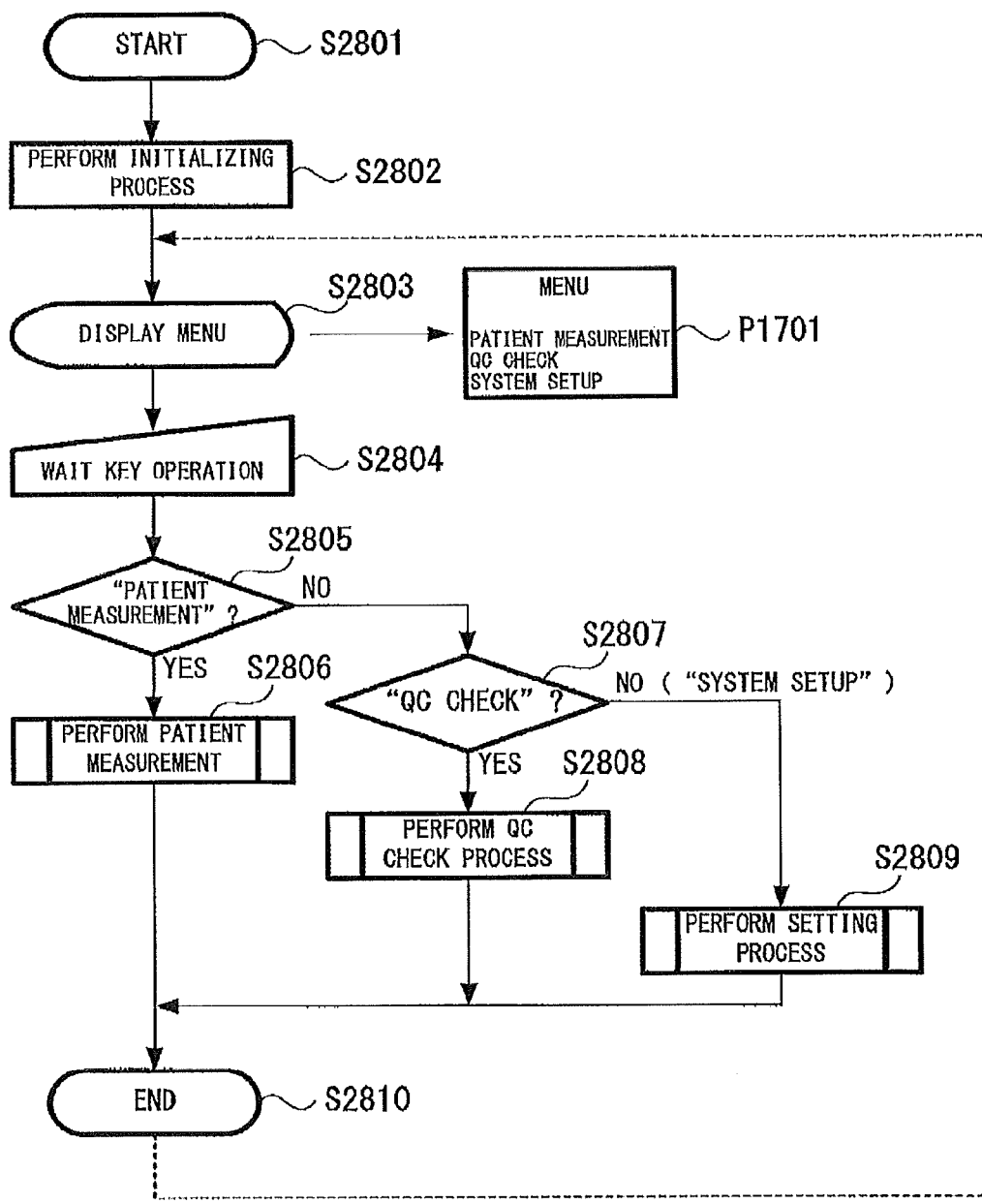
FIG. 28 is a flowchart showing the flow of the overall operation of the blood glucose meter.

FIG. 28 is a flowchart showing the flow of overall operation of the blood glucose meter 102.

Figure 29:
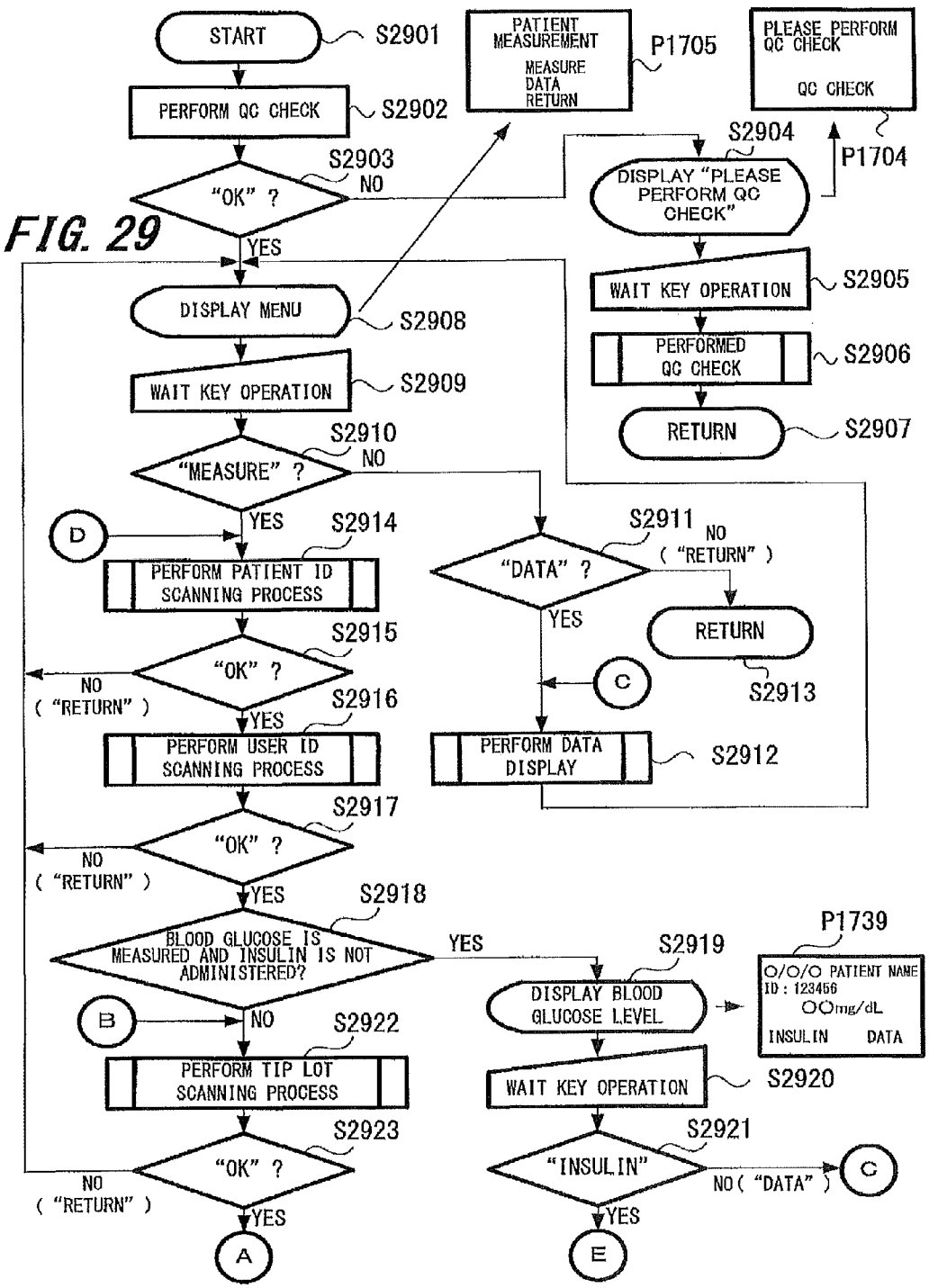
FIG. 29 is a flowchart showing the flow of a measurement process of the blood glucose meter.
Figure 30:
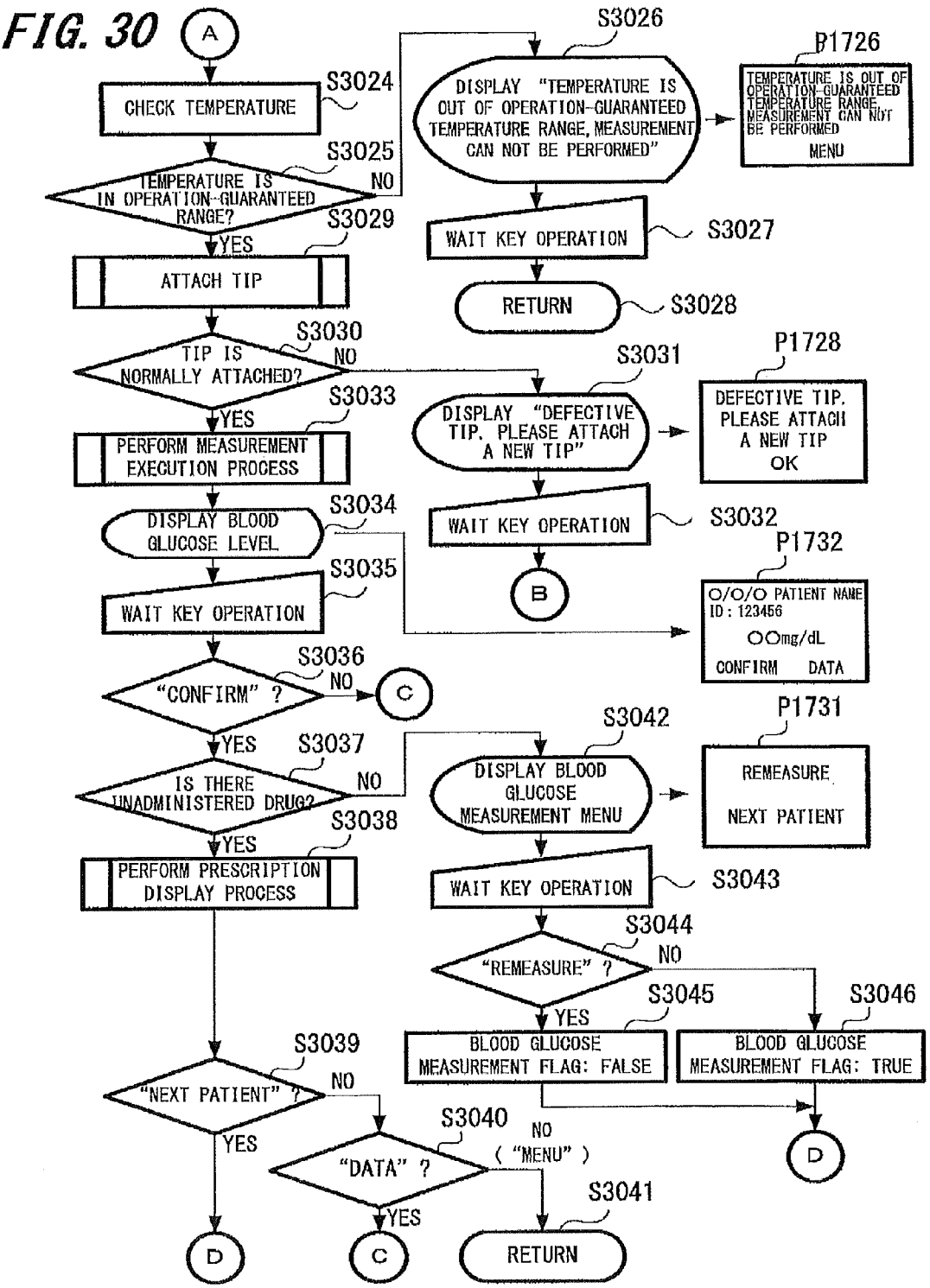
FIG. 30 is a flowchart showing the flow of the measurement process of the blood glucose meter.

FIGS. 29 and 30 are flowcharts showing the flow of overall measurement process of the blood glucose meter 102.

Figure 31:
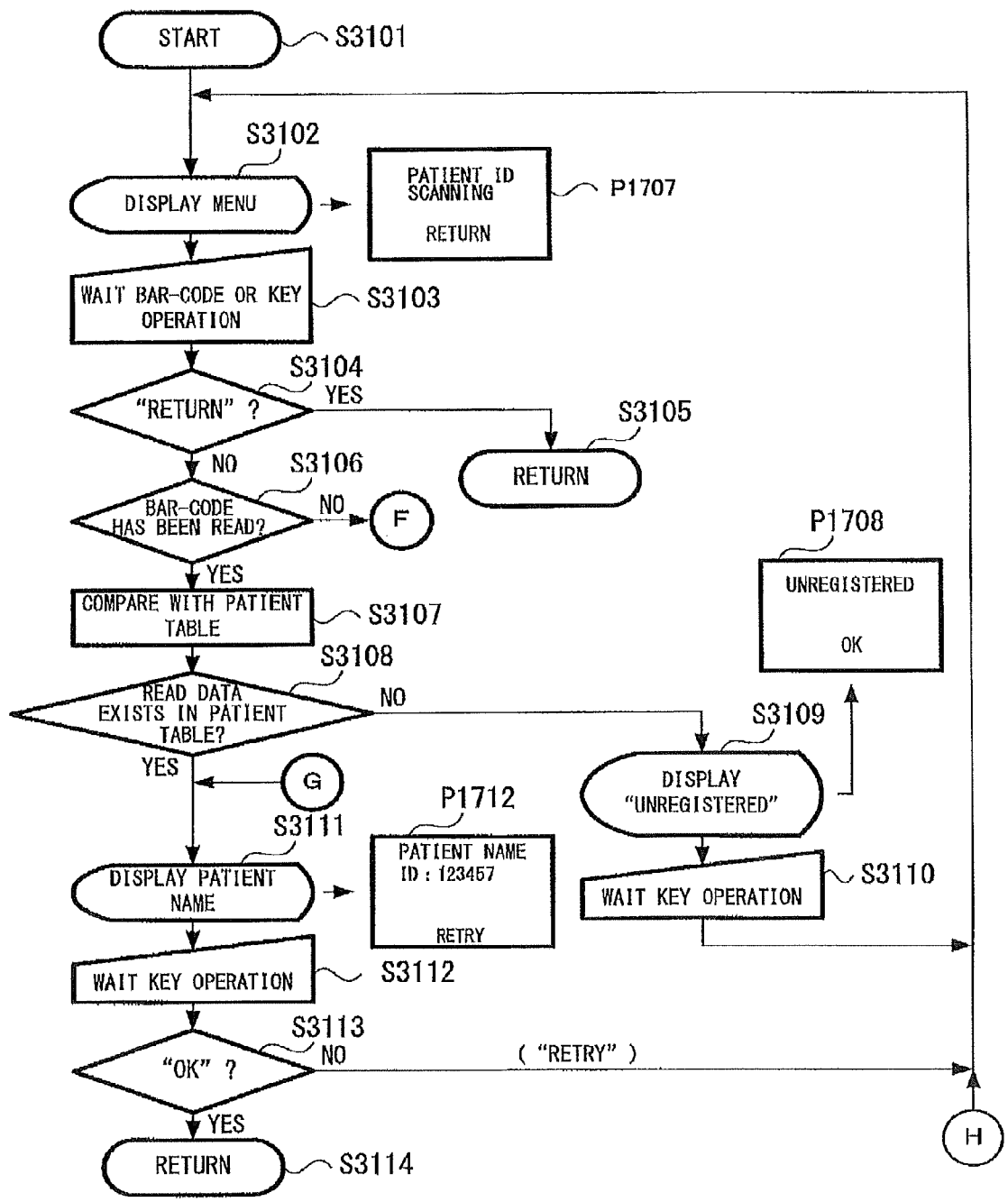
FIG. 31 is a flowchart showing the flow of a patient ID scanning process.
Figure 32:
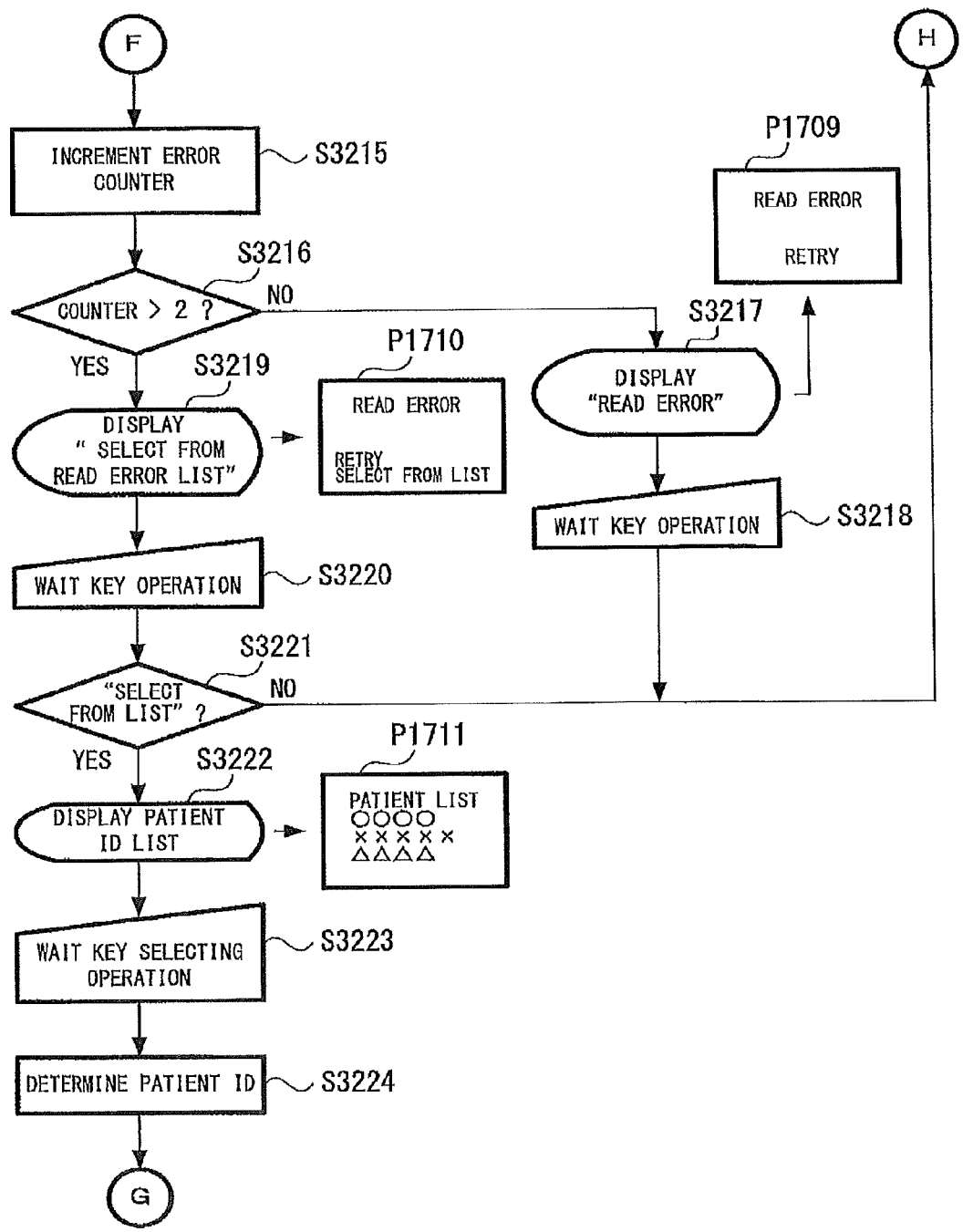
FIG. 32 is a flowchart showing the flow of the patient ID scanning process.

FIGS. 31 and 32 are flowcharts showing the flow of a patient ID scanning process.

Figure 33:
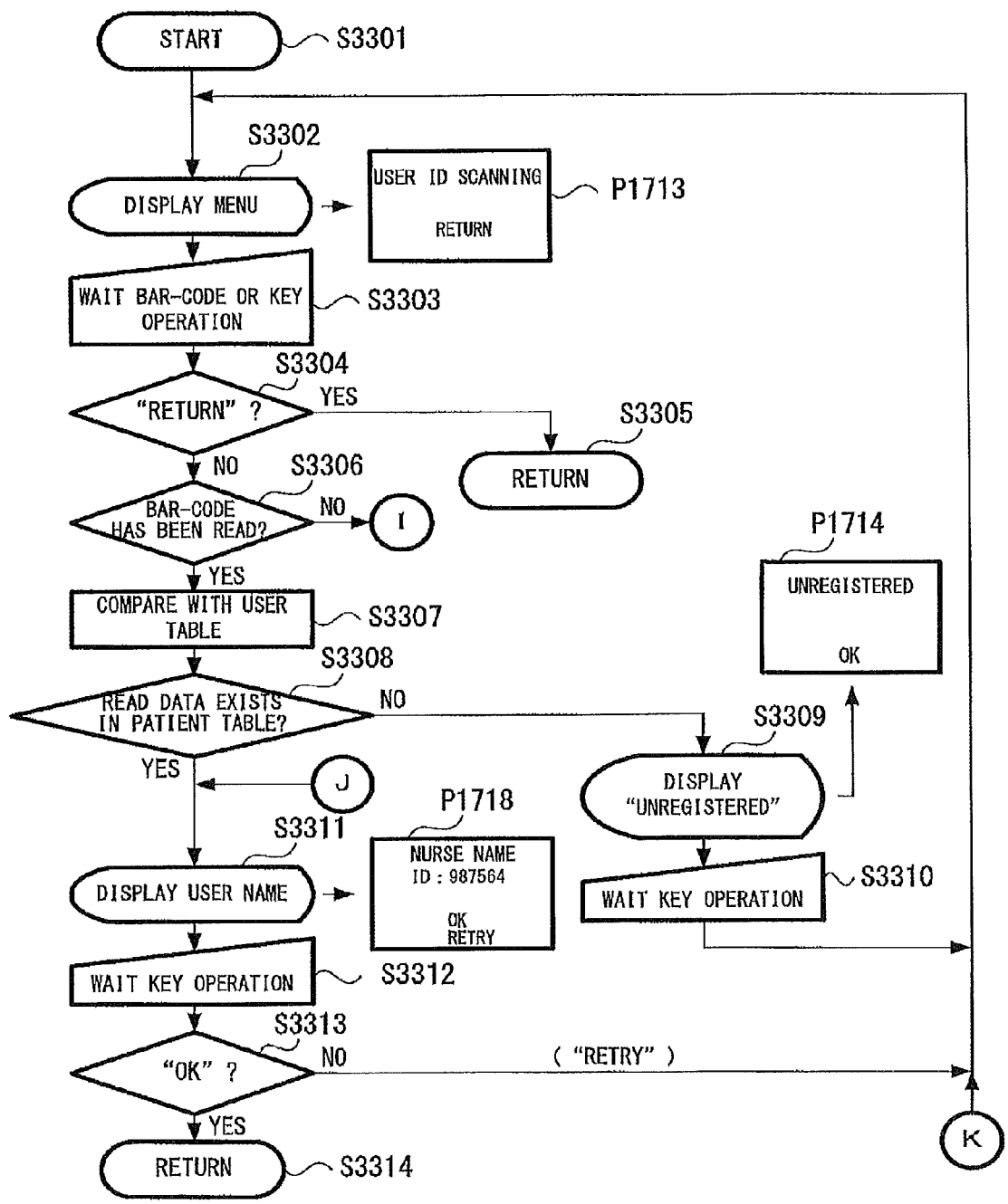
FIG. 33 is a flowchart showing the flow of a user ID scanning process.
Figure 34:
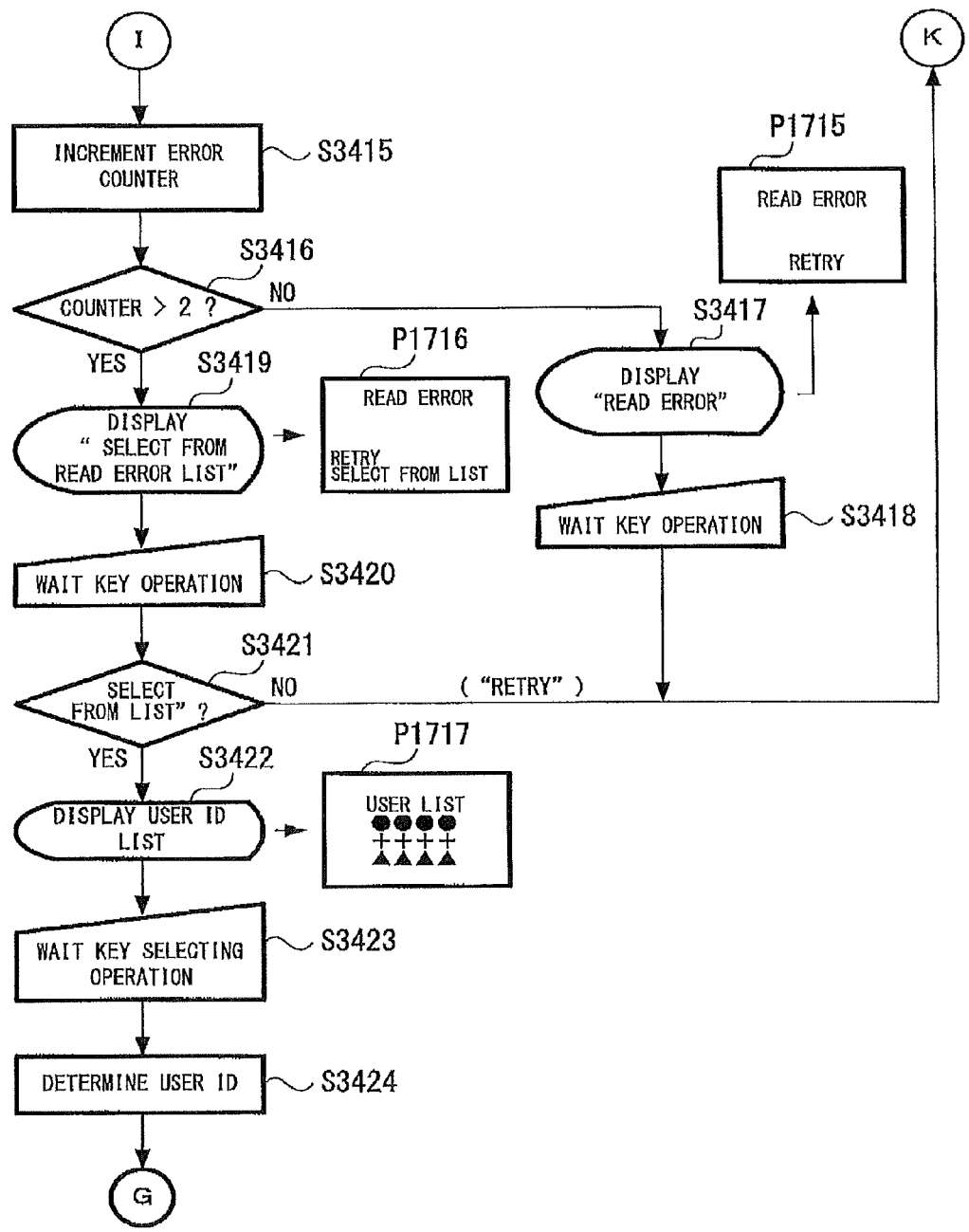
FIG. 34 is a flowchart showing the flow of the user ID scanning process.

FIGS. 33 and 34 are flowcharts showing the flow of a user ID scanning process.

Figure 35:
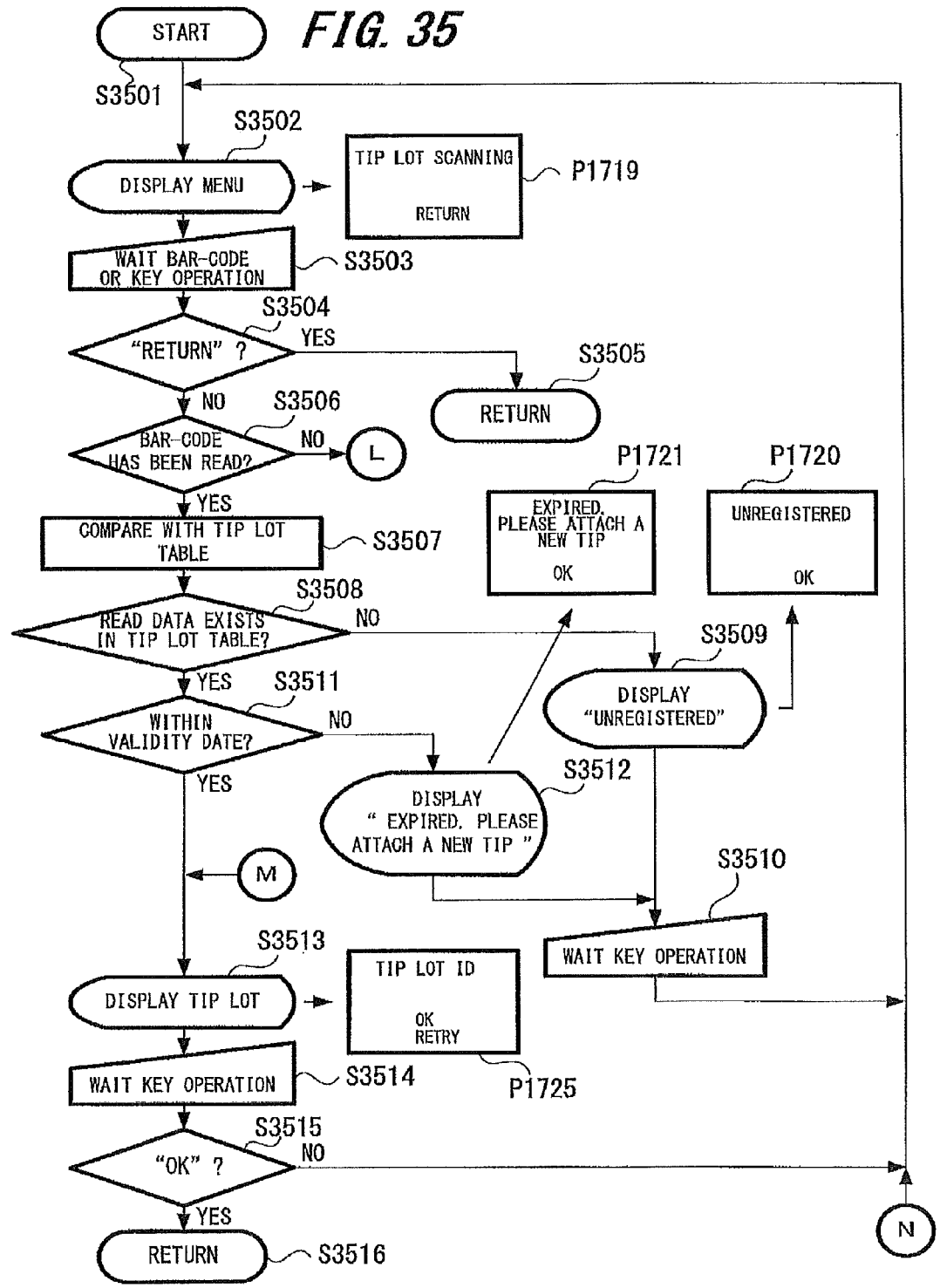
FIG. 35 is a flowchart showing the flow of a tip lot scanning process.
Figure 36:
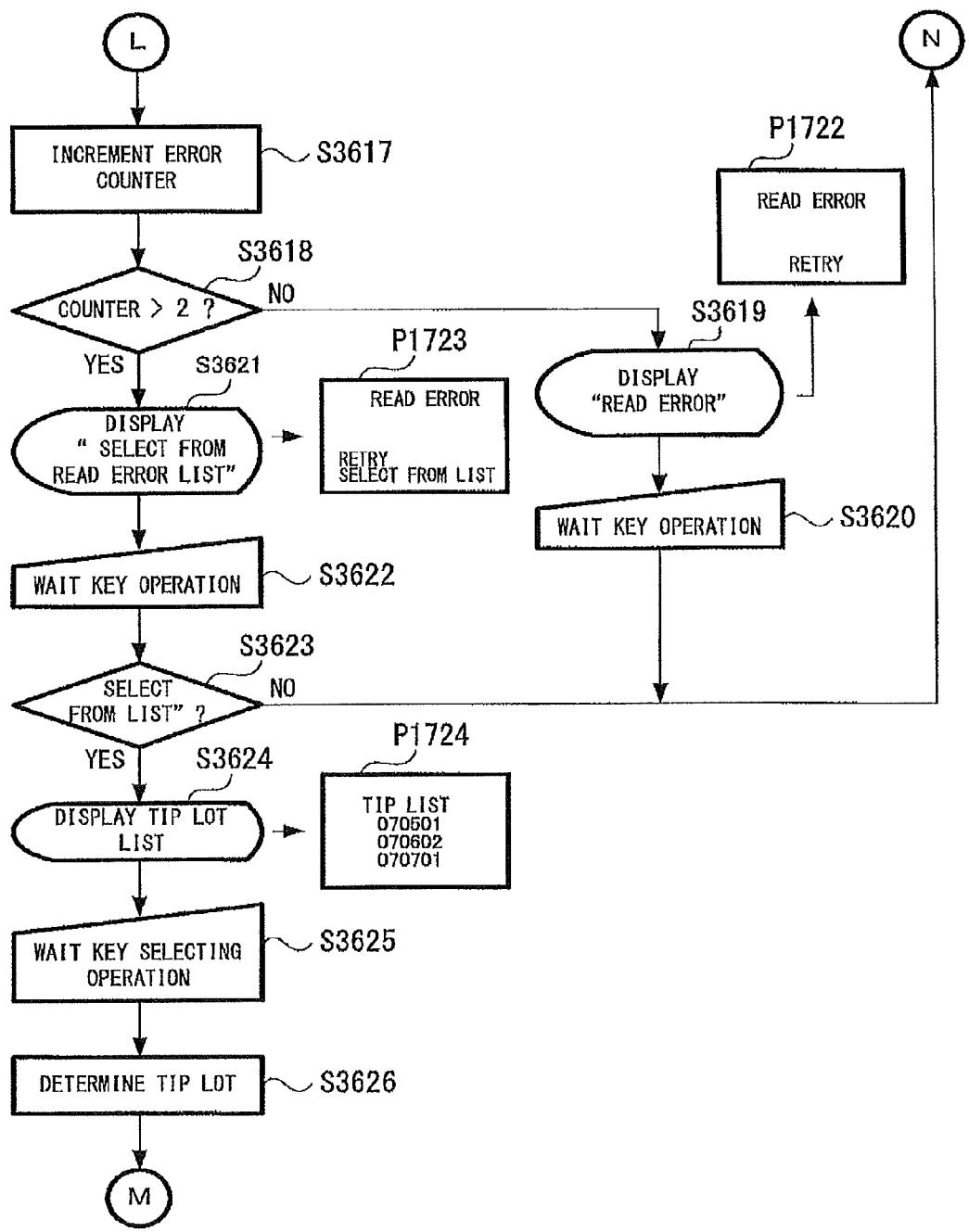
FIG. 36 is a flowchart showing the flow of the tip lot scanning process.

FIGS. 35 and 36 are flowcharts showing the flow of a tip lot scanning process.

Figure 37:
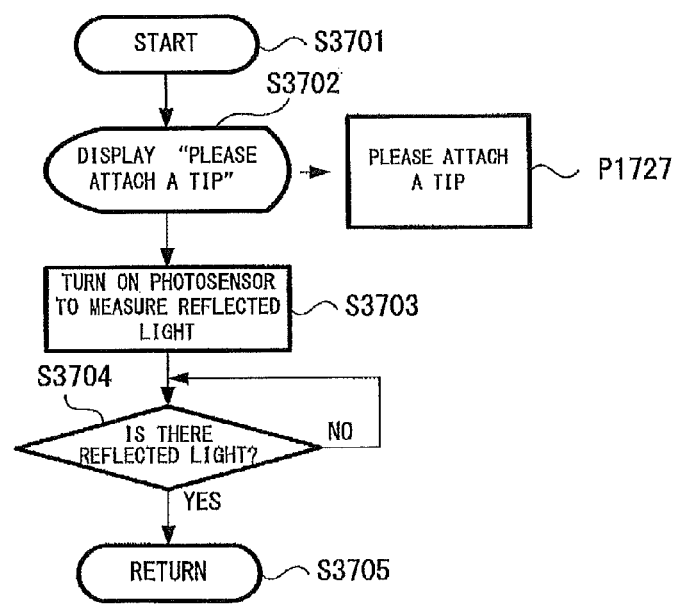
FIG. 37 is a flowchart showing the flow of a tip attaching process.

FIG. 37 is a flowchart showing the flow of a tip attaching process.

Figure 38:
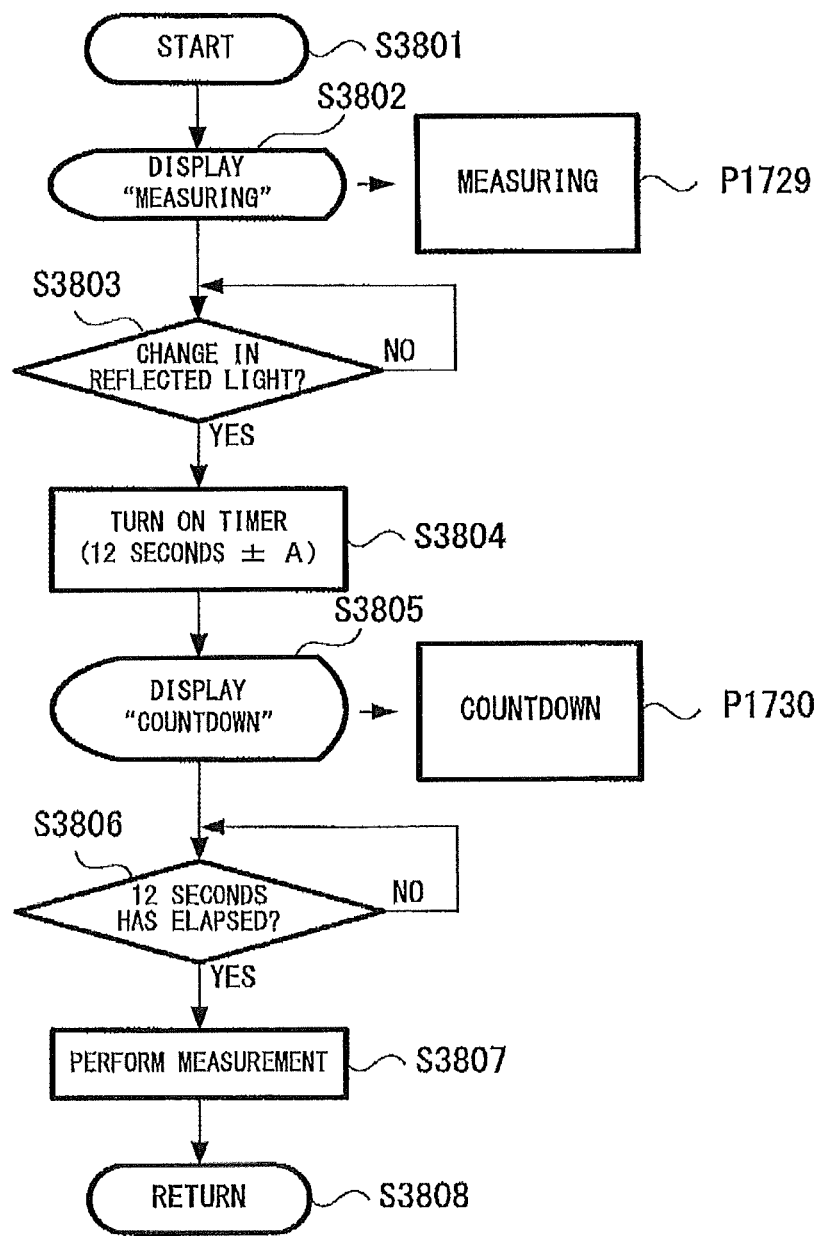
FIG. 38 is a flowchart showing the flow of a measurement execution process.

FIG. 38 is a flowchart showing the flow of a measurement execution process.

Figure 39:
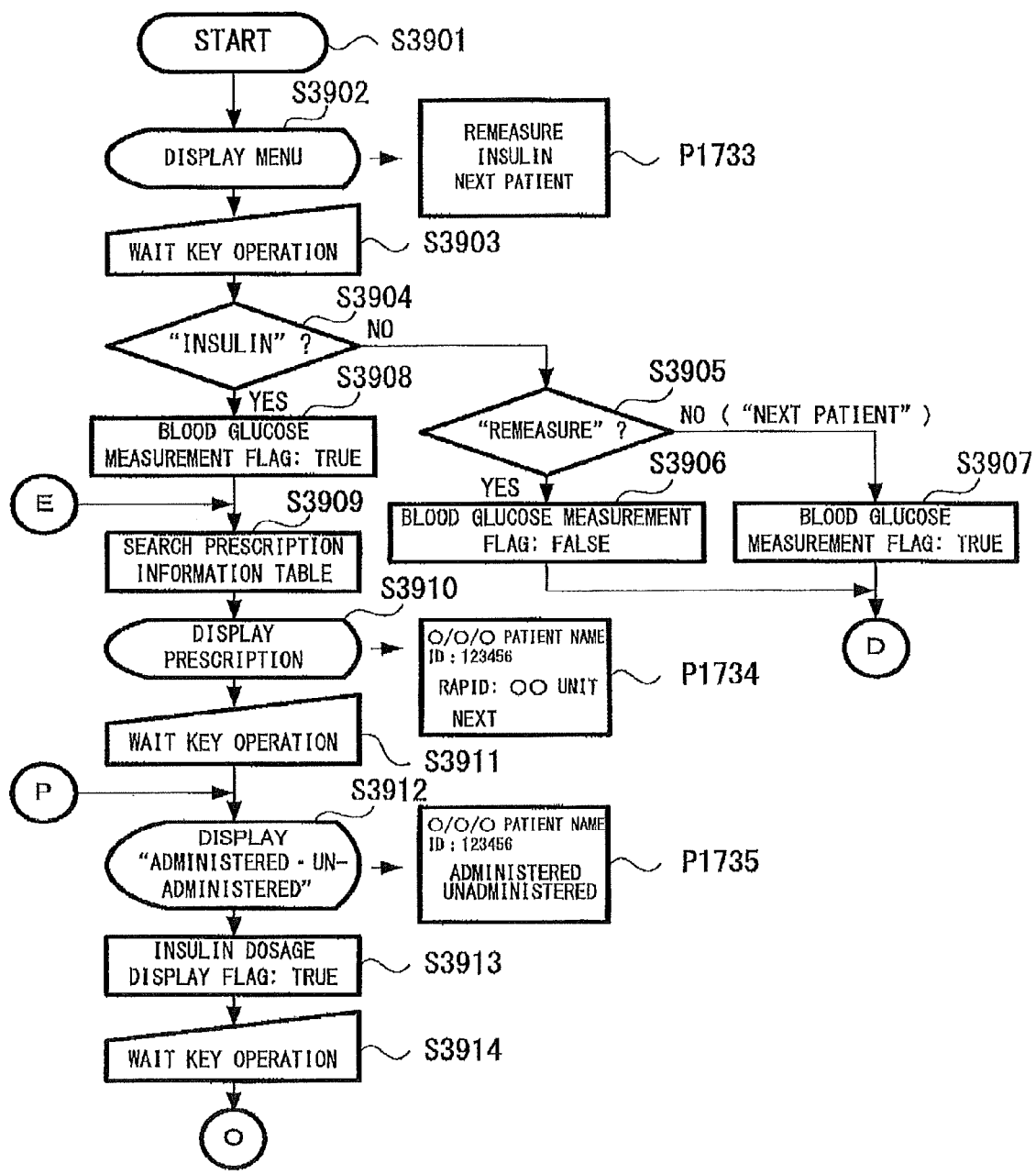
FIG. 39 is a flowchart showing the flow of a prescription display process.
Figure 40:
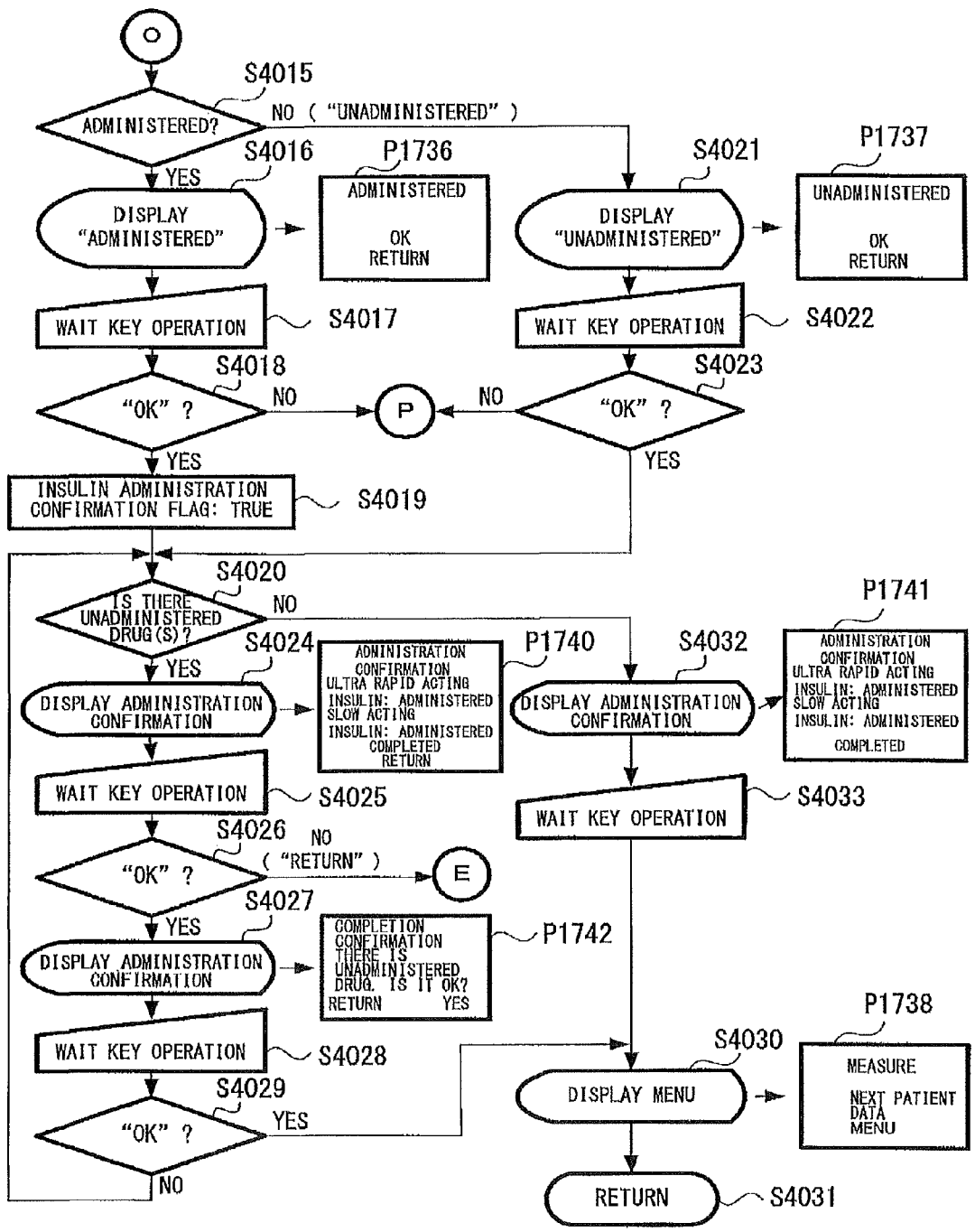
FIG. 40 is a flowchart showing the flow of the prescription display process.

FIGS. 39 and 40 are flowcharts showing the flow of a prescription display process.

[Screen Transition]

The screen transition of the display unit 615 of the blood glucose meter 102 will be described below with reference to FIG. 17 and FIG. 18.

When the nurse presses the power switch 104 of the blood glucose meter 102, an initial screen page P1701 will be displayed on the display unit 615.

On the initial screen page P1701, selection can be performed by the Cursor keys 205 from three items of "PATIENT MEASUREMENT", "QC CHECK" and "SYSTEM SETUP".

When selecting the "QC CHECK" with the Cursor keys 205 and pressing the Enter key 206, a QC check screen page P1702 will be displayed on the display unit 615. Thereafter, the process proceeds to a check procedure, and the details of the check procedure are omitted here.

When selecting the "SYSTEM SETUP" with the Cursor keys 205 and pressing the Enter key 206, a system setup screen page P1703 will be displayed on the display unit 615. Thereafter, the process proceeds to a system setup procedure, and the details of the system setup procedure are omitted here.

On the initial screen page P1701, when selecting the "PATIENT MEASUREMENT" with the Cursor keys 205 and pressing the Enter key 206, the microcomputer will function as the measurement condition check section 1002.

First, the control section 1128 causes the QC check section 1103 to function, and thereby a QC check process is performed in Step S1751. The QC check section 1103 compares the QC check record with the current date and time obtained from the calendar clock 607 to judge, with the judging section 1106, whether or not the QC check has been performed within the predetermined date interval value.

As the judgment result, if it is concluded that the duration from the date when the last QC check was performed has exceeded the predetermined date interval value, a QC warning screen page P1704 will be displayed on the display unit 615 by the control section 1128.

Only the item of "QC CHECK" is displayed on the QC warning screen page P1704, and only operation of the Enter key 206 can be received. It is compelled to change the screen from the QC warning screen page P1704 to the QC check screen page P1702 by operating the Enter key 206.

In the QC check process performed in Step S1751, based on the judgment result, if it is concluded that the duration from the date when the last QC check was performed does not exceed the predetermined date interval value, the control section 1128 will cause the patient ID reading section 1107 to function, and thereby a patient measurement screen page P1705 will be displayed on the display unit 615 by the control section 1128.

On the patient measurement screen page P1705, selection can be performed by the Cursor keys 205 from three items of "MEASURE", "DATA" and "RETURN".

When selecting the "DATA" with the Cursor keys 205 and pressing the Enter key 206, a data screen page P1706 will be displayed on the display unit 615 by the control section 1128. Thereafter, the process proceeds to a past data display procedure, and the details of the past data display procedure are omitted here.

When selecting the "RETURN" with the Cursor keys 205 and pressing the Enter key 206, the screen will return to the initial screen page P1701.

When selecting the "MEASURE" with the Cursor keys 205 and pressing the Enter key 206, a patient ID scanning screen page P1707 will be displayed on the display unit 615 by the control section 1128.

On the patient ID scanning screen page P1707, only a "RETURN" item can be selected. At this time, when pressing the Bar-code key 207, under the control of the control section 1128, the red laser diode 622 of the bar-code reader 208 emits light, and the bar-code reader 208 is brought into a state capable of performing a bar-code read operation through the phototransistor 623.

If the bar-code reader 208 has successfully read the bar-code, the read bar-code data outputted by the bar-code reader 208 will be once stored in the patient ID variable 1108, and the search section 1110 will search to see whether or not the data has been registered in the patient table 1109 stored in the nonvolatile storage 614.

If the data has not been registered, an "UNREGISTERED" screen page P1708 will be displayed on the display unit 615 by the control section 1128. On the "UNREGISTERED" screen page P1708, "OK" is the only item possible to be selected, therefore only operation of the Enter key 206 can be received as operation of the operating section 608. On such screen page, when pressing the Enter key 206, the screen of the display unit 615 will return to the patient ID scanning screen page P1707.

If the data has been registered, a patient name display screen page P1712 will be displayed on the display unit 615 by the control section 1128.

If the bar-code has not been successfully read, a read error screen page P1709 will be displayed on the display unit 615 by the control section 1128 until the error has been repeated two times. Only "RETRY", as selection item, is displayed on this screen page, and only the Enter key 206 can be received. On such screen page, when pressing the Enter key 206, the screen of the display unit 615 will return to the patient ID scanning screen page P1707.

In the case where the bar-code has not been successfully read, if the error is repeated three or more times, a read error screen page P1710 will be displayed on the display unit 615 by the control section 1128.

As selection item, an item "SELECT FROM LIST" as well as the item "RETRY" are played on such screen page.

When selecting the "RETRY" and pressing the Enter key 206, the screen of the display unit 615 will return to the patient ID scanning screen page P1707.

When selecting the "SELECT FROM LIST" and pressing the Enter key 206, a patient list screen page P1711 will be displayed on the display unit 615 by the control section 1128.

On the patient list screen page P1711, a list of patient names and patient IDs from the patient table 1109 stored in the nonvolatile storage 614 is displayed. When selecting a patient ID with the Cursor keys 205 and pressing the Enter key 206, the patient name display screen page P1712 will be displayed on the display unit 615 by the control section 1128.

As timing for displaying the "SELECT FROM LIST", the number of the repeating times of the read error is not particularly limited, and preferable number of the repeating times is two to four. Further, other conditions may be added such as long-pressing the Enter key 206.

When the patient name display screen page P1712 is displayed on the display unit 615, the patient ID read by the bar-code reader 208 or selected on the patient list screen page P1711 is stored in the patient ID variable 1108.

On the patient name display screen page P1712, selection can be performed by the Cursor keys 205 from two items of "OK" and "RETRY".

When selecting the "RETRY" with the Cursor keys 205 and pressing the Enter key 206, the screen of the display unit 615 will return to the patient ID scanning screen page P1707.

Figure 19:
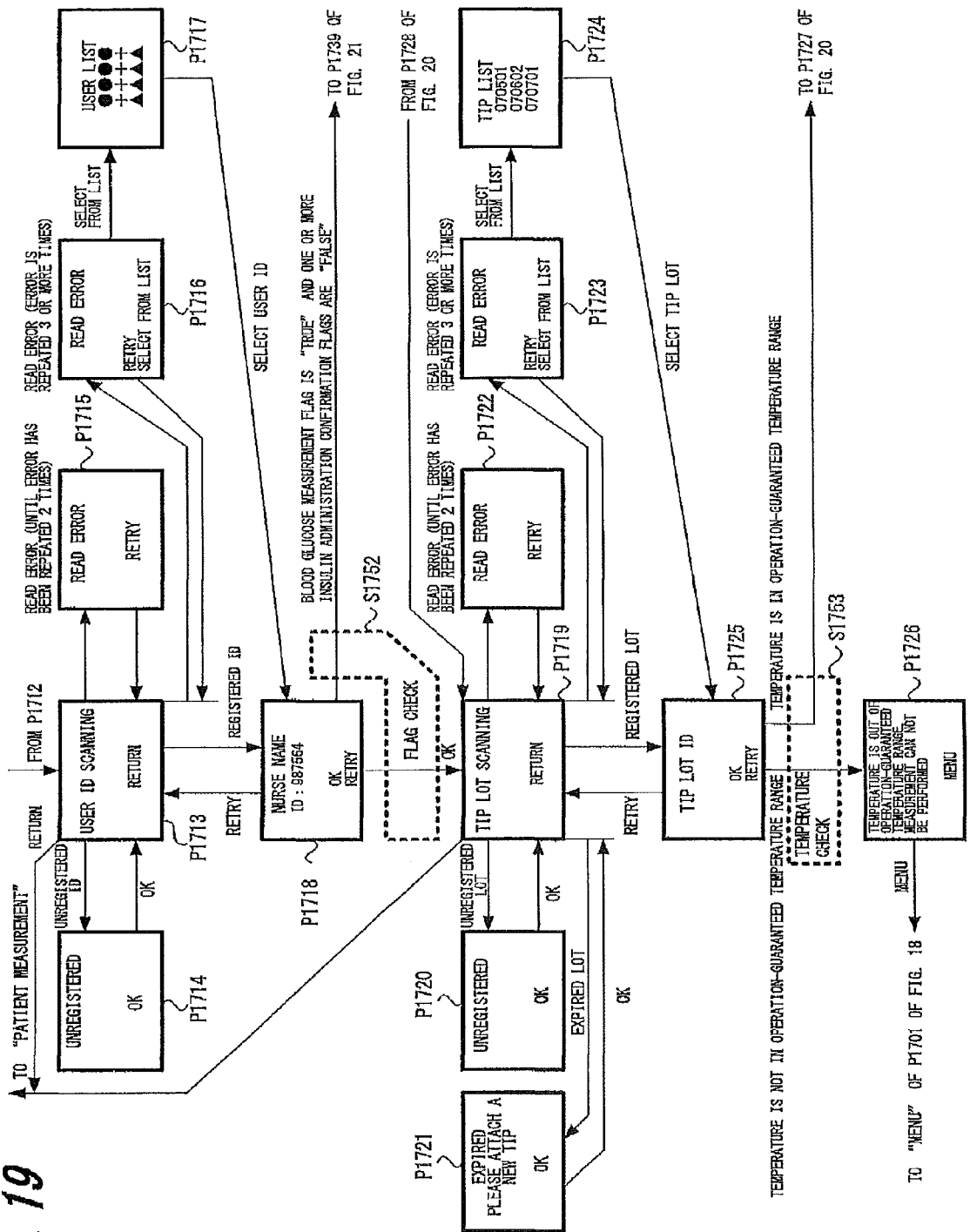
FIG. 19 is a partly enlarged view of the state transition diagram.

When selecting the "OK" with the Cursor keys 205 and pressing the Enter key 206, the control section 1128 will cause the user ID reading section 1111 to operate, and thereby a user ID scanning screen page P1713 shown in FIG. 19 will be displayed on the display unit 615 by the control section 1128.

The screen transition of the display unit 615 of the blood glucose meter 102 after FIG. 18 will be described below with reference to FIG. 17 and FIG. 19.

On the user ID scanning screen page P1713, only a "RETURN" item can be selected. At this time, when pressing the Bar-code key 207, under the control of the control section 1128, the red laser diode 622 of the bar-code reader 208 emits light, and the bar-code reader 208 is brought into a state capable of performing a bar-code read operation.

If the bar-code reader 208 has successfully read the bar-code, the read bar-code data will be once stored in the user ID variable 1112, and the search section 1114 will search to see whether or not the data has been registered in the user table 1113 stored in the nonvolatile storage 614.

If the data has not been registered, an "UNREGISTERED" screen page P1714 will be displayed on the display unit 615 by the control section 1128. Only "OK", as selection item, is displayed on this screen page, and only the Enter key 206 is received. When pressing the Enter key 206, the screen will return to the user ID scanning screen page P1713.

If the data has been registered, a user name display screen page P1718 will be displayed on the display unit 615 by the control section 1128.

If the bar-code has not been successfully read, a read error screen page P1715 will be displayed on the display unit 615 until error has been repeated two times. Only "RETRY", as selection item, is displayed on this screen page, and only the Enter key 206 is received. When pressing the Enter key 206, the screen will return to the user ID scanning screen page P1713.

In the case where the bar-code has not been successfully read, if the error is repeated three or more times, a read error screen page P1716 will be displayed on the display unit 615.

As selection item, an item "SELECT FROM LIST" as well as the item "RETRY" are played on such screen page.

When selecting the "RETRY" and pressing the Enter key 206, the screen will return to the user ID scanning screen page P1713.

When selecting the "SELECT FROM LIST" and pressing the Enter key 206, a user list screen page P1717 will be displayed on the display unit 615 by the control section 1128.

On the user list screen page P1717, a list of user names and user. IDs from the user table 1113 in the nonvolatile storage 614 is displayed. When selecting a user ID with the Cursor keys 205 and pressing the Enter key 206, the user name display screen page P1718 will be displayed on the display unit 615.

As timing for displaying the "SELECT FROM LIST", the number of the repeating times of the read error is not particularly limited, and preferable number of the repeating times is one to four. Further, other conditions may be added such as long-pressing the Enter key 206.

When the user name display screen page P1718 is displayed on the display unit 615, the user ID read by the bar-code reader 208 or selected on the user list screen page P1717 is stored in the user ID variable 1112.

On the user name display screen page P1718, selection can be performed by the Cursor keys 205 from two items of "OK" and "RETRY".

When selecting the "RETRY" with the Cursor keys 205 and pressing the Enter key 206, the screen will return to the user ID scanning screen page P1713.

When selecting the "OK" with the Cursor keys 205 and pressing the Enter key 206, the verification of the blood glucose measurement flag and insulin administration confirmation flag of the measurement/prescription results table 1408 will be performed in Step S1752.

Figure 21:
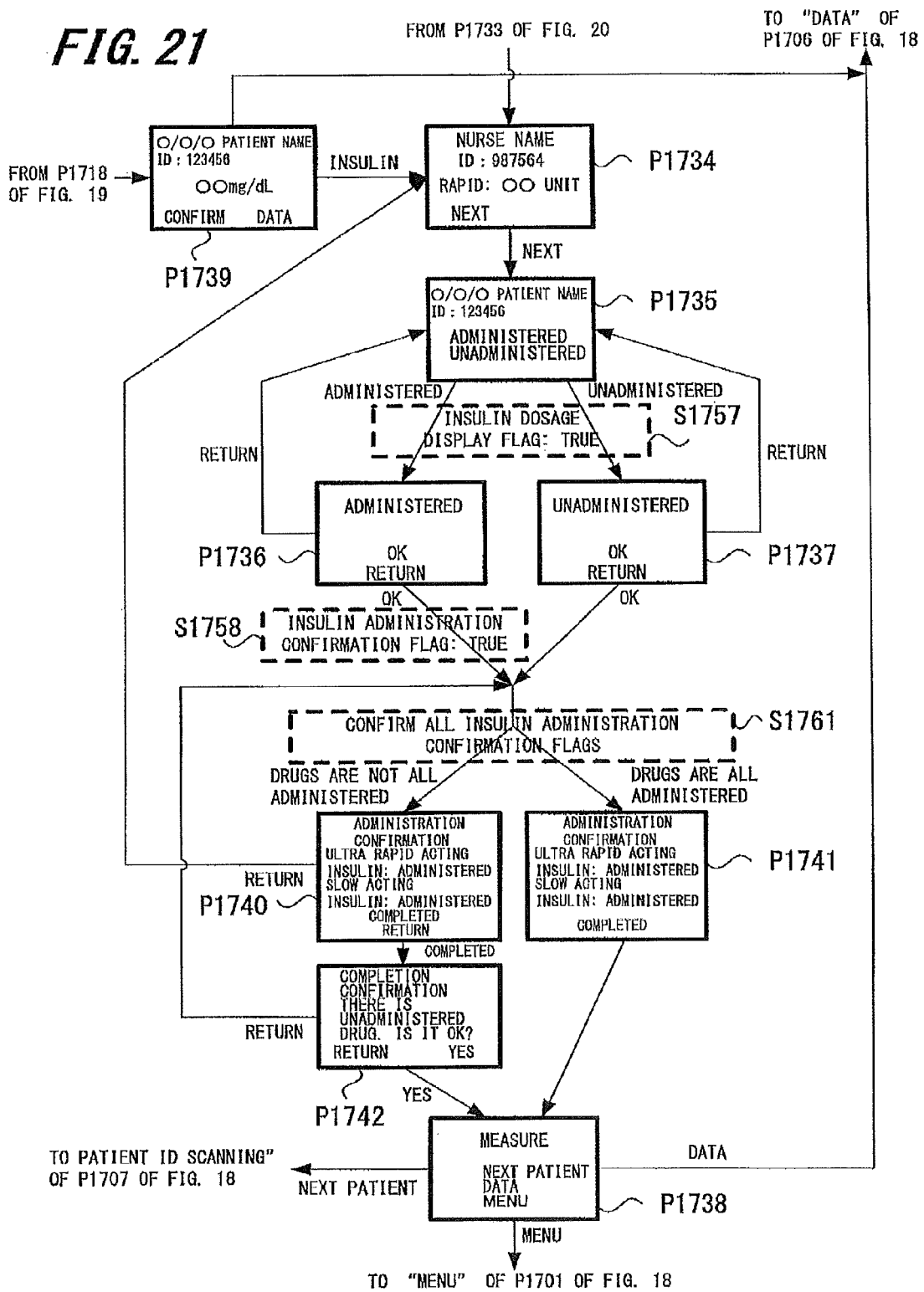
FIG. 21 is a partly enlarged view of the state transition diagram.

In the case where the blood glucose measurement flag is "true" and one or more insulin administration confirmation flags are "false", a blood glucose level display screen page P1739 shown in FIG. 21 will be displayed by the control section 1128.

In the case where the state of the blood glucose measurement flag and the insulin dosage display flag is not the afore- said combination, a tip lot scanning screen page P1719 will be displayed on the display unit 615 by the control section 1128.

Step S1752 is a necessary confirming procedure when collectively measuring the blood glucose for a plurality of patients and then collectively administering insulin to the plurality of patients having received the blood glucose measurement. In other words, by confirming the aforesaid flags, it is possible to confirm whether or not the "collectively measuring" has been performed, instead of individually measuring blood glucose level for each patient and then performing insulin administration.

On the tip lot scanning screen page P1719, only a "RETURN" item can be selected. At this time, when pressing the Bar-code key 207, the red laser diode 622 of the bar-code reader 208 will emit light, and the bar-code reader 208 will be brought into a state capable of performing a bar-code read operation.

When the bar-code has been successfully read, verification will be performed to see whether or not the bar-code is the one having been registered in the tip lot table 1117 of the non-volatile storage 614.

If the bar-code has not been registered, an "UNREGISTERED" screen page P1720 will be displayed on the display unit 615.

Only "OK", as selection item, is displayed on this screen page, and only the Enter key 206 is received. When pressing the Enter key 206, the screen will return to the tip lot scanning screen page P1719.

If the bar-code has been registered, a tip lot display screen page P1725 will be displayed on the display unit 615.

As described above, the tip lots and validity dates of the tip lots are recorded in the tip lot table 1117.

Even in the case where the bar-code has been successfully read, if it is judged, by acquiring the current date and time information by the calendar clock 607, that the lot of the measuring tip 212 has passed the validity date, an expiration error screen page P1721 will be displayed on the display unit 615.

Only "OK", as selection item, is displayed on this screen page, and only operation of the Enter key 206 can be received. When pressing the Enter key 206, the screen will return to the tip lot scanning screen page P1719. In other words, it is compelled to attach a measuring tip 212 within validity date.

If the bar-code has not been successfully read, a read error screen page P1722 will be displayed on the display unit 615 by the control section 1128 until error has been repeated two times. Only "RETRY", as selection item, is displayed on this screen page, and only operation of the Enter key 206 can be received. When pressing the Enter key 206, the screen will return to the tip lot scanning screen page P1719.

In the case where the bar-code has not been successfully read, if the error is repeated three times, a read error screen page P1723 will be displayed on the display unit 615 by the control section 1128.

As selection item, an item "SELECT FROM LIST" as well as the item "RETRY" are played on this screen page.

When selecting the "RETRY" and pressing the Enter key 206, the screen page will return to the tip lot scanning screen page P1719.

When selecting the "SELECT FROM LIST" and pressing the Enter key 206, a tip lot list screen page P1724 will be displayed on the display unit 615 by the control section 1128.

On the tip lot list screen page P1724, a list of tip lots from the tip lot table 1117 stored in the nonvolatile storage 614 is displayed. When selecting a tip lot with the Cursor keys 205 and pressing the Enter key 206, the tip lot display screen page P1725 will be displayed on the display unit 615.

As timing for displaying the "SELECT FROM LIST", the number of the repeating times of the read error is not particularly limited, and preferable number of the repeating times is zero to four. Further, other conditions may be added such as long-pressing the Enter key 206.

When the tip lot display screen page P1725 is displayed on the display unit 615, the tip lot read by the bar-code reader 208 or selected from the tip lot list screen page P1724 is stored in the tip lot variable 1116.

On the tip lot display screen page P1725, selection can be performed by the Cursor keys 205 from two items of "OK" and "RETRY".

When selecting the "RETRY" with the Cursor keys 205 and pressing the Enter key 206, the screen will return to the tip lot scanning screen page P1719.

When selecting the "OK" with the Cursor keys 205 and pressing the Enter key 206, the control section 1128 will cause the temperature check section 1119 to operate, and thereby temperature check will be performed in Step S1753. Further, if the temperature is within the allowable range, the control section 1128 will cause the tip attachment check section 1123 to operate, and thereby a "PLEASE ATTACH A TIP" screen page P1727 shown in FIG. 20 will be displayed on the display unit 615 by the control section 1128.

If the temperature is not within the allowable range, a temperature error screen page P1726 will be displayed on the display unit 615. Which means the ambient temperature is not suitable for performing the blood glucose measurement. Further, since the blood glucose measurement should not be performed when such screen page appears, only "MENU" can be selected, and it is compelled to return the screen to the initial screen page P1701.

Incidentally, when the blood glucose meter 102 is not performing the blood glucose measurement operation and insulin dosage display operation, the temperature check section 1119 may also periodically measure the temperature at a time interval of one minute, for example. In such case, when it is detected that the temperature is not within the allowable range, it is possible to display an alarm on the display unit 615 and prohibit the bar-code reading operation of the patient ID and user ID, therefore non-productive works can be prevented.

The screen transition of the display unit 615 of the blood glucose meter 102 after FIG. 19 will be described below with reference to FIG. 17 and FIG. 20.

On the "PLEASE ATTACH A TIP" screen page P1727, operation of the Cursor keys 205, Enter key 206 and the like can not be received. The "PLEASE ATTACH A TIP" screen page P1727 is displayed to tell that the device is in a state of readiness to detect the normal attachment of the measuring tip 212.

In the case where the "PLEASE ATTACH A TIP" screen page P1727 is being displayed, if a used measuring tip 212 is attached by mistake, the tip attachment detection section 1124 will compare the quantity of the reflected light with the threshold and judge that the measuring tip 212 is deemed a used one. Upon receiving such judgment, the control section 1128 displays a defective tip screen page P1728 on the display unit 615. Only "OK", as selection item, is displayed on this screen page, and the screen returns to the tip lot scanning screen page P1719.

On the "PLEASE ATTACH A TIP" screen page P1727, if a new measuring tip 212 is attached, the tip attachment detection section 1124 will detect that a non-defective product measuring tip 212 has been attached. Upon receiving the detection result of the tip attachment detection section 1124, the control section 1128 functions as the blood glucose measuring section 1003. As a result, a "MEASURING" screen page P1729 is displayed on the display unit 615 by the control section 1128. This screen page tells that the device is brought into a state where the optical measuring section 202 is caused to operate, and the optical measuring section 202 is in a standby state to detect the operation of causing the measuring tip 212 to soak the blood.

When the blood is soaked into the measuring tip 212, the quantity of the reflected light from the test piece 1127 inside the measuring Lip 212 will change. When the detection section 1404 detects such change through the phototransistor 612 and the A/D converter 613, a "COUNTDOWN" screen page P1730 will be displayed on the display unit 615 by the control section 1128. From this time, the control section 1128 causes a timer to operate to wait until a predetermined time has elapsed. The predetermined time set for the timer is about 12 seconds, and changes according to the temperature. The control section 1128 calculates the necessary change of the predetermined time based on the temperature measured by the thermistor 606.

When the predetermined time has elapsed since the "COUNTDOWN" screen page P1730 is displayed on the display unit 615, a blood glucose level display screen page P1732 will be displayed on the display unit 615 by the control section 1128.

On the blood glucose level display screen page P1732, selection can be performed by the Cursor keys 205 from two items of "CONFIRM" and "DATA".

When selecting the "CONFIRM" with the Cursor keys 205 and pressing the Enter key 206, the control section 1128 will confirm all insulin administration confirmation flags recorded in the records of the patient of the measurement/prescription results table 1408 in Step S1754.

In Step S1754, if all of the insulin administration confirmation flags are "true", i.e., if all of the insulin administration processes necessary for the patient are completed, a blood glucose measurement menu screen page P1731 will be displayed on the display unit 615 by the control section 1128.

On the blood glucose measurement menu screen page P1731, selection can be performed by the Cursor keys 205 from two items "REMEASURE" and "NEXT PATIENT".

Figure 18:
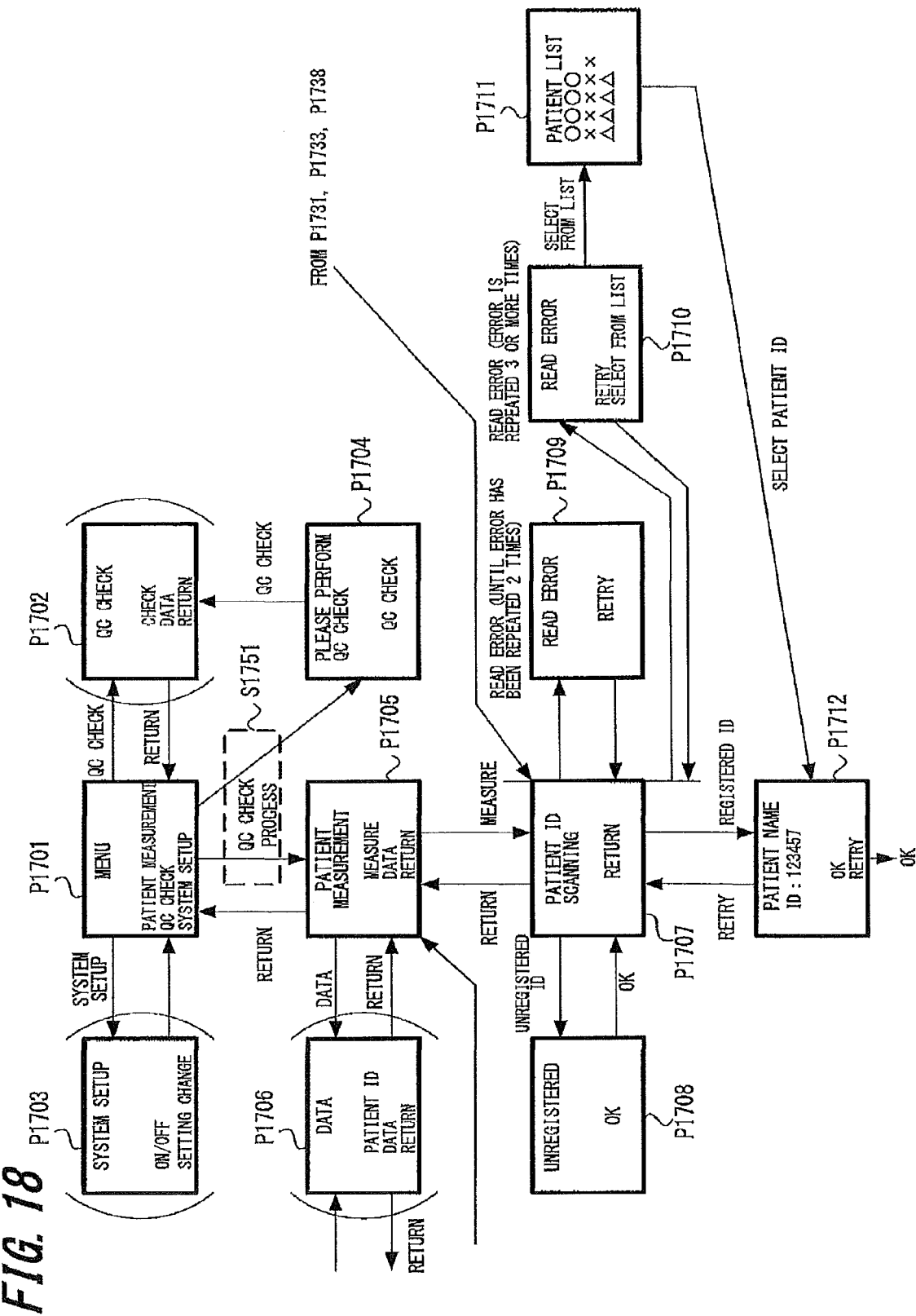
FIG. 18 is a partly enlarged view of the state transition diagram.

When selecting the "REMEASURE" with the Cursor keys 205 and pressing the Enter key 206, the blood glucose measurement flag will be set to "false" in Step S1759, and the screen will return to the patient ID scanning screen page P1707 (see FIG. 18).

When selecting the "NEXT PATIENT" with the Cursor keys 205 and pressing the Enter key 206, the blood glucose measurement flag will be set to "true" in Step S1760, and the screen will return to the patient ID scanning screen page P1707.

In Step S1754, when even one of the insulin administration confirmation flags is "false", i.e., when necessary insulin administration processes for the patient are not all completed, an insulin administration menu screen page P1733 will be displayed on the display unit 615 by the control section 1128.

On the insulin administration menu screen page P1733, selection can be performed by the Cursor keys 205 from three items of "REMEASURE", "INSULIN" and "NEXT PATIENT".

When selecting the "REMEASURE" with the Cursor keys 205 and pressing the Enter key 206, the blood glucose measurement flag will be set to "false" in Step S1755, and the screen will return to the patient ID scanning screen page P1707.

When selecting the "NEXT PATIENT" with the Cursor keys 205 and pressing the Enter key 206, the blood glucose measurement flag will be set to "true" in Step S1756, and the screen will return to the patient ID scanning screen page P1707.

When selecting the "INSULIN" with the Cursor keys 205 and pressing the Enter key 206, the blood glucose measurement flag will be set to "true" in Step S1756, and the control section 1128 will function as the prescription data display section 804. As a result, an insulin dosage display screen page P1734 shown in FIG. 21 is displayed on the display unit 615 by the control section 1128.

It can be known by comparing the blood glucose measurement menu screen page P1731 with the insulin administration menu screen page P1733 that, in the insulin administration menu screen page P1733, an item "INSULIN" can be selected, while in the blood glucose measurement menu screen page P1731, there is no such item.

With such a configuration, since the all insulin administration processes have been performed for the patient, the accident of executing duplicated administration of insulin can be prevented.

The screen transition of the display unit 615 of the blood glucose meter 102 after FIG. 20 will be described below with reference to FIG. 17 and FIG. 21.

On the insulin dosage display screen page P1734, only a "NEXT" item can be selected. The user such as a nurse or the like views the kind and dosage, i.e., the prescription data, of the insulin displayed on such screen page to confirm the kind and dosage of the drug to be administered to the patient.

On the insulin dosage display screen page P1734, when pressing the Enter key 206, an administration selection screen page P1735 will be displayed on the display unit 615.

On the administration selection screen page P1735, selection can be performed by the Cursor keys 205 from two items of "ADMINISTERED" and "UNADMINISTERED".

When selecting the "ADMINISTERED" with the Cursor keys 205 and pressing the Enter key 206, the insulin dosage display flag will be set to "true" in Step S1757, and then an "ADMINISTERED" screen page P1736 will be displayed on the display unit 615 by the control section 1128.

When selecting the "UNADMINISTERED" with the Cursor keys 205 and pressing the Enter key 206, the insulin dosage display flag will be set to "true" in Step S1757, and thereafter an "UNADMINISTERED" screen page P1737 will be displayed on the display unit 615 by the control section 1128.

Incidentally, the present invention also include a possible configuration in which a selection item "RETURN" is further provided on the administration selection screen page P1735, and the screen returns to the insulin dosage display screen page P1734 by selecting the "RETURN". Further, the present invention also includes another possible configuration in which kind and dosage of the drug to be administered to the patient is displayed on the administration selection screen page P1735. By employing the aforesaid selection items, kind and dosage of the drug can be reconfirmed when performing insulin administration.

On the "ADMINISTERED" screen page P1736, selection can be performed from two items of "OK" and "RETURN".

When selecting the "OK" with the Cursor keys 205 and pressing the Enter key 206, the insulin administration confirmation flag will be set to "true" in Step S1758, and then the process will proceed to Step S1761.

When selecting the "RETURN" with the Cursor keys 205 and pressing the Enter key 206, the screen will return to the administration selection screen page P1735.

On the "UNADMINISTERED" screen page P1737, selection can be performed from two items of "OK" and "RETURN".

When selecting the "OK" with the Cursor keys 205 and pressing the Enter key 206, the process will proceed to Step S1761.

When selecting the "RETURN" with the Cursor keys 205 and pressing the Enter key 206, the screen will return to the administration selection screen page P1735.

Note that, unlike the time when the "ADMINISTERED" screen page P1736 is displayed, at the time when the "UNADMINISTERED" screen page P1737 is displayed, there is no insulin administration confirmation flag set in Step S1758, i.e., the insulin administration confirmation flag keeps in "false" state.

When selecting "OK" on both the "ADMINISTERED" screen page P1736 and "UNADMINISTERED" screen page P1737, the process will proceed to Step S1761.

Similar to Step S1754 (see FIG. 20), in Step S1761, the control section 1128 confirms all insulin administration confirmation flags recorded in the records of the patient of the measurement/prescription results table 1408.

In Step S1761, if all of the insulin administration confirmation flags are "true", i.e., if all of the insulin administration processes necessary for the patient are completed, an administration confirmation screen page P1741 will be displayed on the display unit 615 by the control section 1128.

Only "COMPLETION" can be selected on the administration confirmation screen page P1741. In other words, only the Enter key 206 can be pressed.

On the administration confirmation screen page P1741, when pressing the Enter key 206, a "NEXT PATIENT" screen page P1738 will be displayed on the display unit 615 by the control section 1128.

In Step S1761, when even one of the insulin administration confirmation flags is "false", i.e., when insulin administration processes necessary for the patient are not all completed, an administration confirmation screen page P1740 will be displayed on the display unit 615 by the control section 1128.

On the administration confirmation screen page P1740, selection can be performed by the Cursor keys 205 from two items of "COMPLETION" and "RETURN".

When selecting the "COMPLETION" with the Cursor keys 205 and pressing the Enter key 206, a completion confirmation screen page P1742 will be displayed on the display unit 615 by the control section 1128.

When selecting the "RETURN" with the Cursor keys 205 and pressing the Enter key 206, the screen will return to the insulin dosage display screen page P1734.

On the completion confirmation screen page P1742, a message is displayed which tells that the patient whose prescription is being currently displayed has unadministered drug prescription(s). Further, as selection item asking whether the drug(s) should be administered or whether the drug(s) should be transferred to other patient(s), there are two items of "RETURN" and "YES" can be selected.

When selecting the "RETURN" with the Cursor keys 205 and pressing the Enter key 206, the process will proceed to Step S1761. As a result, since there is unadministered drug(s), screen is returned to the administration confirmation screen page P1740.

When selecting the "YES" with the Cursor keys 205 and pressing the Enter key 206, a "NEXT PATIENT" screen page P1738 will be displayed on the display unit 615 by the control section 1128.

On the "NEXT PATIENT" screen page'P1738, selection can be performed from three items of "NEXT PATIENT", "DATA" and "MENU".

When selecting the "NEXT PATIENT" with the Cursor keys 205 and pressing the Enter key 206, the screen will return to the patient ID scanning screen page P1707 (see FIG. 18).

When selecting the "DATA" with the Cursor keys 205 and pressing the Enter key 206, a data screen page P1706 (see FIG. 18) will be displayed on the display unit 615 by the control section 1128.

When selecting the "MENU" with the Cursor keys 205 and pressing the Enter key 206, the screen will return to the initial screen page P1701 (see FIG. 18).

On the blood glucose level display screen page P1739, selection can be performed by the Cursor keys 205 from two items of "INSULIN" and "DATA".

When selecting the "INSULIN" with the Cursor keys 205 and pressing the Enter key 206, the insulin dosage display screen page P1734 will be displayed on the display unit 615 by the control section 1128.

When selecting the "DATA" with the Cursor keys 205 and pressing the Enter key 206, a data screen page P1706 will be displayed on the display unit 615 by the control section 1128. After referring to the past blood glucose measurement history, the screen is returned to blood glucose level display screen page P1739 by selecting "RETURN".

[Workflow and Screen Transition]

Figure 22A:
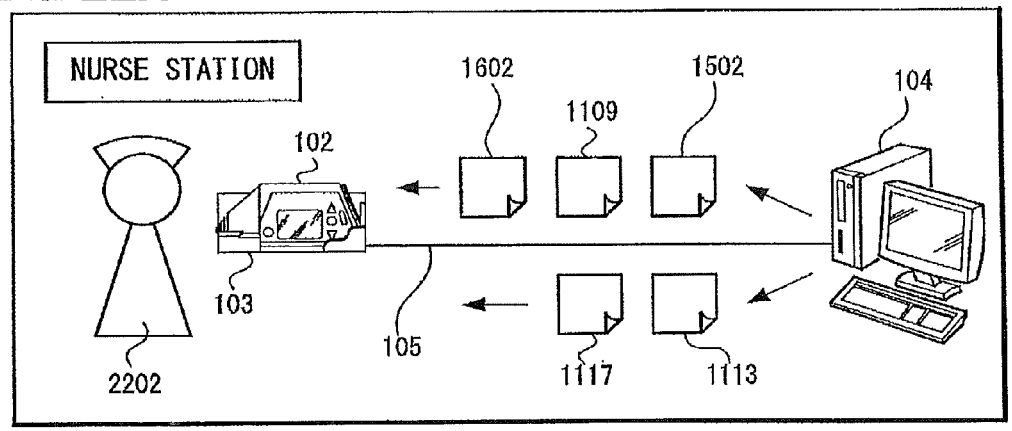
FIGS. 22A, 22B and 22C are schematic views showing nurse's workflow and attendant screen transition of the blood glucose meter.

Nurse's workflow will be described below with reference to FIG. 22A.

In many cases, insulin administration is performed to hospitalized patients before meal. At this time, blood glucose measurement is performed.

As preparation for performing blood glucose measurement and insulin administration prescription, a nurse 2202 mounts the blood glucose meter 102 on the cradle 103 before the patients having meal. As a result, data communication between the measurement data management device 104 and the blood glucose meter 102 is performed through the cradle 103, and the measurement data management device 104 transfers the patient table 1109, the user table 1113, the tip lot table 1117, the prescription information table 1502 and the measurement/prescription table 1602 to the blood glucose meter 102.

However, it is assumed that the blood glucose meter 102 according to the present embodiment is in a state where the measurement/prescription results table 1408 left in the blood glucose meter 102 is deleted before performing the blood glucose measurement process and insulin administration prescription process. To make sure that such procedure is reliably performed, the operation of previously mounting the blood glucose meter 102 on the cradle 103 must be performed before performing the blood glucose measurement process and insulin administration prescription process. The state where the measurement/prescription results table 1408 is deleted represents the state where the blood glucose meter 102 is ready for performing measurement.

Figure 22B:
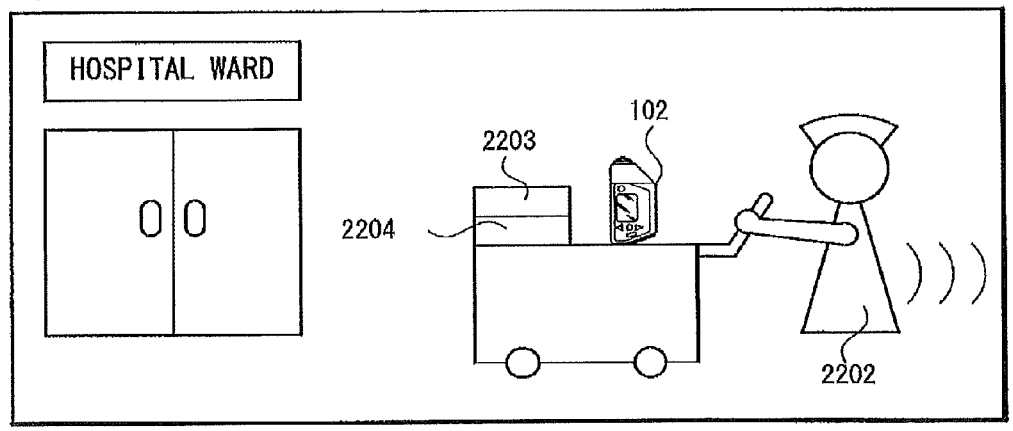

Description of the nurse's workflow will be continued below with reference to FIG. 22B.

The nurse 2202 prepares the blood glucose meter 102, measuring tips 2203 and insulin syringes 2204 and goes from the nurse station to the hospital ward, wherein the number of the measuring tips 2203 and the number of the insulin syringes 2204 are equal to or more than the number of the patients.

Description of the nurse's workflow will be continued below with reference to FIG. 22C.

Figure 22C:
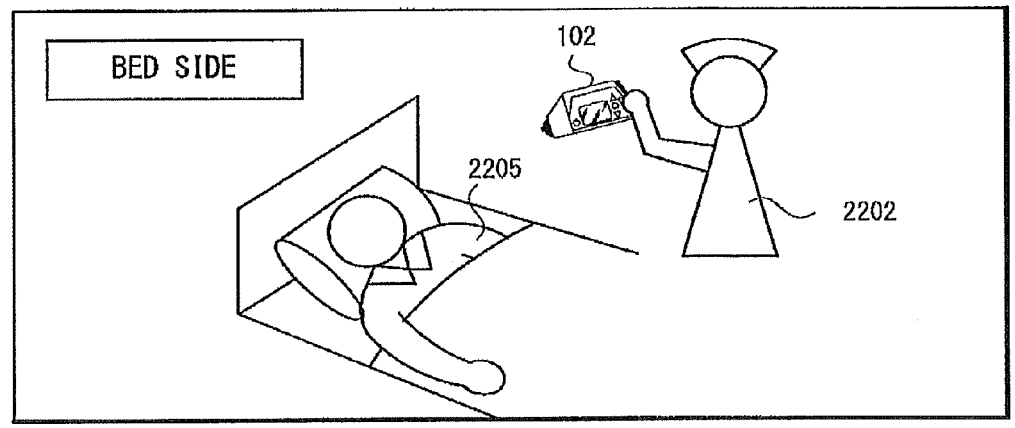

In FIG. 22C, upon reaching the bed of a patient 2205, the nurse 2202 starts the blood glucose measurement process with the blood glucose meter 102.

Description of the nurse's workflow will be continued below with reference to FIG. 23D.

The nurse 2202 operates the blood glucose meter 102 to display the patient ID scanning screen page P1707 on the LCD 203. Further, the nurse 2202 presses the Bar-code key 207 to cause the bar-code reader 208 to scan a patient ID 2306, which is a bar-code, of the patient 2205.

If bar-code reading is successful, the patient name display screen page P1712 will be displayed on the LCD 203.

The nurse 2202 confirms the contents of the display, selects "OK" with the Cursor keys 205, and presses the Enter key 206. As a result, the user ID scanning screen page P1713 is displayed on the LCD 203.

Description of the nurse's workflow will be continued below with reference to FIG. 23E.

In the state where the user ID scanning screen page P1713 is being displayed on the LCD 203, the nurse 2202 presses the Bar-code key 207 to cause the bar-code reader 208 to scan a nurse ID 2307, which is a bar-code, of the nurse 2202.

If bar-code reading is successful, the user name display screen page P1718 will be displayed on the LCD 203.

The nurse 2202 confirms the contents of the display, selects "OK" with the Cursor keys 205, and presses the Enter key 206. As a result, the tip lot scanning screen page P1719 is displayed on the LCD 203.

Description of the nurse's workflow will be continued below with reference to FIG. 23F.

In the state where the tip lot scanning screen page P1719 is being displayed on the LCD 203, the nurse 2202 presses the Bar-code key 207 to cause the bar-code reader 208 to scan a tip lot 2308, which is a bar-code, printed on a box 2309 or wrapping of the measuring tip 2203.

If bar-code reading is successful, the tip lot display screen page P1725 will be displayed on the LCD 203.

The nurse 2202 confirms the contents of the display, selects "OK" with the Cursor keys 205, and presses the Enter key 206. As a result, the "PLEASE ATTACH A TIP" screen page P1727 is displayed on the LCD 203.

Figure 24G:
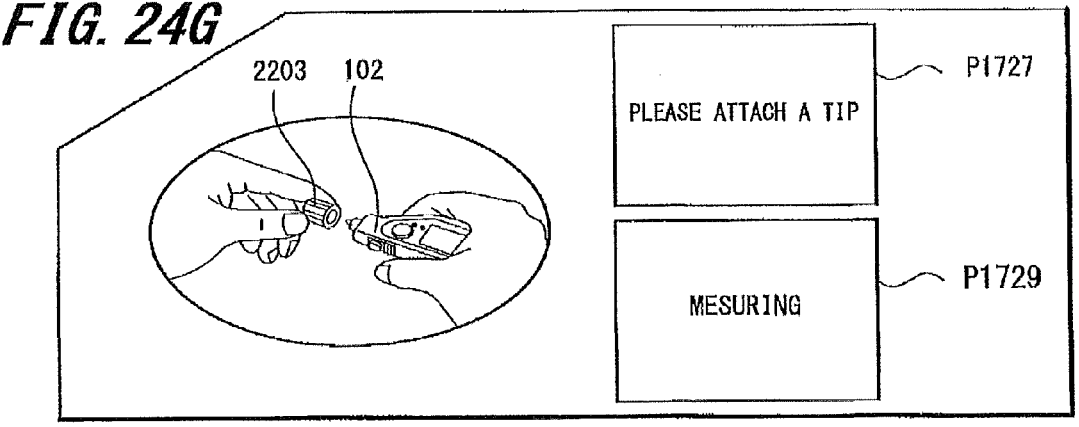
FIGS. 24G, 24H, 24I and 24J are schematic views showing nurse's workflow and attendant screen transition of the blood glucose meter.

Description of the nurse's workflow will be continued below with reference to FIG. 24G.

In the state where the "PLEASE ATTACH A TIP" screen page P1727 is being displayed on the LCD 203, the nurse 2202 attaches a measuring tip 2203 to the optical measuring section 202 of the blood glucose meter 102. As a result, the blood glucose meter 102 detects that a new measuring tip 2203 is normally attached, and the "MEASURING" screen page P1729 is displayed on the LCD 203.

Figure 24H:
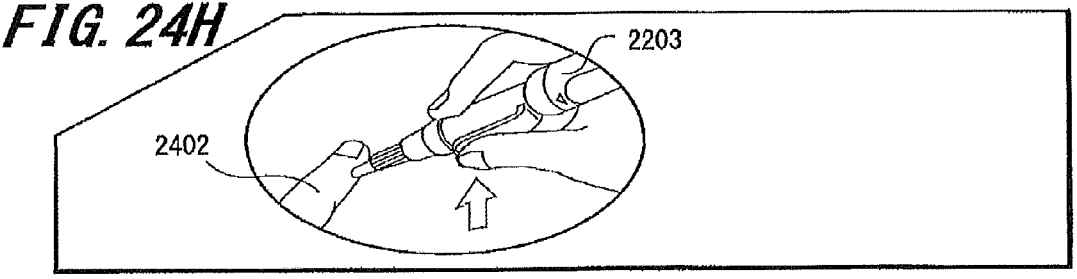

Description of the nurse's workflow will be continued below with reference to FIG. 24H.

The nurse 2202 punctures the lateral face of a fingertip 2402 of the patient 2205 with a puncture tool 2403. As a result, a tiny hole is punctured in the lateral face of fingertip 2402 by a needle, and blood is exuded from the hole.

Figure 24I:
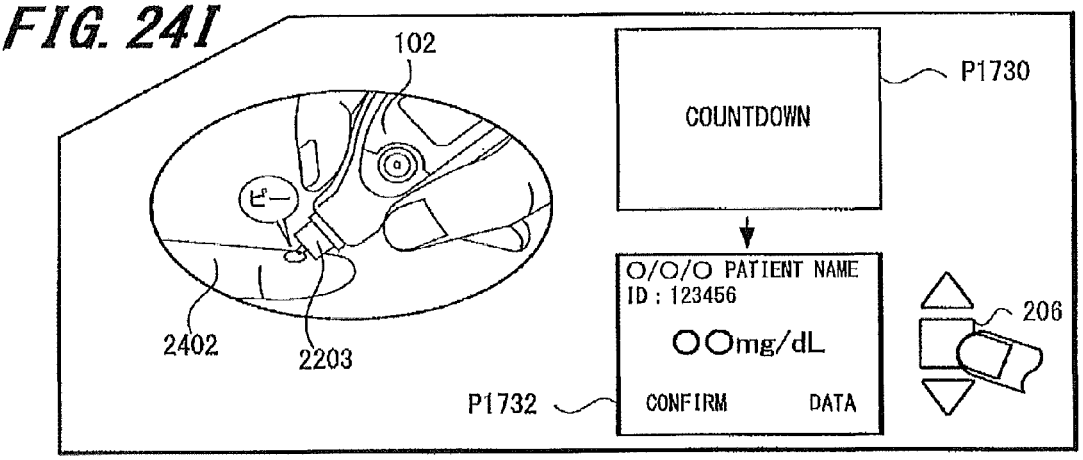

Description of the nurse's workflow will be continued below with reference to FIG. 24I.

The nurse 2202 soaks the blood exuded from the fingertip 2402 of the patient 2205 into the measuring tip 2203 of the blood glucose meter 102. As a result, by soaking the blood into the test piece 1127 inside the measuring tip 2203, the blood glucose meter 102 detects the quantity of the light reflected from the test piece 1127 and displays the "COUNTDOWN" screen page P1730 on the LCD 203.

When a predetermined time has elapsed since the "COUNTDOWN" screen page P1730 is displayed, the blood glucose measurement is performed, and the blood glucose level display screen page P1732 is displayed on the LCD 203.

The nurse 2202 confirms the contents of the display, selects "CONFIRM" with the Cursor keys 205, and presses the Enter key 206. As a result, in the case where there is unadministered drug(s), the insulin administration menu screen page P1733 is displayed on the LCD 203.

Figure 24J:
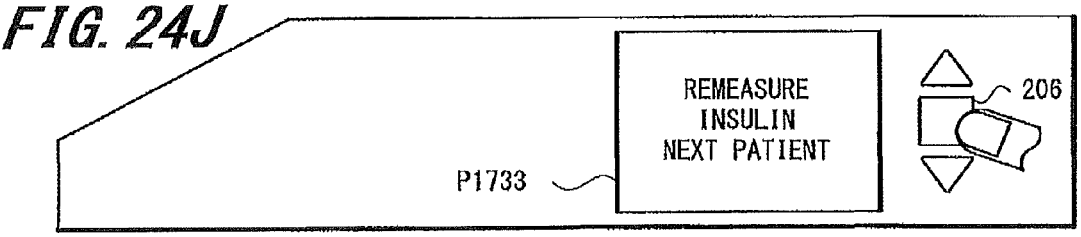

Description of the nurse's workflow will be continued below with reference to FIG. 24J.

In the state where the insulin administration menu screen page P1733 is being displayed on the LCD 203, the nurse 2202 selects "INSULIN" with the Cursor keys 205, and presses the Enter key 206.

As a result, the blood glucose measurement flag is set to "true", and the insulin dosage display screen page P1734 is displayed on the LCD 203 by the control section 1128 of the blood glucose meter 102.

Figure 25K:
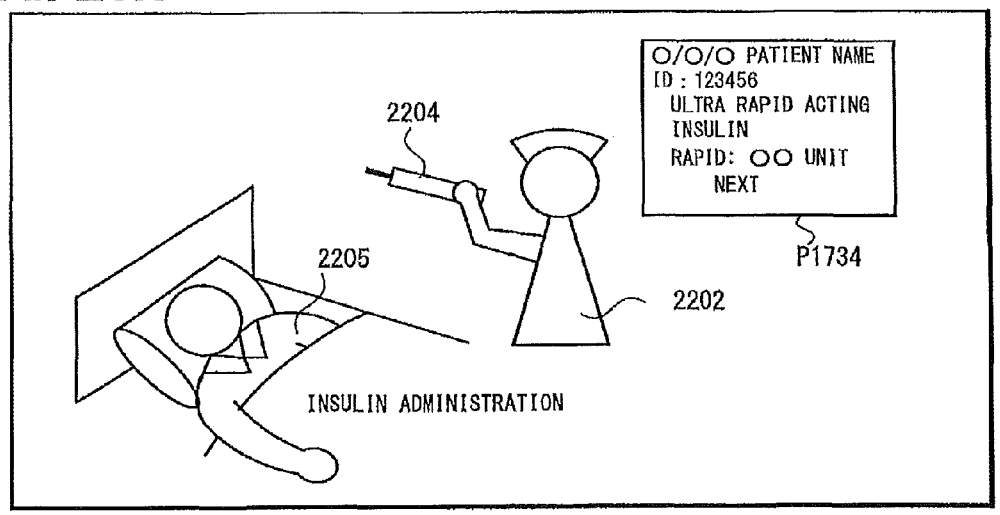
FIGS. 25K, 25L, 25M and 25N are schematic views showing nurse's workflow and attendant screen transition of the blood glucose meter.

Description of the nurse's workflow will be continued below with reference to FIG. 25K.

Following the content of the insulin dosage display screen page P1734 displayed on the LCD 203, the nurse 2202 administers insulin to the patient 2205 using the insulin syringe 2204.

Figure 25L:
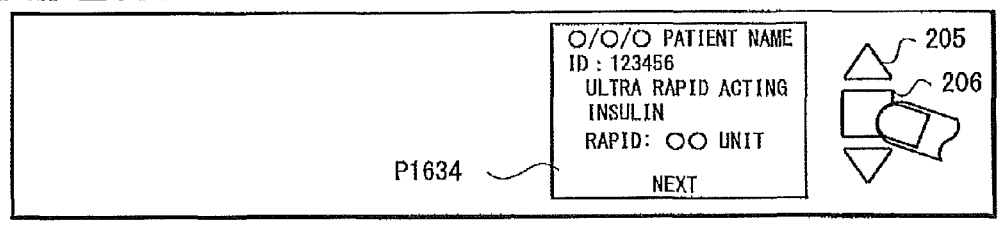

Description of the nurse's workflow will be continued below with reference to FIG. 25L.

After completing the insulin administration process, the nurse 2202 presses the Enter key 206.
As a result, the insulin dosage display flag is set to "true", and the administration selection screen page P1735 is displayed on the LCD 203 by the control section 1128 of the blood glucose meter 102.

Figure 25M:
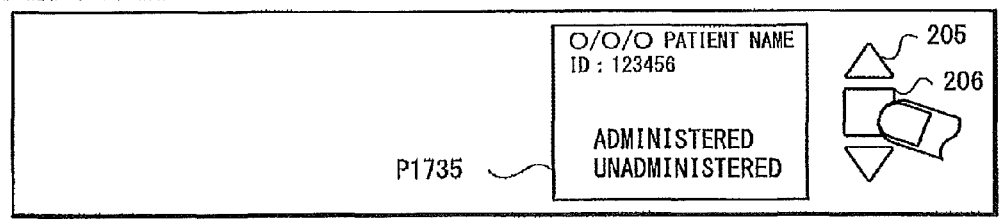

Description of the nurse's workflow will be continued below with reference to FIG. 25M.

In the state where the administration selection screen page P1735 is being displayed on the LCD 203, the nurse 2202 selects "ADMINISTERED" with the Cursor keys 205, and presses the Enter key 206.

As a result, the insulin administration confirmation flag is set to "true", and the "ADMINISTERED" screen page P1736 is displayed on the LCD 203 by the control section 1128 of the blood glucose meter 102.

Figure 25N:
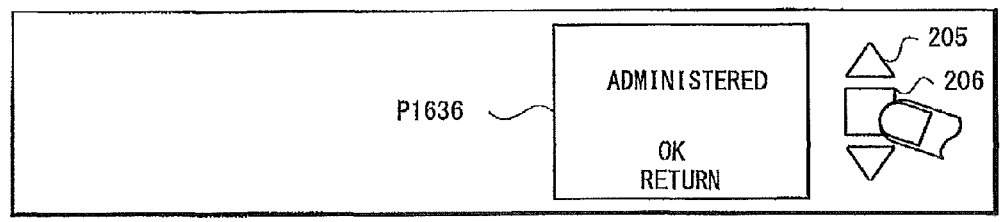

Description of the nurse's workflow will be continued below with reference to FIG. 25N.

In the state where the "ADMINISTERED" screen page P1736 is being displayed on the LCD 203, the nurse 2202 selects "OK" with the Cursor keys 205, and presses the Enter key 206.

Thereafter, in the case where there is unadministered drug(s), the administration confirmation screen page P1740 is displayed on the LCD 203, and further, after the screen has proceeded to the completion confirmation screen page P1742, the "NEXT PATIENT" screen page P1738 is displayed. Further, in the case where there is no unadministered drug, after the screen has proceeded to the administration confirmation screen page P1741, the "NEXT PATIENT" screen page P1738 is displayed.

Figure 26O:
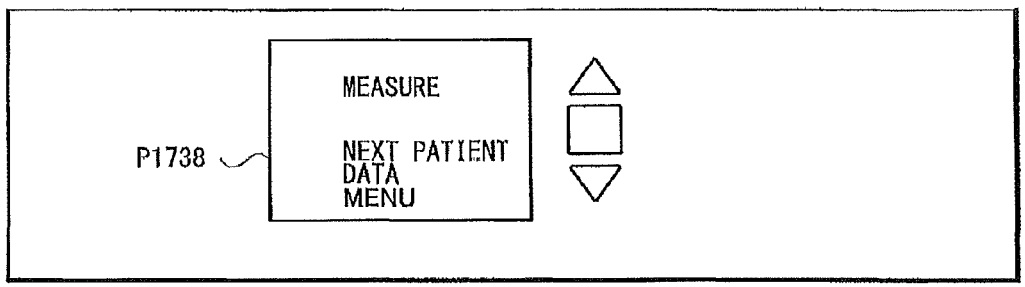
FIGS. 26O, 26P and 26Q are schematic views showing nurse's workflow and attendant screen transition of the blood glucose meter.

Description of the nurse's workflow will be continued below with reference to FIG. 26O.

In the state where the "NEXT PATIENT" screen page P1738 is being displayed on the LCD 203, the nurse 2202 selects "NEXT PATIENT" with the Cursor keys 205, and presses the Enter key 206.

Figure 23D:
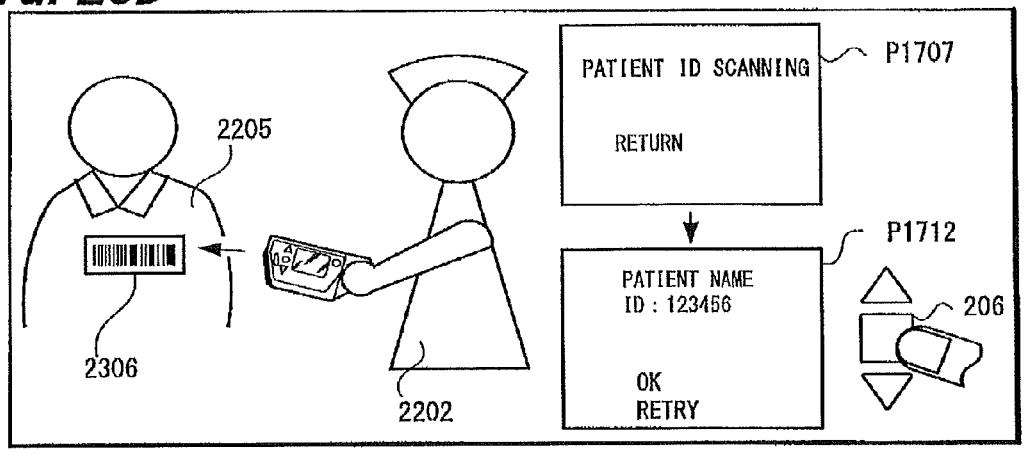
FIGS. 23D, 23E and 23F are schematic views showing nurse's workflow and attendant screen transition of the blood glucose meter.
Figure 23E:
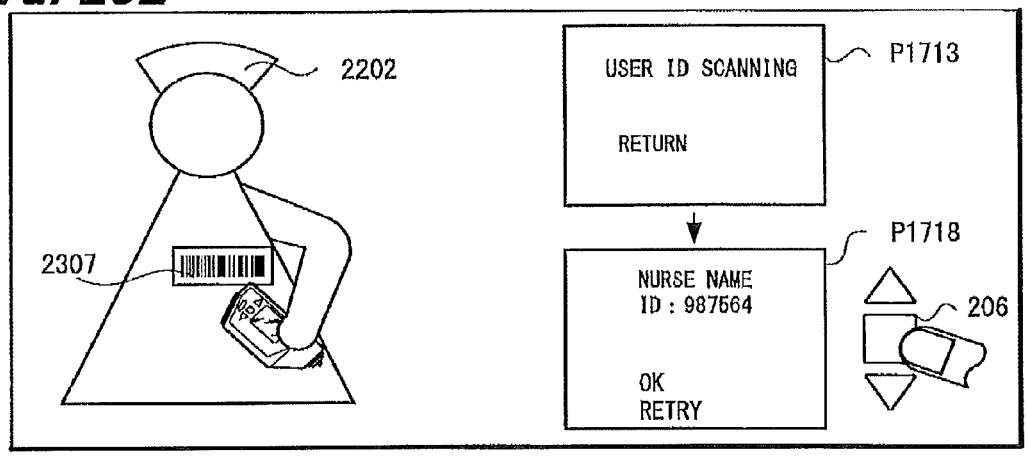
Figure 23F:
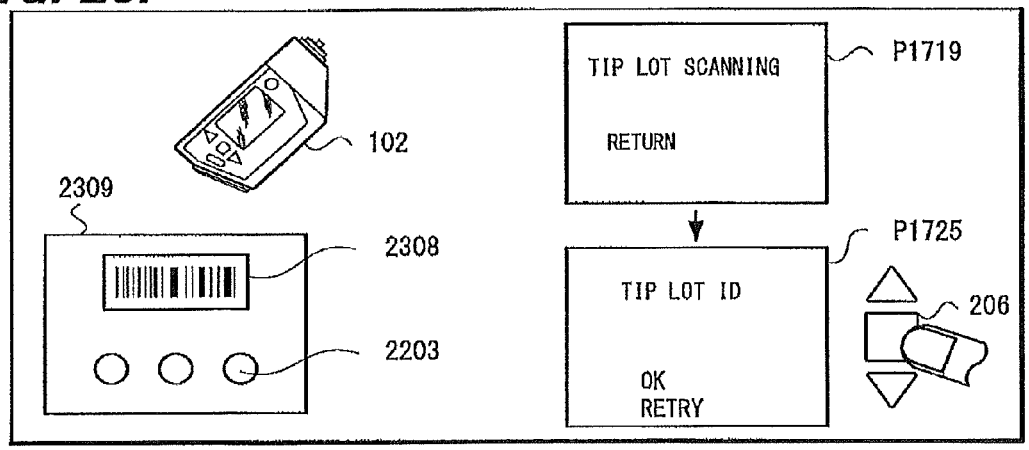

As a result, the content displayed on the LCD 203 returns to the patient ID scanning screen page P1707 shown in FIG. 23D to continue measurement process for the next patient.

Figure 26P:
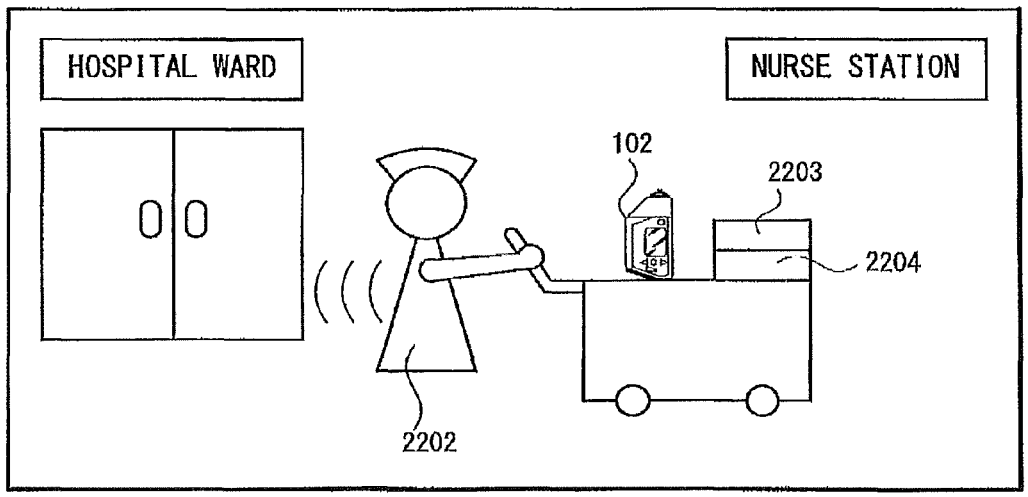

Description of the nurse's workflow will be continued below with reference to FIG. 26P.

After completing the blood glucose measurement process and insulin administration process for the patient 2205 in the hospital ward, the nurse 2202 returns to the nurse station.

Figure 26Q:
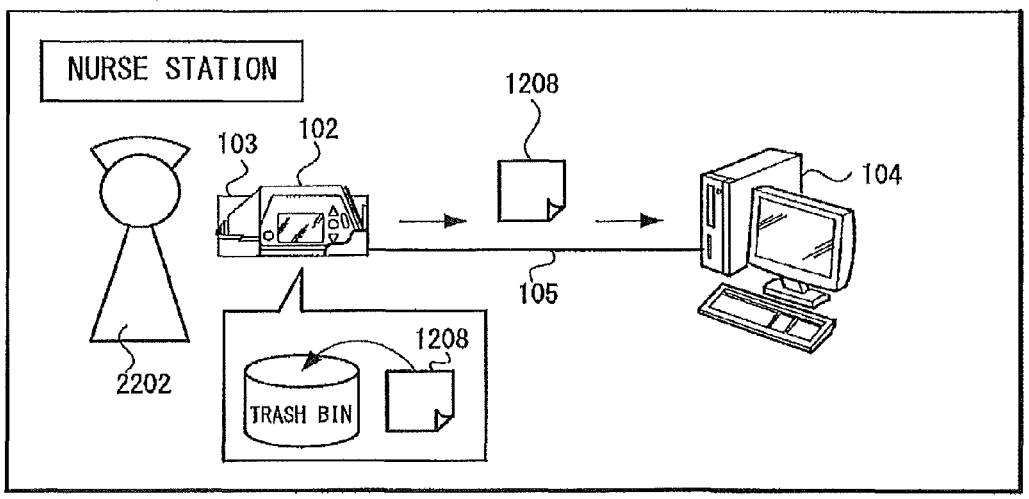

Description of the nurse's workflow will be continued below with reference to FIG. 26Q.

After returning to the nurse station from the hospital ward, the nurse 2202 mounts the blood glucose meter 102 on the cradle 103. As a result, the measurement data management device 104 recognizes the connection with the blood glucose meter 102 through the cradle 103, and requires the blood glucose meter 102 to transmit the measurement/prescription results table 1408.

Following the instruction from the measurement data management device 104, the blood glucose meter 102 transmits the measurement/prescription results table 1408 to the measurement data management device 104.

After normally receiving the measurement/prescription results table 1408, the measurement data management device 104 notifies the blood glucose meter 102 that the measurement/prescription results table 1408 has been normally received.

After receiving the report that "the measurement/prescription results table 1408 has been normally received" from the measurement data management device 104, the blood glucose meter 102 deletes the measurement/prescription results table 1408 stored in the nonvolatile storage 614.

Figure 27R:
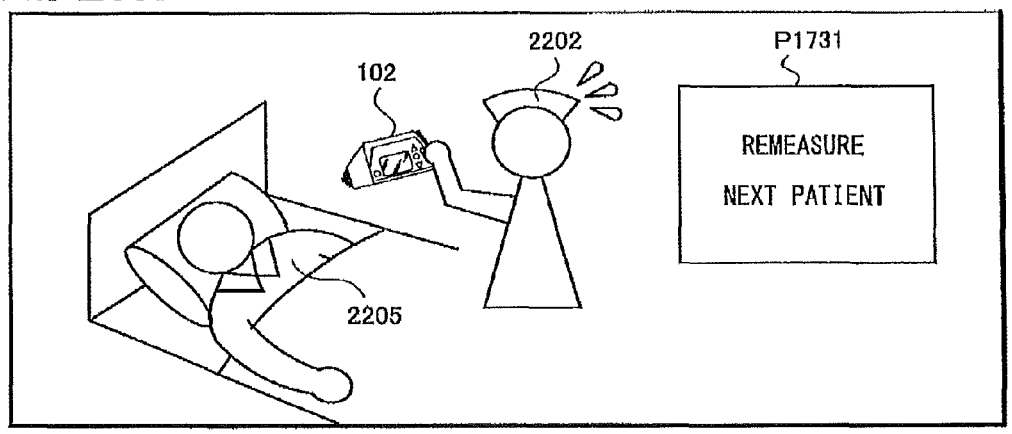
FIGS. 27R and 27S are schematic views showing nurse's workflow and attendant screen transition of the blood glucose meter.

Description of the nurse's workflow will be continued below with reference to FIG. 27R.

Even if the nurse 2202 is going to administer insulin again to the same patient by mistake, the insulin dosage display flag has been set to "true" and additionally recorded in the measurement/prescription results table 1408 when the administration selection screen page P1735 was displayed for administering insulin last time. The matter that the insulin dosage display flag has been set to "true" is detected by the control section 1128, and when performing blood glucose measurement, the blood glucose measurement menu screen page P1731 will be displayed on the LCD 203, and there is no item of "INSULIN" for being selected.

Thus, it is possible to prevent the accident of duplicated administration of insulin.

Figure 27S:
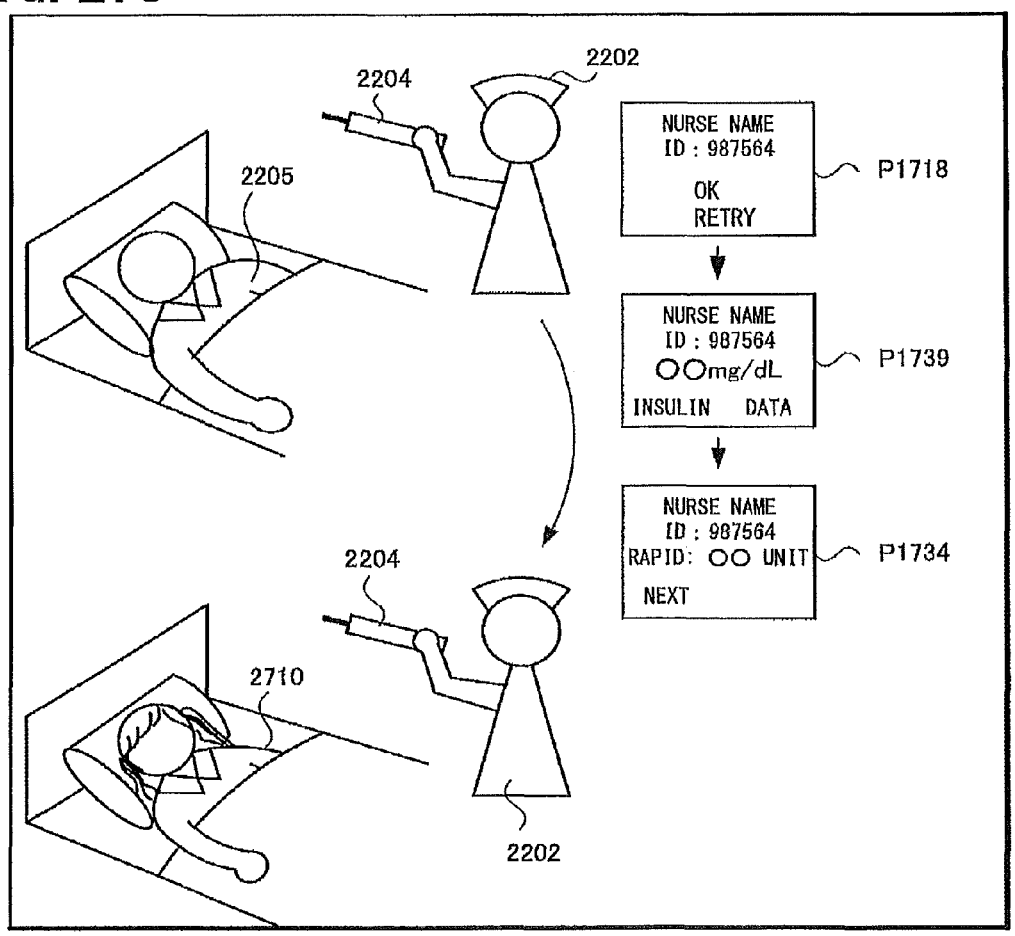

Description of the nurse's workflow will be continued below with reference to FIG. 27S.

After completing the blood glucose measurement of the patient 2205, in the state where the insulin administration menu screen page P1733 is displayed (see FIG. 24J), the nurse 2202 selects "NEXT PATIENT" with the Cursor keys 205, and presses the Enter key 206, so that the process proceeds to the blood glucose measurement process for another patient 2710. At this time, "true" is recorded in the "BLOOD GLUCOSE MEASUREMENT FLAG" field of the record of the patient 2205 of the measurement/prescription results table 1408. Thus, when scanning the patient ID of the patient 2205 and the nurse ID of the nurse 2202 for insulin prescription, the blood glucose level of the patient 2205 measured last time is read out from the measurement/prescription results table 1408 and displayed on the blood glucose level display screen page P1739.

Thus, the operation of performing "collective measurement" and then performing "collective administration" on a plurality of patients can be carried out safely and rapidly.

[Flow of Operation]

FIG. 28 is a flowchart showing the flow of overall operation of the blood glucose meter 102.

When the nurse 2202 presses the power switch 104 of the blood glucose meter 102 (S2801), the program stored in the ROM 603 is read by the CPU 502 to perform a predetermined initializing process (S2802), and then the initial screen page P1701 is displayed (S2803) to wait key operation (S2804).

If the item selected by the Enter key 206 is "PATIENT MEASUREMENT" (YES in Step S2805), the measurement process will be performed (S2806), and a series of operation will be terminated (S2810).

If the item selected by the Enter key 206 is "QC CHECK" (YES in Step S2807), the QC check will be performed (S2808), and a series of operation will be terminated (S2810).

If the item selected by the Enter key 206 is "SYSTEM SETUP" (NO in Step S2807), a setting process will be performed (S2809), and a series of operation will be terminated (S2810).

Note that, during the period while the power is turned on and the blood glucose meter 102 is not mounted on the cradle 103, the whole process is a loop process repeatedly performed from Step S2803, as indicated by a dotted arrow shown in FIG. 28.

FIGS. 29 and 30 are flowcharts showing the flow of the measurement process of the blood glucose meter 102. The flow of FIGS. 29 and 30 corresponds to Step S2806.

The flow of the measurement process of the blood glucose meter 102 will be described below with reference to FIG. 29.

When the process is started (S2901), the microcomputer operates as the measurement condition check section 1002. The control section 1128 causes the QC check section 1103 to operate so as to perform QC check (S2902).

Based on result of the QC check performed by the QC check section 1103, if the judging section 1106 judges that the QC check has not been performed within the predetermined date interval value 1104 (NO in Step S2903), the control section 1128 will display the QC warning screen page P1704 on the display unit 615 (S2904). The operation of the Enter key 206 will be waited (S2905), and if the Enter key 206 is operated, the QC check will be performed (S2906), and the process will be terminated (S2907).

In other words, Steps S2902 and S2903 are equal to Step S1751 of FIG. 18.

Based on result of the QC check performed by the QC check section 1103, if the judging section 1106 judges that the QC check has been performed within the predetermined date interval value 1104 (YES in Step S2903), the control section 1128 will cause the patient ID reading section 1107 to operate, the switch 1116 will be connected to the patient ID variable, the read information of the bar-code reader 208 will be stored in the patient ID variable 1108, and then the patient measurement screen page P1705 will be displayed (S2908). Thereafter, key operation is waited (S2909).

If the item selected by the Enter key 206 is "MEASURE" (YES in Step S2910), the control section 1128 will perform patient ID scanning process (S2914).

If the item selected by the Enter key 206 is "DATA" (YES in Step S2911), the control section 1128 will perform a data display process (S2912), and the screen will be returned to the patient measurement screen page P1705 (S2908). If the item selected by the Enter key 206 is "RETURN" (NO in Step S2911), the control section 1128 will terminate a series of process (S2913), and the screen will return to the initial screen page P1701 (S2803).

During the patient ID scanning process (S2914), if the item selected by operating the Enter key 206 is "OK" (YES in Step S2915), the control section 1128 will perform user ID scanning process (S2916).

During the user ID scanning process (S2916), if the item selected by operating the Enter key 206 is "OK" (YES in Step S2917), the control section 1128 will verify the blood glucose measurement flag and the insulin dosage display flag (S2918).

In the case where the blood glucose measurement flag is "true" and the insulin dosage display flag is "false" (YES in S2918), the control section 1128 will display the blood glucose level display screen page P1739 on the display unit 615 (S2919). Further, key operation is waited (S2920).

If the item selected by the Enter key 206 is "INSULIN" (YES in Step S2921), the process will proceed to a prescription information table search process (S3909) and a prescription display process (S3910) in the flow of the prescription display process shown in FIG. 39.

If the item selected by the Enter key 206 is "DATA" (NO in Step S2921), the process will proceed to the data display process (S2912).

In Step S2918, if the state of the blood glucose measurement flag and the insulin dosage display flag is not a combination of "the blood glucose measurement flag is 'true' and the insulin dosage display flag is 'false'" (NO in Step S2918), the tip lot scanning process will be performed (S2922).

In other words, Step S2918 is just Step S1752 of FIG. 19.

The flow of the measurement process of the blood glucose meter 102 following FIG. 29 will be described below with reference to FIG. 30.

Within the tip lot scanning process (S2922), if the item selected by operating the Enter key 206 is "OK" (YES in Step S2923), temperature check will be performed by the temperature check section 1119.

Based on the result of temperature check, if the temperature is not within an operation-guaranteed temperature range (NO in Step S3025), the control section 1128 will display the temperature error screen page P1726 on the display unit 615 (S3026) to wait key operation (S3027), and then process will be terminated (S3028).

In other words, Steps S3024 and S3025 are equal to Step S1753 of FIG. 19.

Based on the result of temperature check performed by the temperature check section 1119, if the temperature is within an operation-guaranteed temperature range (YES in Step S3025), tip attaching process will be performed (S3029).

Based on the result of the tip attaching process (S3029), if the attached measuring tip 2203 is a defective product (NO in Step S3030), the defective tip screen page P1728 will be displayed (S3031) to wait key operation (S3032), and the process will return to the tip lot scanning process (S2922).

Based on the result of the tip attaching process (S3029), if the attached measuring tip 2203 is a non-defective product (YES in Step S3030), the microcomputer will operate as the blood glucose measuring section 1003. Further, a measurement execution process will be performed (S3033).

After performing the measurement execution process (S3033), the blood glucose level display screen page P1732 is displayed (S3034) to wait key operation (S3035).

If the item selected by operating the Enter key 206 is "DATA" (NO in Step S3036), the process will proceed to the data display process (S2912).

If the item selected by operating the Enter key 206 is "CONFIRM" (YES in Step S3036), the control section 1128 will confirm all insulin administration confirmation flags recorded in the record of the patient in the measurement/prescription results table 1408.

In Step S3037, when even one of the insulin administration confirmation flags is "false", i.e., when insulin administration processes necessary for the patient are not all completed, the process will proceed to prescription display process (S3038).

At the end of the prescription display process (S3038), if the item selected by operating the Enter key 206 (Step S3914 of FIG. 39) is "NEXT PATIENT" (YES in Step S3039), the Process will return to patient ID scanning process (S2914).

At the end of the prescription display process (S3038), if the item selected by operating the Enter key 206 (Step S3914 of FIG. 39) is "DATA" (NO in Step S3039 and YES in Step S3040), the process will proceed to data display process (S2912).

At the end of the prescription display process (S3038), if the item selected by operating the Enter key 206 (Step S3914 of FIG. 39) is "MENU" (NO in Step S3039 and NO in Step S3040), the process will be terminated (S3041).

In Step S3037, if all of the insulin administration confirmation flags are "true", i.e., if all of the insulin administration processes necessary for the patient are completed (NO in Step S3037), the blood glucose measurement menu screen page P1731 will be displayed on the display unit (S3042) to wait key operation (S3043).

If the item selected by the Enter key 206 is "REMEASURE" (YES in Step S3044), the blood glucose measurement flag will be set to "false" (S3045), and the process will return to the patient ID scanning process (S2914).

If the item selected by the Enter key 206 is "NEXT PATIENT" (NO in Step S3044), the blood glucose measurement flag will be set to "true" (S3046), and the process will return to the patient ID scanning process (S2914).

FIGS. 31 and 32 are flowcharts showing the flow of the patient ID scanning process. The flow of FIGS. 31 and 32 corresponds to Step S2914 of FIG. 29.

The flow of the patient ID scanning process of the blood glucose meter 102 will be described below with reference to FIG. 31.

When the process is started (S2901), the patient ID scanning screen page P1707 is displayed (S3102) to wait bar-code or key operation (S3103).

If the item selected by operating the Enter key 206 is "RETURN" (YES in Step S3104), the process will be terminated (S3105). Further, the content of the selection item at this time ("RETURN") will be reflected by the judgment of Step S2915 (NO in Step S2915), and the screen will be returned to the patient measurement screen page P1705 (S2908).

If the result of the bar-code reader or key operation is not "RETURN" (NO in Step S3104), whether or not the bar-code has been read will be verified (S3106). If the bar-code has been normally read (YES in Step S3106), the read data deemed to be the patient ID will be compared with the patient table 1109 (S3107). As a result, if the read data does not exist in the patient table 1109 (NO in Step S3108), the "UNREGISTERED" screen page P1708 will be displayed (S3109) to wait key operation (S3110), and the screen will be returned to the patient ID scanning screen page P1707 (S3102).

In Step S3107, if the read data exists in the patient table 1109 (YES in Step S3108), the patient name display screen page P1712 will be displayed (S3111) to wait key operation (S3112).

If the item selected by operating the Enter key 206 is "OK" (YES in Step S3113), the process will be terminated (S3114). Further, the content of the selection item at this time ("OK") will be reflected by the judgment of Step S2915 (YES in Step S2915), and the process will proceed to user ID scanning process (S2916).

The flow of the patient ID scanning process of the blood glucose meter 102 will be further described below with reference to FIG. 32.

In Step S3106, if the bar-code has not been normally read (NO in Step S3106), an error counter inside the control section 1128 will be incremented (S3215).

Next, whether or not the value of the error counter exceeds two is verified (S3216). If the value of the error counter does not exceed two (NO in Step S3216), the read error screen page P1709 will be displayed (S3217) to wait key operation (S3218), and the screen will be returned to the patient ID scanning screen page P1707 (S3102).

If the value of the error counter exceeds two (YES in Step S3216), the read error screen page P1710 will be displayed (S3219) to wait key operation (S3220).

If the item selected by operating the Enter key 206 in Step S3220 is "RETRY" (NO in Step S3221) instead of "SELECT FROM LIST", the screen will be returned to the patient ID scanning screen page P1707 (S3102).

If the item selected by operating the Enter key 206 in Step S3220 is "SELECT FROM LIST" (YES in Step S3221), the patient list screen page P1711 will be displayed (S3222) to wait key selecting operation (S3223). Further, the patient ID selected by the user is determined as the patient ID to be subjected to the blood glucose measurement (S3224), and the process is returned to Step S3111.

FIGS. 33 and 34 are flowcharts showing the flow of the user ID scanning process. The flow of FIGS. 33 and 34 corresponds to Step S2916 of FIG. 29.

The flow of the user ID scanning process of the blood glucose meter 102 will be described below with reference to FIG. 33.

When the process is started (S3301), the user ID scanning screen page P1713 is displayed (S3302) to wait bar-code or key operation (S3303).

If the item selected by operating the Enter key 206 is "RETURN" (YES in Step S3304), the process will be terminated (S3305). Further, the content of the selection item at this time ("RETURN") will be reflected by the judgment of Step S2917 (NO in Step S2917), and the screen will be returned to the patient measurement screen page P1705 (S2908).

If the result of the bar-code reader or key operation is not "RETURN" (NO in Step S3304), whether or not the bar-code has been read will be verified (S3306). If the bar-code has been normally read (YES in Step S3306), the read data deemed to be the patient ID will be compared with the user table (S3307). As a result, if the read data does not exist in the user table (NO in Step S3308), the "UNREGISTERED" screen page P1714 will be displayed (S3309) to wait key operation (S3310), and the screen is returned to the user ID scanning screen page P1713 (S3302).

In Step S3307, if the read data exists in the user table (YES in Step S3308), the user name display screen page P1718 will be displayed (S3311) to wait key operation (S3312).

If the item selected by operating the Enter key 206 is "OK" (YES in Step S3313), the process will be terminated (S3314). Further, the content of the selection item at this time ("OK") will be reflected by the judgment of Step S2917 (YES in Step S2917), and the process will proceed to Step S2918.

The flow of the user ID scanning process of the blood glucose meter 102 will be further described below with reference to FIG. 34.

In Step S3306, if the bar-code has not been normally read (NO in Step S3306), an error counter inside the control section 1128 will be incremented (S3415).

Next, whether or not the value of the error counter exceeds two is verified (S3416). If the value of the error counter does not exceed two (NO in Step S3416), the read error screen page P1715 will be displayed (S3417) to wait key operation (S3418), and the screen will be returned to the user ID scanning screen page P1713 (S3302).

If the value of the error counter exceeds two (YES in Step S3416), the read error screen page P1716 will be displayed (S3419) to wait key operation (S3420).

If the item selected by operating the Enter key 206 in Step S3420 is "RETRY" (NO in Step S3421) instead of "SELECT FROM LIST", the screen will be returned to the user ID scanning screen page P1713 (S3302).

If the item selected by operating the Enter key 206 in Step S3420 is "SELECT FROM LIST" (YES in Step S3421), the user list screen page P1717 will be displayed (S3422) to wait key selecting operation (S3423). Further, the user ID selected by the user is determined as the user ID who is going to perform the blood glucose measurement (S3424), and the process is returned to Step S3311.

FIGS. 35 and 36 are flowcharts showing the flow of the tip lot scanning process. The flow of FIGS. 35 and 36 corresponds to Step S2922 of FIG. 29.

The flow of the tip lot scanning process of the blood glucose meter 102 will be described below with reference to FIG. 35.

When the process is started (S3501), the tip lot scanning screen page P1719 is displayed (S3502) to wait bar-code or key operation (S3503).

If the item selected by operating the Enter key 206 is "RETURN" (YES in Step S3504), the process will be terminated (S3505). Further, the content of the selection item at this time ("RETURN") will be reflected by the judgment of Step S2923 (NO in Step S2923), and the screen will be returned to the patient measurement screen page P1705 (S2908).

If the result of the bar-code reader or key operation is not "RETURN" (NO in Step S3504), whether or not the bar-code has been read will be verified (S3506). If the bar-code has been normally read (YES in Step S3606), the read data deemed to be the tip lot will be compared with the tip lot table (S3507). As a result, if the read data does not exist in the tip lot table (NO in Step S3808), the "UNREGISTERED" screen page P1720 will be displayed (S3509) to wait key operation (S3510), and the screen will be returned to the tip lot scanning screen page P1719 (S3502).

In Step S3507, if the read data exists in the tip lot table (YES in Step S3508), whether or not the lot is within validity date will be verified (S3511). If validity date is expired (NO in Step S3511), the expiration error screen page P1721 will be displayed (S3512) to wait key operation (S3510), and the screen will be returned to the tip lot scanning screen page P1719 (S3502).

If it is judged that the lot is within validity date (YES in Step S3511), the tip lot display screen page P1725 will be displayed (S3513) to wait key operation (S3514).

If the item selected by operating the Enter key 206 is "OK" (YES in Step S3515), the process will be terminated (S3516). Further, the content of the selection item at this time ("OK") will be reflected by the judgment of Step S2923 (YES in Step S2923), and the process will proceed to Step S3024.

The flow of the tip lot scanning process of the blood glucose meter 102 will be further described below with reference to FIG. 36.

In Step S3506, if the bar-code has not been normally read (NO in Step S3506), an error counter inside the control section 1128 will be incremented (S3617).

Next, whether or not the value of the error counter exceeds two is verified (S3618). If the value of the error counter does not exceed two (NO in Step S3618), the read error screen page P1722 will be displayed (S3619) to wait key operation (S3620), and the screen will be returned to the tip lot scanning screen page P1719 (S3502).

If the value of the error counter exceeds two (YES in Step S3618), the read error screen page P1723 will be displayed (S3621) to wait key operation (S3622).

If the item selected by operating the Enter key 206 in Step S3622 is "RETRY" (NO in Step S3622) instead of "SELECT FROM LIST", the screen will be returned to the tip lot scanning screen page P1719 (S3502).

If the item selected by operating the Enter key 206 in Step S3622 is "SELECT FROM LIST" (YES in Step S3623), the tip lot list screen page P1724 will be displayed (S3624) to wait key selecting operation (S3625). Further, the tip lot selected by the user is determined as the lot of the measuring tip 2203 to be used to perform the blood glucose measurement (S3626), and the process is returned to Step S3513.

FIG. 37 is a flowchart showing the flow of the tip attaching process. The flow of FIG. 37 corresponds to Step S3029 of FIG. 30.

When the process is started (S3701), the control section 1128 displays the "PLEASE ATTACH A TIP" screen page P1727 on the display unit 615 (S3702) and causes the tip attachment check section 1123 to operate. The control section 1128 performs on-control of the switch 1126 to cause the D/A converter 611 to convert the adjustment value data 925 into an analog voltage to drive the driver 610 to control the light emission of the light-emitting diode 609. Further, the reflected light from the test piece 1127 is received by the phototransistor 612, and the reflected light measurement is performed (S3703).

The reflected light data inputted to the tip attachment detection section 1124 from the phototransistor 612 through the A/D converter 613 is continuously polled (S3704). If the phototransistor 612 detects the reflected light (YES in Step S3704), the process will be terminated (S3705).

FIG. 38 is a flowchart showing the flow of the measurement execution process. The flow of FIG. 38 corresponds to Step S3033 of FIG. 30.

When the process is started (S3801), the control section 1128 displays the "MEASURING" screen page P1729 on the display unit 615 (S3802).

Whether or not there is a change in reflected light data obtained from the phototransistor 612 is polled (S3803).

If a change in quantity of the reflected light is detected (YES in Step S3803), a timer inside the control section 1128 is started (S3804), and the "COUNTDOWN" screen page P1730 is displayed on the display unit 615 (S3805).

When a preset time (12 seconds±α) has elapsed (YES in Step S3806), the quantity of the reflected light will be measured, the blood glucose level will be calculated based on the quantity of the reflected light (S3807), and the process will be terminated (S3808).

FIGS. 39 and 40 are flowcharts showing the flow of the prescription display process. The flow of FIGS. 39 and 40 corresponds to Step S3038 of FIG. 30.

The flow of the prescription display process of the blood glucose meter 102 will be described below with reference to FIG. 39.

When the process is started (S3901), the insulin administration menu screen page P1733 is displayed (S3902) to wait key operation (S3903).

If the item selected by operating the Enter key 206 in Step S3903 is "INSULIN" (YES in Step S3904), the blood glucose measurement flag will be set to "true" (S3908).

If the item selected by operating the Enter key 206 in Step S3903 is "REMEASURE" (YES in Step S3905), the blood glucose measurement flag will be set to "false" (S3906). If the item selected by operating the Enter key 206 in Step S3903 is "NEXT PATIENT" (NO in Step S3905), the blood glucose measurement flag will be set to "true" (S3907).

After the process of Steps S3906 and S3907, the process is returned to the patient ID scanning process (S2914).

After the process of Step S3908, the control section 1128 controls the search section 1503 to search the prescription information table 1502 (S3909), and the insulin dosage display screen page P1734 is displayed (S3910) to wait key operation (S3911).

If the Enter key 206 is pressed by the user, the administration selection screen page P1735 will be displayed (S3912), and the insulin dosage display flag will be set to "true" (S3913) to wait key operation (S3914).

The flow of the prescription display process of the blood glucose meter 102 will be further described below with reference to FIG. 40.

If the item selected by operating the Enter key 206 in Step S3914 is "ADMINISTERED" (YES in Step S4015), the "ADMINISTERED" screen page P1736 will be displayed (S4016) to wait key operation (S4017).

If the item selected by operating the Enter key 206 in Step S4017 is "RETURN" (NO in Step S4018), the administration selection screen page P1735 will be displayed again (S3912), and the insulin dosage display flag regarding the currently displayed drug will be set to "true" (S3913) to wait key operation (S3914).

If the item selected by operating the Enter key 206 in Step S4017 is "OK" (YES in Step S4018), the insulin dosage display flag regarding the currently displayed drug will be set to "true" (S4019), and the process will proceed to Step S4020.

If the item selected by operating the Enter key 206 in Step S3914 is "UNADMINISTERED" (NO in Step S4015), the "UNADMINISTERED" screen page P1737 will be displayed (S4021) to wait key operation (S4022).

If the item selected by operating the Enter key 206, in Step S4022 is "RETURN" (NO in Step S4023), the administration selection screen page P1735 will be displayed again (S3912), and the insulin dosage display flag regarding the currently displayed drug will be set to "true" (S3913) to wait key operation (S3914).

If the item selected by operating the Enter key 206 in Step S4022 is "OK" (YES in Step S4023), the process will proceed to Step S4020. In other words, the insulin dosage display flag regarding the currently displayed drug remains "false".

After Steps S4019 and S4023, the control section 1128 confirms the prescription of the present patient. The control section 1128 confirms all records in the "INSULIN ADMINISTRATION INFORMATION" field in the record of the patient. In other words, the control section 1128 confirms the insulin administration confirmation flags regarding all prescriptions. As a result, when even one of the "INSULIN ADMINISTRATION CONFIRMATION FLAG" field is "false", i.e., when even one drug unadministered to the patient exists (YES in Step S4020), the administration confirmation screen page P1740 will be displayed (S4024) to wait key operation (S4025).

If the item selected by operating the Enter key 206 in Step S4025 is "RETURN" (NO in Step S4026), the prescription information table 1502 will be searched again (S3909), and the insulin dosage display screen page P1734 will be displayed (S3910) to wait key operation (S3911).

If the item selected by operating the Enter key 206 in Step S4025 is "OK" (YES in Step S4026), the completion confirmation screen page P1742 will be displayed (S4027) to wait key operation (S4028).

If the item selected by operating the Enter key 206 in Step S4028 is "RETURN" (NO in Step S4029), the process will be returned to Step S4020.

If the item selected by operating the Enter key 206 in Step S4028 is "YES" (YES in Step S4029), the "NEXT PATIENT" screen page P1738 will be displayed (S4030), and the process will be terminated (S4031).

In Step S4020, the control section 1128 confirms all records in the "INSULIN ADMINISTRATION INFORMATION" field in the record of the patient, namely the control section 1128 confirms the insulin administration confirmation flags regarding all prescriptions. Based on the result of the confirmation performed by the control section 1128, if all "INSULIN ADMINISTRATION CONFIRMATION FLAG" fields are "true", namely if all drugs are administered to the patient (NO in Step S4020), the administration confirmation screen page P1741 will be displayed (S4032) to wait key operation (S4033).

In Step S4033, since "COMPLETION" is the only item possible to be selected, thereafter the "NEXT PATIENT" screen page P1738 is displayed, and the process is terminated.

The present embodiment includes application examples such as the following.

Figure 20:
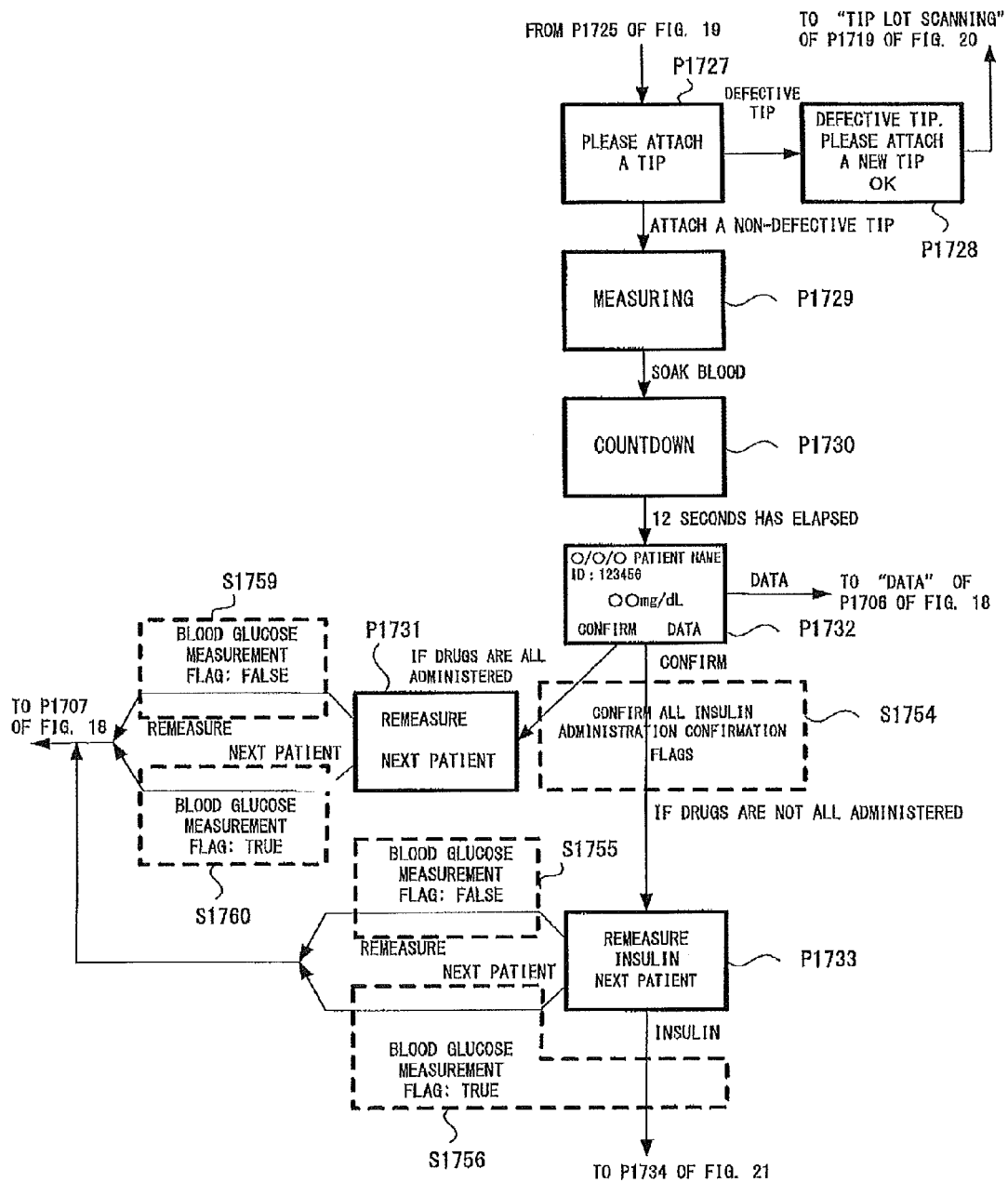
FIG. 20 is a partly enlarged view of the state transition diagram.

(1) In Step S1754 of FIG. 20 and Step S3037 of FIG. 30, the insulin administration confirmation flags are used as a basis for making a judgment for preventing duplicated administration of insulin. Instead of the insulin administration confirmation flag, the insulin dosage display flag can be used as a basis for making a judgment for preventing duplicated administration of insulin.

Figure 41:
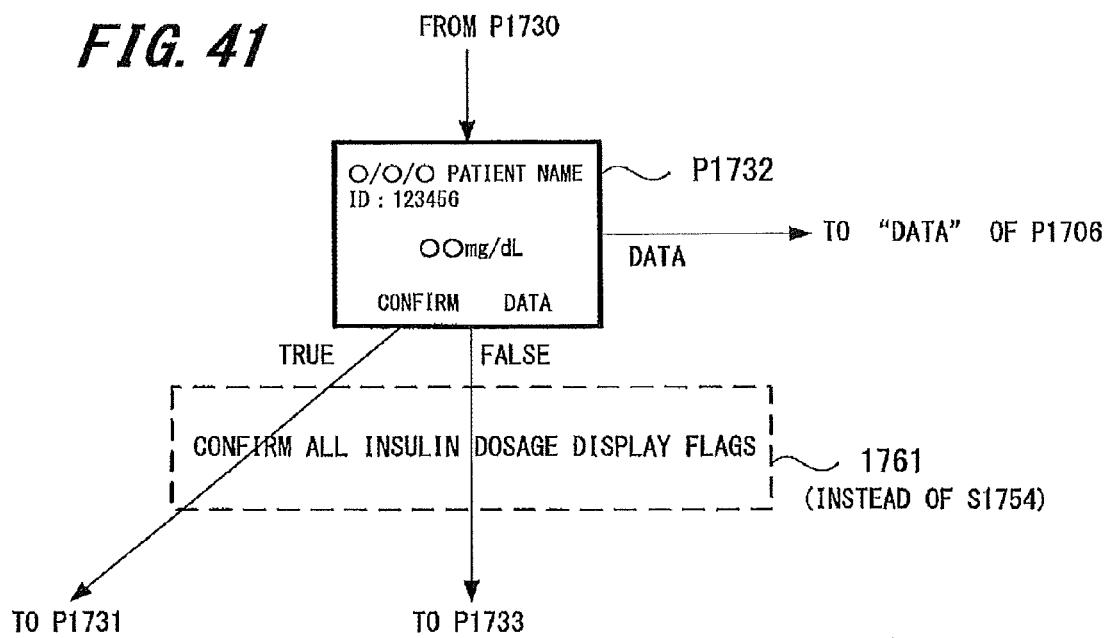
FIG. 41 is a partly enlarged view of screen transition diagram based on an application example.

FIG. 41 is a partial view extracted from a screen transition diagram based on the application example. FIG. 41 corresponds to the substitution of Step S1754 of FIG. 20. To be specific, after the "COUNTDOWN" screen page P1730 of FIG. 20 is displayed, the state of the insulin dosage display flags is confirmed in Step S4154 (instead of confirming the insulin administration confirmation flags in Step S1754), and the process proceeds to the blood glucose level display screen page P1731 or P1733.

Figure 42:
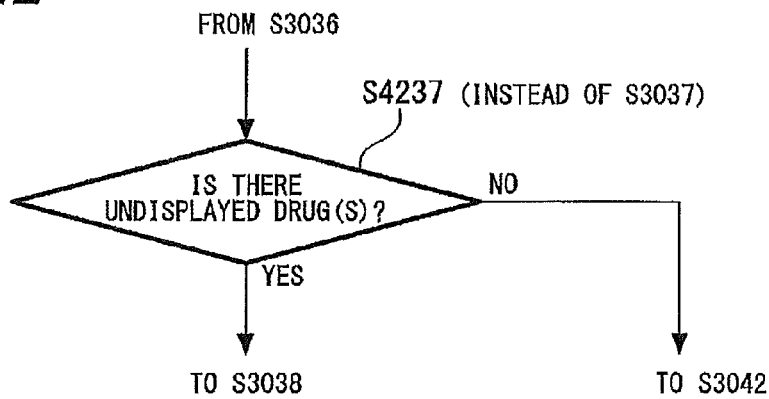
FIG. 42 is a partly enlarged view of the flowchart based on the application example.

FIG. 41 is a partial view extracted from a flowchart based on the application example. FIG. 42 corresponds to the substitution of Step S3037 of FIG. 30. To be specific, the state of the insulin dosage display flags is confirmed in Step S4237 (instead of confirming the "true" and "false" of the insulin administration confirmation flags in Step S3037), and the process proceeds to Step P3038 or P3042.

Figure 43:
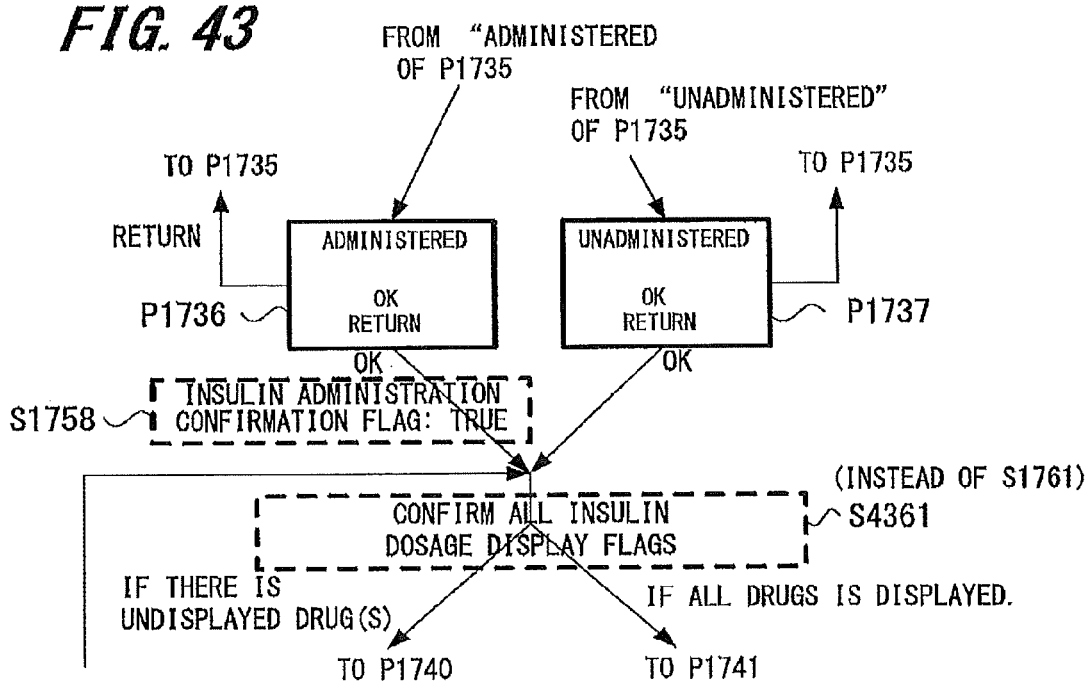
FIG. 43 is a partly enlarged view of screen transition diagram based on the application example.

FIG. 43 is a partial view extracted from a screen transition diagram based on the application example. FIG. 43 corresponds to the substitution of Step S1761 of FIG. 21. To be specific, after the "ADMINISTERED" screen page P1736 is displayed and "OK" is selected, or after the "UNADMINISTERED" screen page P1737 is displayed and "OK" is selected, the state of the insulin dosage display flags is confirmed in Step S4361 (instead of confirming the insulin administration confirmation flags in Step S1761), and the process proceeds to any the administration confirmation screen page P1740 or administration confirmation screen page P1741.

Figure 44:
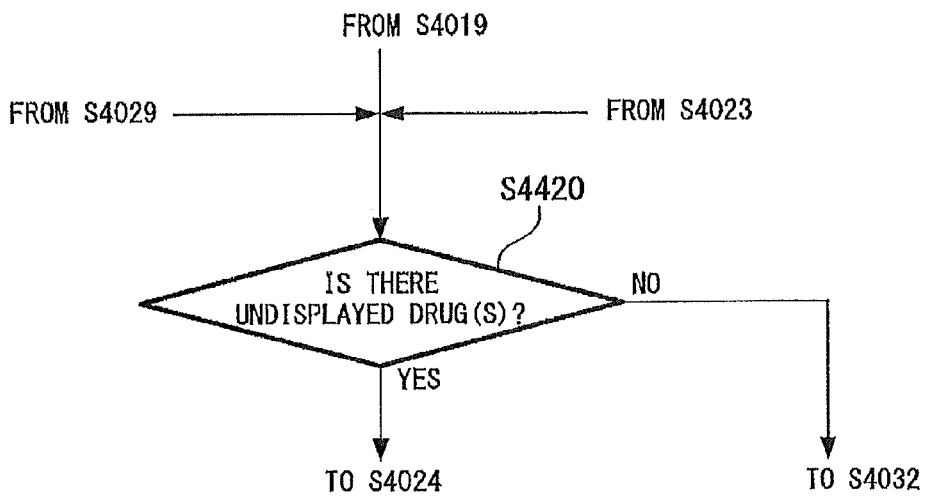
FIG. 44 is a partly enlarged view of the flowchart based on the application example.

FIG. 44 is a partial view extracted from a flowchart based on the application example. FIG. 44 corresponds to the substitution of Step S4020 of FIG. 40. To be specific, the state of the insulin dosage display flags is confirmed in Step S4420 (instead of confirming the "true" and "false" of the insulin administration confirmation flags in Step S4020), and the process proceeds to Step P4024 or P4032.

(2) By setting the value of the "PRESCRIPTION NUMBER" field of the measurement/prescription table 1602 for being previously transferred to the blood glucose meter to "1" so as not to record data in the record of the patient corresponding to the prescription information table 1502, it is possible to only perform blood glucose measurement to the patient.
(3) The communication method between the blood glucose meter and the cradle is not limited to IrDA, but can be other communication methods such as short-distance non-contact electromagnetic induction using an IC card, Bluetooth (registered trademark), wireless LAN and the like. Further, there is another possible configuration in which the cradle is provided with no communication function, and the blood glucose meter and the personal computer directly communicate with other via a wireless LAN or the like.
(4) The configuration of the fields of the prescription information table 1502 is not limited to the configuration shown in FIG. 16C.

Similar to the "INSULIN ADMINISTRATION INFORMATION" field of the measurement/prescription results table 1408, if a variable-length "CLASSIFICATION INFORMATION" field having a plurality of records each including a "BLOOD GLUCOSE LEVEL RANGE" field and a "PRESCRIPTION" field is provided, each one record can be configured by a "PATIENT ID" field, a "CLASSIFICATION NUMBER" field, a "DRUG NAME" field and a "CLASSIFICATION INFORMATION" field. By configuring the prescription information table 1502 by such fields, number of the "PATIENT ID" fields, the "CLASSIFICATION NUMBER" fields and the "DRUG NAME" field having the same value can be reduced.

Further, by arranging the records in the order of the patient table 1109 and referring to the value of the "PRESCRIPTION NUMBER" field, the "PATIENT ID" field can be omitted.
(5) The configuration of the fields of the measurement/prescription table 1602 is not limited to the configuration shown in FIG. 16A.

If the fields of the prescription information table 1502 are configured in a manner in which the classification number of the patient ID can be grasped by narrowing down with the patient ID as shown in FIG. 16C, the "PRESCRIPTION NUMBER" field of the measurement/prescription table 1602 can be omitted.

The information about what concrete operations the user of the blood glucose meter should perform on the patient is stored in the measurement/prescription table 1602 and the prescription information table 1502, such as whether or not the user should perform blood glucose measurement on the patient, whether or not the user should perform insulin administration on the patient, what dosage of insulin should be administered to the patient when performing insulin administration, and the like. The configuration of the fields of the measurement/prescription table 1602 and the prescription information table 1502 is not limited to the configuration shown in FIGS. 16A and 16C, but can be others as long as "the information about what concrete operations the user of the blood glucose meter should perform on the patient" can be correctly expressed.

The blood glucose meter has been disclosed in the present embodiment.

The blood glucose measurement flag is set to "true", and the blood glucose level and the patient ID is recorded in the measurement/prescription results table.

Thereafter, when selecting the "NEXT PATIENT", in "false" state, the record of the next patient is recorded in the measurement/prescription results table in the same manner while the insulin administration confirmation flag keeps in "false" state.

After the blood glucose measurement performed on the patient has been completed, when scanning the patient ID again, a record of the patient ID will be found in the measurement/prescription results table, wherein the record shows that the "BLOOD GLUCOSE MEASUREMENT FLAG" field is "true" and the "INSULIN ADMINISTRATION CONFIRMATION FLAG" field is "false". Further, after searching the prescription information table 1502 with the blood glucose level to obtain the prescription data, the data is displayed on the display unit.

Owing to this function, "collective measurement and collective prescription" can be achieved safely, reliably and rapidly.

Once the insulin dosage display flag is set to "true", even if the blood glucose measurement is performed on the patient again by mistake, the screen page for performing insulin administration will not be displayed again.

Owing to this function, it is possible to reliably prevent the accident of duplicated administration of insulin.

Although the present embodiment of the present invention is described above, it should be noted that the present invention is not limited to the above embodiment but includes various other modifications and applications without departing from the spirit of the claims of the present invention.

EXPLANATION OF REFERENCE NUMERALS

101 blood glucose measuring system
102 blood glucose meter (blood glucose measuring device)
103 cradle
104 measurement data management device
105 USB cable
202 optical measuring section
212 measuring tip
204 power switch
205 Cursor keys
206 Enter key
207 Bar-code key
208 bar-code reader
203 LCD
209 power terminal
210 infrared communication window
211 battery lid
302 eject lever
402 charging terminal
403 infrared communication window
619, 719 infrared light-emitting diode
620, 720 phototransistor
602 CPU
603 ROM
605 bus
606 thermistor
607 calendar clock
608 operating section
609 light-emitting diode
610 driver
611 D/A converter
612 phototransistor
613 A/D converter
614 nonvolatile storage
615 display unit
616 buzzer
617 infrared communication section
618 power circuit
702 CPU
703 ROM
704 RAM 717 infrared communication section
706 USB interface
718 charging circuit
705 bus
902 bus
903 CPU
904 ROM
905 RAM
906 nonvolatile storage
907 display unit
908 USB interface
909 operating section
1002 measurement condition check section
1003 blood glucose measuring section
1004 prescription data display section
1007 data communicating section
1103 QC check section
1104 predetermined date interval value
1105 QC check record
1106 judging section
1107 patient ID reading section
1108 patient ID variable
1109 patient table
1110 search section
1111 user ID reading section
1112 user ID variable
1113 user table
1114 search section
1115 tip lot reading section
1116 tip lot variable
1117 tip lot table
1118 judging section
1119 temperature check section
1120 temperature judging section
1122 temperature variable
1123 tip attachment check section
1124 tip attachment detection section
1125 adjustment value
1127 test piece
1128 control section
1202, 1203 comparator
1204 upper limit
1205 lower limit
1206 AND gate
1302, 1303 sample-and-hold circuit
1304 clock
1305 comparator
1306 switch
1307 comparator
1308 threshold
1309 rising edge detection section
1402 adjustment value data
1403 switch
1404 detection section
1405 blood glucose level variable
1406 judging section
1407 recording section
1408 measurement/prescription results table
1502 prescription information table
1503, 1505 search section
1506 blood glucose measurement value
1602 measurement/prescription table
2202 nurse
2203 measuring tip
2204 insulin syringe
2205 patient
2306 patient ID
2307 nurse ID
2308 tip lot
2309 box
2402 fingertip
2403 puncture tool
2710 other patient

The invention claimed is:

1. A blood glucose measuring device comprising:
a patient ID reading section for acquiring a patient ID assigned to a patient;
a blood glucose measuring section for measuring blood glucose level of the blood drawn from the patient;
a nonvolatile storage for storing predetermined data;
a prescription information table stored in the nonvolatile storage, the prescription information table having prescription information stored therein in a manner in which the prescription information can be identified by the patient ID, the prescription information including kind and dosage of drugs for being administered corresponding to the blood glucose level of each of a plurality of patients;
a search section for searching, with blood glucose level and the patient ID, the prescription information table to acquire the prescription information of the patient;
a display unit for displaying the prescription information acquired by the search section;
an operating section for allowing an operator to input, in a state where the prescription information is displayed on the display unit, whether the prescription has been executed or not; and
a measurement/prescription results table stored in the nonvolatile storage, the measurement/prescription results table having: a patient ID field having the patient ID acquired by the patient ID reading section stored therein, a blood glucose level field for recording the blood glucose level of the patient measured by the blood glucose measuring section, a blood glucose measurement flag field for recording whether the blood glucose has been measured by the blood glucose measuring section or not, and an insulin administration confirmation flag field for recording whether the prescription has been executed or not after the prescription information has been displayed by the display unit;
the blood glucose measuring device further comprising:
a recording section; and
a control section;
wherein, when obtaining the blood glucose level from the blood glucose measuring section, the recording section records the blood glucose level in the blood glucose level field and records a logical true in the blood glucose measurement flag field of a record of the measurement/prescription results table, the record being identified by the patient ID, while when obtaining operation information from the operating section, the recording section records a logical true in the insulin administration confirmation flag field of the record;
wherein, after obtaining the patient ID by the patient ID reading section, the control section confirms the blood glucose measurement flag field and the insulin administration confirmation flag field of the record, and if the blood glucose measurement flag field of the record is "true" and the insulin administration confirmation flag field of the record is "false", the control section will control the search section to obtain the prescription information, while if the blood glucose measurement flag field of the record is "true" and the insulin administration confirmation flag field of the record is "true", the control section will not control the search section to obtain the prescription information, and the prescription information from the prescription information table of the patient is not displayed on the display unit, thereby preventing an accidental duplicate administration of insulin; and wherein, upon receipt of an indication to perform blood glucose measurement, the control section is configured to set the blood glucose measurement flag field to a logical false and the insulin administration confirmation flag field to a logical false.

2. The blood glucose measuring device according to claim 1, wherein the prescription information table outputs a plurality of pieces of prescription information with respect to one blood glucose level obtained by the blood glucose measuring section;

wherein the measurement/prescription results table has a plurality of the insulin administration confirmation flag fields, the number of the insulin administration confirmation flag fields being equal to the number of the pieces of prescription information outputted by the prescription information table; and wherein, in the case where there are a plurality of insulin administration confirmation flag fields in one record of the measurement/prescription results table, the control section does not control the search section to acquire the prescription information only when all of the insulin administration confirmation flag fields are "true".

3. The blood glucose measuring device according to claim 2, further comprising:

a communication section for performing data communication with a computer system storing the prescription information table therein in an editable manner; and a measurement/prescription table transmitted from the computer system and stored in the nonvolatile storage through the communication section, the measurement/prescription table including a patient ID field having the patient ID stored therein, a blood glucose measurement flag field for providing the indication to perform blood glucose measurement, and a prescription number field having the number of the kind of the drugs for being administered to the patient stored therein, wherein, when receiving the measurement/prescription table from the computer system, the control section creates the measurement/prescription results table in the nonvolatile storage according to the content of the measurement/prescription table.

* * * * *